(12) United States Patent
Sperandio et al.

(10) Patent No.: US 9,604,946 B2
(45) Date of Patent: Mar. 28, 2017

(54) METHODS FOR MODULATING BACTERIAL VIRULENCE AND RELATED COMPOUNDS

(71) Applicant: The Board of Regents of the University of Texas System, Austin, TX (US)

(72) Inventors: Vanessa Sperandio, Flower Mound, TX (US); John R. Falck, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/203,202

(22) Filed: Mar. 10, 2014

(65) Prior Publication Data
US 2014/0275189 A1    Sep. 18, 2014

Related U.S. Application Data

(60) Provisional application No. 61/777,994, filed on Mar. 12, 2013.

(51) Int. Cl.
| | |
|---|---|
| *A61K 31/425* | (2006.01) |
| *A01N 43/78* | (2006.01) |
| *C07D 277/48* | (2006.01) |
| *C07D 277/46* | (2006.01) |

(52) U.S. Cl.
CPC ......... *C07D 277/48* (2013.01); *C07D 277/46* (2013.01)

(58) Field of Classification Search
CPC .................. C07D 277/46; C07D 277/48
USPC .................. 514/371; 548/195, 196
See application file for complete search history.

(56) References Cited

U.S. PATENT DOCUMENTS

| | | |
|---|---|---|
| 8,252,841 B2 | 8/2012 | Sperandio et al. |
| 2012/0010187 A1* | 1/2012 | Hoffman ............. C07D 277/54 514/210.2 |

OTHER PUBLICATIONS

Clarke et al., "The QseC sensor kinase: a bacterial adrenergic receptor", *Proc. Natl. Acad. Sci. USA*, 103:10420-10425, 2006.
Rasko et al., "Targeting QseC signaling and virulence for antibiotic development", *Science*, 321:1078-1080, 2008.

* cited by examiner

*Primary Examiner* — My-Chau T Tran
(74) *Attorney, Agent, or Firm* — Parker Highlander PLLC

(57) ABSTRACT

The present invention relates to compounds and methods for the treatment of bacterial infections. The compounds and methods involve the disruption of the QseC signaling pathway which modulates the virulence of some bacteria. This methodology for treatment of bacterial infections reduces evolutionary pressure to develop resistance because the bacteria are not killed in the process.

33 Claims, 36 Drawing Sheets
(32 of 36 Drawing Sheet(s) Filed in Color)

Table S1. QseC Homologs

| Organism | Annotation | GenBank Accession | Similarity | Identity |
|---|---|---|---|---|
| Shigella flexneri 2a str. 301 | sensor protein QseC | NP_708838.1 | 93 | 92 |
| Citrobacter koseri ATCC BAA-895 | hypothetical protein CKO_04415 | YP_001455907.1 | 89 | 80 |
| Enterobacter sp. 638 | sensor protein QseC | YP_001178140.1 | 83 | 69 |
| Salmonella typhimurium LT2 | sensor protein QseC | NP_462093.1 | 87 | 79 |
| Salmonella enterica subsp. enterica serovar Typhi str. CT18 | sensor protein QseC | NP_457571.1 | 87 | 78 |
| Yersinia mollaretii ATCC 43969 | COG0642: Signal transduction histidine kinase | ZP_00825878.1 | 75 | 61 |
| Klebsiella pneumoniae subsp. pneumoniae MGH 78578 | putative 2-component sensor protein | YP_001337067.1 | 83 | 71 |
| Haemophilus influenzae PittGG | sensor protein QseC | YP_001291883.1 | 66 | 44 |
| Pasteurella multocida subsp. multocida str. Pm70 | YgiY | NP_245152.1 | 65 | 46 |
| Coxiella burnetii RSA 493 | sensor histidine kinase | NP_820223.1 | 49 | 32 |
| Burkholderia phymatum STM815 | periplasmic sensor signal transduction histidine kinase | ZP_01500068.1 | 53 | 36 |
| Ralstonia eutropha H16 | signal transduction histidine kinase | YP_725931.1 | 58 | 37 |
| Legionella pneumophila str. Paris | hypothetical protein lpp1254 | YP_123578.1 | 54 | 30 |
| Bordetella parapertussis 12822 | two-component system histidine kinase | NP_884854.1 | 56 | 37 |
| Francisella tularensis subsp. tularensis SCHU S4 | sensor histidine kinase | YP_169166.1 | 57 | 32 |
| Pseudomonas aeruginosa | probable two-component sensor | AAG08163.1 | 51 | 31 |
| Pseudomonas fluorescens Pf-5 | sensor histidine kinase | YP_260953.1 | 52 | 31 |
| Vibrio sp. | signal transduction histidine kinase | VVA0112 | 48 | 29 |
| Erwinia carotovora subsp. atroseptica SCRI1043 | sensor protein QseC | YP_048139.1 | 69 | 56 |
| Actinobacillus pleuropneumoniae serovar 1 str. 4074 | COG0642: Signal transduction histidine kinase | ZP_00204505.1 | 61 | 38 |
| Yersinia pestis CO92 | two-component system sensor protein | CAL22096.1 | 50 | 33 |
| Yersinia pseudotuberculosis IP 32953 | two-component system sensor protein | CAH19708.1 | 50 | 32 |
| Yersinia enterocolitica subsp. enterocolitica 8081 | sensor protein BasS/PmrB | YP_001004792.1 | 50 | 31 |
| Chromobacterium violaceum ATCC 12472 | sensor protein qseC | NP_900562.1 | 58 | 42 |

|  | ler | eae | stx2 |
| --- | --- | --- | --- |
| CF326 5nM | *** | *** | *** |
| CF326 5pM | *** | ** | *** |

A

B

CF327 agonist effect on *ler* and *stx*

A

B

|  | ler | eae | stx2 |
|---|---|---|---|
| CF329 5nM | *** | *** |  |
| CF329 5pM | *** | *** | *** |

A

B

A

B

A

B

A

B

A

CF338 qPCR

B

CF338 Survival within Macrophage

A

CF339 qPCR

B

CF339 Survival within Macrophage

A

CF340 qPCR

B

CF340 Survival within Macrophage

A

CF341 qPCR

B

CF341 Survival within Macrophage

A

CF342 qPCR

B

CF342 Survival Within Macrophages

A qPCR CF343

B

CF343 Survival within Macrophages

A

B

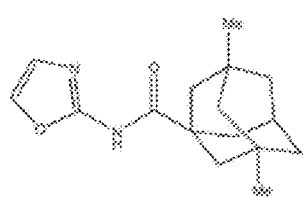
CF349
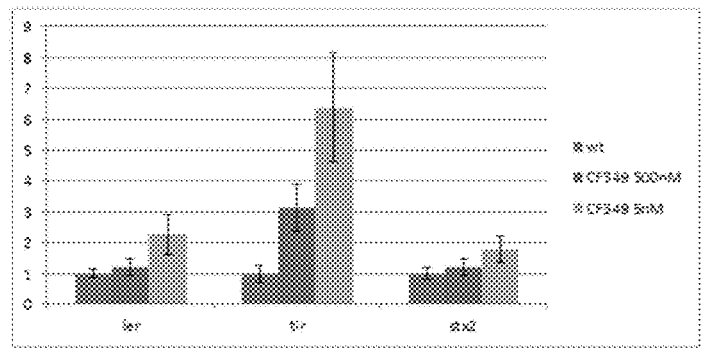
FIG. 21

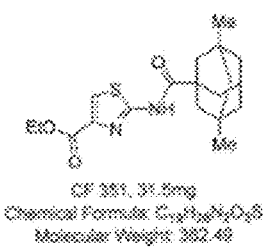
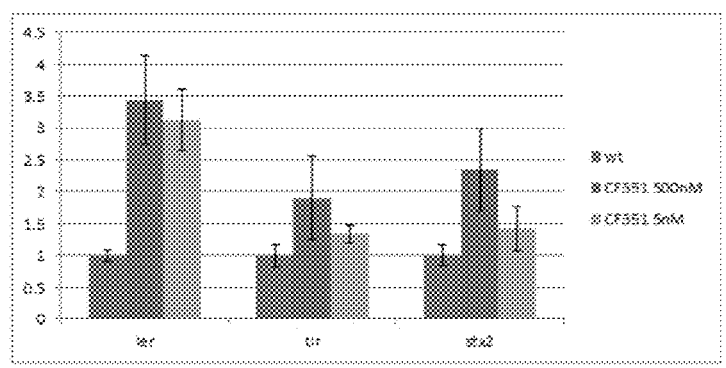
FIG. 23

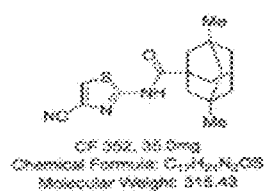
CF352
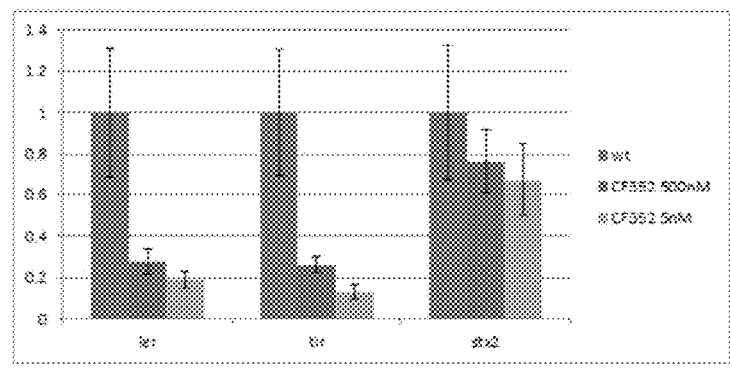
FIG. 24

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
cgaccaggtc tgcccttct                                                  19

<210> SEQ ID NO 2
<211> LENGTH: 17
<212> TYPE: DNA
<213> ORGANISM: Artificial Sequence
<220> FEATURE:
<223> OTHER INFORMATION: Synthetic primer

<400> SEQUENCE: 2
gccggaactc atcgaaa                                                    17

<210> SEQ ID NO 3
<211> LENGTH: 21
<212> TYPE: DNA
<213> ORGANISM: Artificial Sequence
<220> FEATURE:
```

<223> OTHER INFORMATION: Synthetic primer

<400> SEQUENCE: 3
tccatcgaca aattccgttc t                                                    21

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
tggtgactgc ggaatcca                                                        18

<210> SEQ ID NO 5
<211> LENGTH: 16
<212> TYPE: DNA
<213> ORGANISM: Artificial Sequence
<220> FEATURE:
<223> OTHER INFORMATION: Synthetic primer

<400> SEQUENCE: 5
accccaccgg gcagtt                                                          16

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
ggtcaaaacg cgcctgata                                                       19

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
tttcgtctcg gcataaatga a                                                    21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
tcattcagca agcgtgttga c                                                    21

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
gctggccttg gtttgatca                                                       19

```
<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gcggagatga cttcagcact t                                        21

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gcgctcatct tcttccgaat                                          20

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
cgcggtcgtg gttatgtg                                            18
```

METHODS FOR MODULATING BACTERIAL VIRULENCE AND RELATED COMPOUNDS

This application claims benefit of priority to U.S. Provisional Application Ser. No. 61/777,994, filed Mar. 12, 2013, the entire contents of which are hereby incorporated by reference.

This invention was made with government support under grant numbers UO1 01AI77853 awarded by the National Institutes of Health (NIH). The government has certain rights in the invention.

BACKGROUND OF THE INVENTION

1. Field of the Invention

The present invention generally relates to the fields of bacteriology and infectious diseases. More specifically, it relates to inhibitors of certain bacterial signaling mechanisms and bacterial infection treatments using these inhibitors.

2. Description of Related Art

Treatment of bacterial infections typically involves administration of one or more antibiotics. These agents, while often initially effective, may cause development of bacterial resistance to one or more types of antibiotics. Indeed, multi-drug resistant bacterial infections are a significant health concern throughout the world. Treatment methods that effectively eliminate bacterial infections without inducing bacterial resistance are therefore needed.

Quorum sensing (QS) is a mechanism that allows bacteria to respond to hormone-like molecules called autoinducers (AI) and is responsible for controlling a plethora of virulence genes in several bacterial pathogens. Because QS is not directly involved in essential processes such as growth of the bacteria, inhibition of QS should not yield a selective pressure for development of resistance (Rasmussen and Givskov, 2006).

A signaling cascade in enterohemorrhagic *E. coli* O157:H7 (EHEC) has been previously reported and is involved with QS by signaling with autoinducer-3 (AI-3) (Clarke et al., 2006). The AI-3/epinephrine (epi)/norepinephrine (NE) inter-kingdom signaling cascade activates expression of the flagella regulon (necessary for the bacteria to swim through the mucus layer, and reach the epithelial barriers), the LEE genes (encodes a specialized secretory pathway, through which bacteria secrete toxins to the mammalian cells, which culminate in diarrhea) and Shiga toxin genes (responsible for hemolytic uremic syndrome (HUS)) in EHEC (Sperandio et al., 2003; Clarke et al., 2006; Walters et al., 2006). AI-3 and epinephrine/NE are agonistic signals, and response to both signals can be blocked by adrenergic antagonists such as phentolamine or propranolol (Sperandio et al., 2003; Clarke et al., 2006; Walters et al., 2006; Walter and Sperandio, 2006). These signals are sensed by sensor kinases in the membrane of EHEC that relay this information through a complex regulatory cascade that activates the expression of the flagella regulon, the LEE genes and Shiga toxin. QseC (Quorum sensing *E. coli* regulator C) is one of these sensor kinases. QseC specifically senses AI-3/epinephrine and NE to augment its phosphorylation state, and that QseC directly binds to NE (Clarke et al., 2006). QseC's recognition of these signals can be blocked with the α-adrenergic antagonist phentolamine (Clarke et al., 2006). The QseC regulon is very complex and is intrinsically involved in the regulation of all known, and potentially several unknown, EHEC virulence genes.

Manipulation of QseC and/or the AI-3/epi/NE signaling cascade may offer a means of controlling bacterial virulence and thus, bacterial infections. Such means may minimize the probability of inducing bacterial resistance relative to conventional antibiotics. Agents that modulate these systems therefore merit investigation. Early work in the area of blocking the quorum sensing signals has been carried out by the current inventors. This work showed that a lead molecule LED209 can block the QseC response to the signal in U.S. Pat. No. 8,252,841, which is incorporated herein by reference. In that scenario, the LED209 small molecule and α-adrenergic antagonist (phentolamine; PE) block this response while β-adrenergic antagonist does antagonize the QseC recognition of a signal (Clarke et al., 2006, Rasko et al., 2008). However, additional compounds with distinct or improved activity are desired.

Furthermore, in addition to molecules that can decrease virulence, compounds which also modulate the activity of bacterial by increasing their virulence could be useful research tools. Such compounds could aid in the advancement of the understanding of quorum sensing and how virulence is regulated by quorum sensing and its related chemical signals.

SUMMARY OF THE INVENTION

The present invention is based on the discovery that certain compounds inhibit bacterial virulence by interfering with bacterial host communication. In general, these compounds do not kill or inhibit bacterial growth, but instead interfere with the bacteria's ability to recognize signals to activate its virulence genes. This is a novel strategy to fight bacterial infection: instead of "attacking" the bacterial cell, these compounds "confuse" communication to render the cell "blind" to the host. Because this strategy does not attack the bacteria per se as do conventional antibiotics, the evolutionary pressure for bacteria to evolve resistance mechanisms to this type of treatment is low. This approach has broad applicability as it is useful not only for certain mammalian bacterial pathogens, but also certain plant bacterial pathogens, such as *Erwinia* and *Ralstonia*. Indeed, compounds of the present invention may be applied in any number of medical (e.g., infection treatment), agricultural (e.g., plant disease eradication), or environmental (e.g., elimination of environmentally destructive species) purposes.

Accordingly, compounds of the present invention may, in certain embodiments, be inhibitors of quorum sensing that would otherwise lead to pathogenesis or virulence. Thus, compounds of the present invention, in certain embodiments, inhibit virulence. Compounds of the present invention may, in certain embodiments, be inhibitors of AI-3/epinephrine/NE signaling, such as in EHEC, *Salmonella* and *F. tularensis* pathogenesis. For example, in certain embodiments, compounds of the present invention inhibit Shiga toxin production. In certain embodiments, the compounds of the present invention inhibit QseC (Quorum sensing *E. coli* regulator C), a histidine sensor kinase. Compounds of the present invention may also be used to treat infections in plants. QseC has been involved in the virulence of every pathogen examined thus far, including EHEC, *Salmonella*, UPEC, non-typeable *Haemophilus influenza, Aeromonas hydrophila, Aggregatibacter actinomycetemcomitans, Edwardsiella tarda*, and *F. tularensis* (Hadjifrangiskou, et al., 2011; Khajanchi et al., 2012; Kostakioti et al., 2012a; Kostakioti et al., 2012b; Kostakioti et al., 2009; Mokrievich et al., 2010; Moreira et al., 2010; Novak et al., 2010; Rasko et al., 2008; Unal et al., 2012; Wang, et al., 2011; Weiss et al., 2007). In certain embodiments, compounds of the present invention inhibit virulence but do not kill bacteria (i.e., they are not bacteriocidal) nor are they bacteriostatic. Other methods of the present invention are described herein.

Compounds of the present invention that may be employed in any method of the present invention are described herein.

In some aspects of the present invention, there is provided a method of treating or preventing bacterial infection in a subject, comprising administering to the subject an effective amount of the following molecular formula:

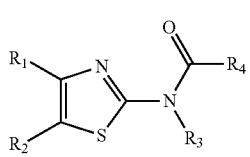
(I)

wherein: $R_1$ and $R_2$ are each independently hydrogen, cyano, nitro, halo, —C(O)OCH$_2$CH$_3$, $C_1$-$C_8$-alkyl, $C_1$-$C_8$-aryl, or a substituted version of those groups; $R_3$ is hydrogen or $C_1$-$C_6$-alkyl; or $R_4$ is $C_1$-$C_{10}$-aryl, $C_1$-$C_6$-alkyl, $C_6$-$C_{12}$-cycloalkyl, or a substituted version of those groups or a pharmaceutically acceptable salt, thereof.

In some embodiments, $R_3$ is hydrogen. In other embodiments, $R_3$ is methyl. In some embodiments, $R_1$ is hydrogen. In other embodiments, $R_1$ is methyl. In some embodiments, $R_2$ is hydrogen. In other embodiments, $R_2$ is methyl. In other embodiments, $R_2$ are halo, specifically, fluoro. In other embodiments, $R_2$ is nitro. In other embodiments, $R_1$ is substituted aryl and $R_2$ is hydrogen. In some embodiments, the aryl group on $R_1$ is substituted with a methyl group in the 4-position. In other embodiments, $R_1$ is cyano and $R_2$ is hydrogen. In other embodiments, $R_1$ is hydrogen and $R_2$ is cyano. In other embodiments, $R_1$ is —C(O)OCH$_2$CH$_3$ and $R_2$ is hydrogen.

In some embodiments, $R_4$ is aryl or substituted aryl. In some embodiments, $R_4$ is substituted aryl. In some embodiments, $R_4$ is a substituted aryl group of the formula:

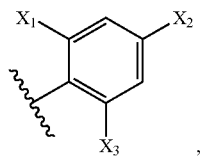

wherein: $X_1$, $X_2$, and $X_3$ are each independently hydrogen, halo, or —OMe. In some embodiments, $R_4$ is a substituted aryl where $X_1$, $X_2$, and $X_3$ are halo, specifically $X_1$, $X_2$, and $X_3$ are —F or —Cl. In other embodiments, $R_4$ is a substituted aryl where $X_1$ and $X_2$, are —OMe and $X_3$ is hydrogen. In other embodiments, $R_4$ is a substituted aryl where $X_1$ and $X_3$, are —OMe and $X_2$ is hydrogen. In other embodiments, $R_4$ is alkyl. In other embodiments, $R_4$ is methyl. In other embodiments, $R_4$ is an unsubstituted or substituted cycloalkyl group. In other embodiments, $R_4$ is an unsubstituted or substituted $C_{10}$-$C_{12}$-cycloalkyl. In other embodiments, $R_4$ is a group of the molecular formula:

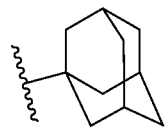

In other embodiments, $R_4$ is a group with the molecular formula:

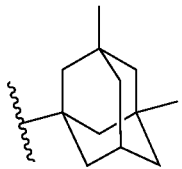

In other embodiments, $R_4$ is a group with the molecular formula:

In other embodiments, $R_4$ is

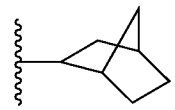

In some embodiments, the molecular formula of the compound is:

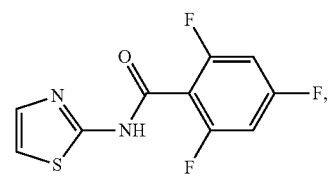

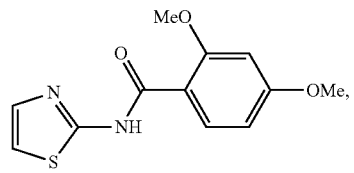

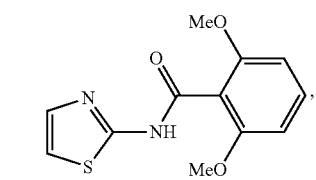

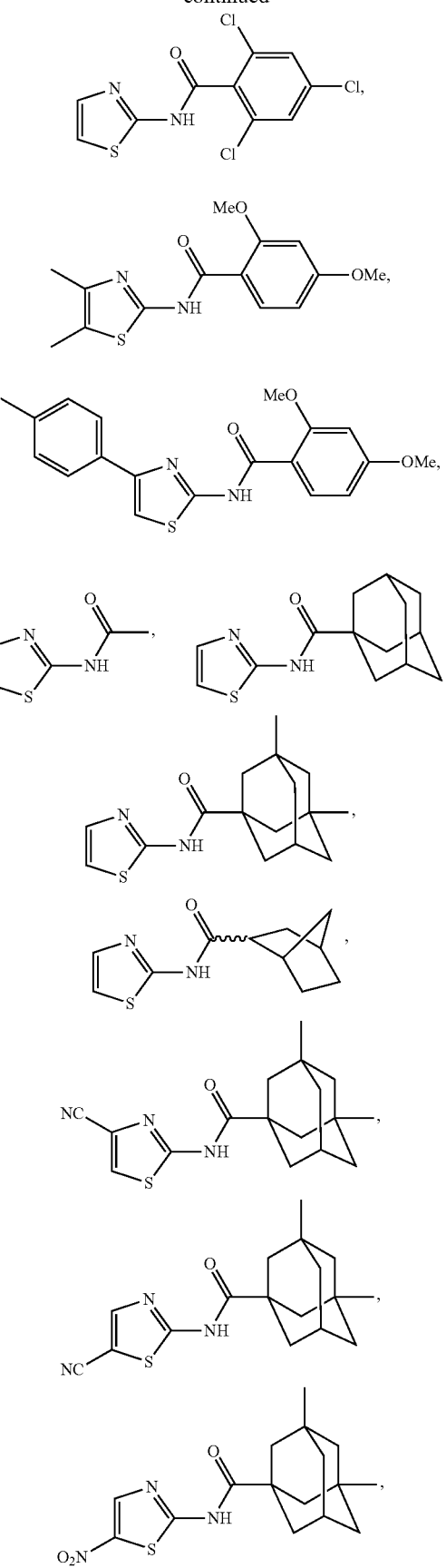
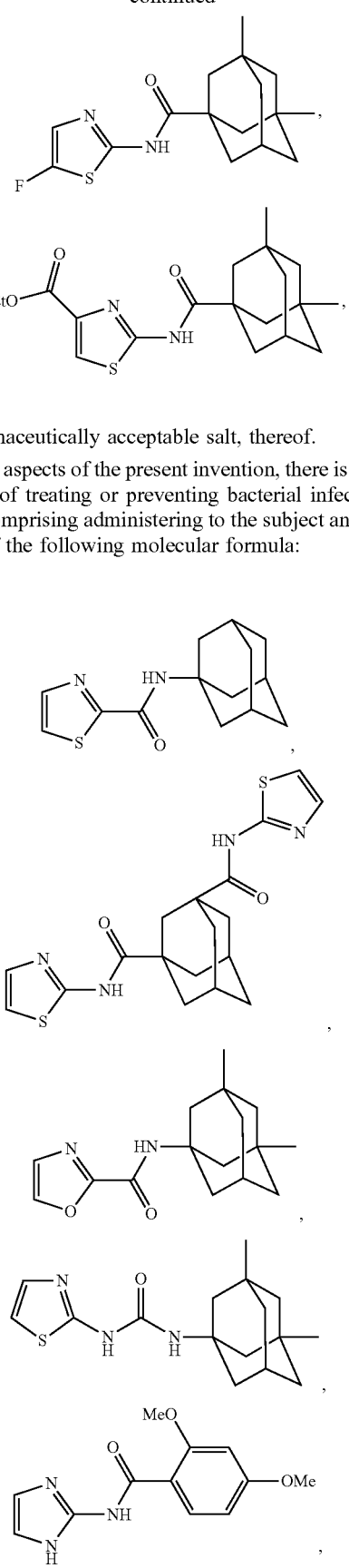
or a pharmaceutically acceptable salt, thereof.
In some aspects of the present invention, there is provided a method of treating or preventing bacterial infection in a subject, comprising administering to the subject an effective amount of the following molecular formula:

-continued

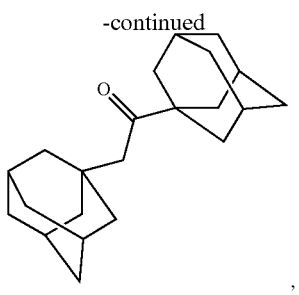

or a pharmaceutically acceptable salt, thereof.

In some aspects of the present invention, there is provided a method of treating or preventing bacterial infection in a subject, comprising administering to the subject an effective amount of a compound of any one of claims 1-30, wherein the subject is an animal or a plant.

In some embodiments, the bacterial infection is caused by a mammalian bacterial pathogen. In some embodiments, the bacterial infection is caused by at least one of the organisms *Acinetobacter, Aeromonas hydrophila, Actinobacillus pleuropneumoniae, Bordetella parapertussis, Burkholderia cepacia, Burkolderia phymatum, Chromobacter violaceum, Citrobacter, Coxiella burnetti,* enterotoxigenic *E. coli,* enteropathogenic *E. coli,* enteroaggregative *E. coli,* enteroinvasive *E. coli,* diffuse adhering *E. coli, E. coli* K1, uropathogenic *E. coli, E. coli, Edwardsiella tarda, Enterobacter, Erwinia carotovora, Francisella tularensis, Klebsiella pseumonia, Haemophilus influenzae, Legionella pneumophila, Pasteurella multocida, Pseudomonas aeruginosa, Pseudomonas fluorescens, Ralstonia euthropha, Ralstonia solanacearum, Shigella flexneri, Salmonella typhi, Salmonella typhimurium, Vibrio cholerae, Vibrio parahaemoliticus, Vibrio vulnificus, Yersinia enterocolitica, Yersinia mollareti, Yersinia pestis,* or *Yersinia pseudotuberculosis.* In some embodiments, the *E. coli* organism is a pathogenic *E. coli.* In other embodiments, the *E. coli* organism is enterohemorrhagic *E. coli.* In other embodiments, the *E. coli* organism is uropathogenic *E. coli.* In other embodiments, the organism is *Salmonella enterica.* In other embodiments, the organism is *Francisella tularensis.* In other embodiments, the organism is *Pseudomonas aeruginosa.* In other embodiments, the organism is *Klebsiella pseumonia.* In some embodiments, the *Acinetobacter* organism is *Acinetobacter baumannii.* In some embodiments, the bacterial infection is caused by bacteria that are a multi-drug resistant bacteria. In some embodiments, the compound described in the application is comprised in a pharmaceutically acceptable composition. In some embodiments, the composition is absorbable. In other embodiments, the composition is non-absorbable. In some embodiments, the pharmaceutically acceptable composition comprises an enteric coating. In some embodiments, the compound described in the application is administered orally, via inhalation, intraperitoneally, intravenously, intramuscularly, rectally, buccally, transdermally, vaginally, or via eye or ear drops. In some embodiments, the compound described in the application, is administered in an amount of about 0.1 to about 50 mg/kg body weight, more specifically is administered in an amount of about 10 to about 30 mg/kg body weight.

In some aspects of the present invention, there is provided a method of treating or preventing bacterial infection in a subject, comprising administering to the subject an effective amount of a compound described in the application, wherein the bacterial infection is caused by a bacterium that has a QseC kinase or QseC kinase homolog.

In some aspects of the present invention, there is provided a method of treating or preventing hemolytic uremic syndrome in a subject, comprising administering to the subject an effective amount of a compound described in the application.

In some aspects of the present invention, there is provided a method of treating or preventing bacterial infection in a subject, comprising administering to the subject an effective amount of a compound described in the application, wherein the compound minimally affects adrenergic receptor activity.

In some aspects of the present invention, there is provided a method of using a compound as an agonist of the virulence of a bacterial infection in a subject, comprising a compound described in the application.

In some aspects of the present invention, there is provided a compound selected from the group consisting of CF325, CF326, CF327, CF329, CF330, CF331, CF332, CF333, CF334, CF338, CF339, CF340, CF341, CF342, CF343, CF344, CF345, CF349, CF350, CF351, CF352 and CF354.

In some aspects of the present invention, there is provided a pharmaceutical composition comprising a compound selected from the group consisting of CF325, CF326, CF327, CF329, CF330, CF331, CF332, CF333, CF334, CF338, CF339, CF340, CF341, CF342, CF343, CF344, CF345, CF349, CF350, CF351, CF352 and CF354, formulated in a pharmaceutically acceptable diluent, buffer or excipient.

In some aspects of the present invention, there is provided a compound of the formula:

wherein: $X_1$ is

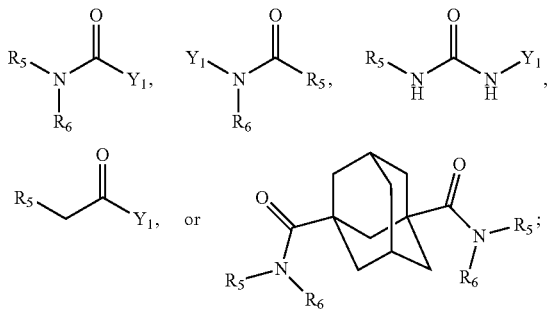

$R_5$ is

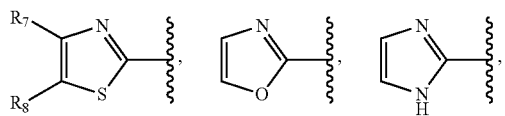

-continued

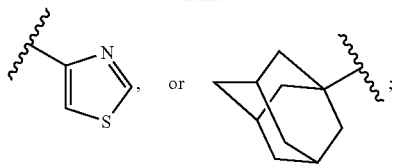

wherein: $R_6$ is hydrogen or $C_1$-$C_6$-alkyl; $R_7$ and $R_8$ are each independently hydrogen, cyano, nitro, halo, —C(O)OCH$_2$CH$_3$—C(O)OCH$_2$CH$_3$,

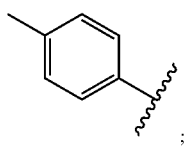 [SMILES: *c1ccc(C)cc1]

and $Y_1$ is methyl,

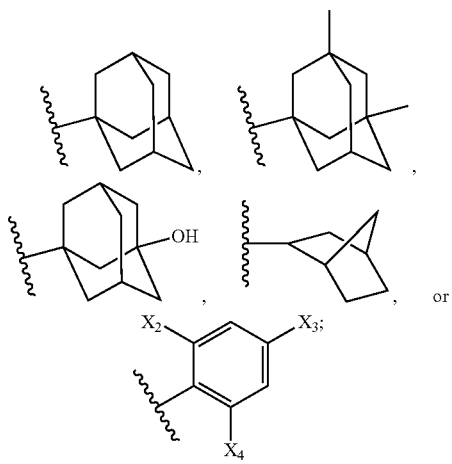

wherein: $X_2$, $X_3$, and $X_4$ are each independently hydrogen, halo, or —OMe.

Any compound of the present invention, such as a compound of formula (I), may be administered to a subject via any method known to those of skill in the art. In particular embodiments, a compound of the present invention is administered orally. Dosage amounts are described elsewhere in this application, but in certain embodiments, a compound of the present invention is administered in an amount of about 0.1 to about 50 mg/kg body weight. In certain embodiments, a compound of the present invention is administered in an amount of about 10 to about 30 mg/kg body weight. Compounds of the present invention may also be administered via inhalation, intraperitoneally, intravenously, intramuscularly, rectally, buccally (e.g., via a mouth wash), transdermally, vaginally, or via eye or ear drops.

In certain embodiments, bioavailable compounds of the present invention exhibiting a calculated water solubility of less than 1 mg/mL are preferred. Such values may be calculated by known in silico methods (e.g., Benchware™ HTS DataMiner, Tripos, Inc.). In certain embodiments, it is preferable that a compound of the present invention is comprised in a composition, such as a pharmaceutically acceptable composition, that is nonabsorbable. A nonabsorbable composition is one that is not, for the most part, absorbed by the body or any particular part of the body. That is, such compositions are not absorbed or metabolized by the body in any meaningful manner or to any meaningful degree. In certain embodiments, a compound is nonabsorbable from the gut, lumen of the GI tract, the nasal passage, the mouth cavity, the skin, the ear canal, and/or the vagina. Such compositions may be useful for targeting infections in the gut, for example (e.g., certain stages of Salmonella or EHEC infections), the ear (e.g., Haemophilus influenzae) or the vagina (e.g., Staphylococcus aureus (Staphylococcus epidermiditis, a close homolog of S. aureus, induces biofilm formation in the presence of norepinephrine), uropatogenic E. coli (UPEC) has a QseC homolog essential for pathogenesis (Kostakioti et al., 2009). In certain embodiments, a compound of the present invention may be conjugated to a carrier that is nonabsorbable, and then administered to a subject. An absorbable compound is also considered a bioavailable compound.

Such carriers include certain polymers, such nonabsorbable ones that are insoluble at the low pH of the stomach (pH 1-2) but readily dissolve at the pH of the intestine (pH>6.5) to release an encapsulated drug or expose a conjugated one. One specific class is the Eudragits™. Eudragits™ are completely nonabsorbable. When taken orally, they appear in the feces.

In certain embodiments, a compound of the present invention may be immobilized on a substrate or a medical device that is then inserted into a subject. A compound of the present invention may be chemically modified such that immobilizing the compound on a substrate or medical device is facilitated. In particular embodiments, a compound of the present invention comprises one or more polymer backbones, such as a linker-polymer backbone, and/or polymer tails that may then be used for immobilization purposes. Methods of immobilizing bioactive molecules onto such devices are well-known in the art. See, e.g., U.S. Pat. Nos. 5,811,151, 5,281,170, 6,024,918 and 7,256,259, each of which is incorporated by reference in its entirety. Substrates onto which compounds of the present invention may be immobilized may, in certain embodiments, be substantially insoluble in body fluids and that are generally designed and constructed to be placed in or onto the body or to contact fluid of the body. Non-limiting examples of medical devices include prostheses, stents, implants and ports.

In certain aspects of the present invention, any compound of the present invention, such as a compound of formula (I) minimally affects adrenergic receptor activity. Methods of determining adrenergic receptor activity are well-known to those of skill in the art (see, e.g., Azzi et al., 2001; Sen et al., 2002; Zimmerman et al., 1998). The phrase "minimally affects adrenergic receptor activity" refers to increasing or decreasing adrenergic receptor activity by about 1% or less.

In any method described herein, the bacterial infection may be caused by bacteria that have a QseC kinase or QseC kinase homolog. In any method described herein, the bacterial infection may be caused by bacteria that sense AI-3/epinephrine/NE. Methods of determining whether bacteria contain a QseC kinase and/or sense AI-3/epinephrine/NE are well-known to those of skill in the art. See, e.g., Clarke et al. (2006). Particular bacteria that contain a QseC kinase and that sense AI-3/epinephrine/NE include but are not limited to EHEC, EPEC, UPEC, K-12, Klebsiella pneumoniae, Acinetobacter baumannii, Shigela flexneri, Salmonella enterica typhi and typhimurium, Yersinia pestis, Yersinia enterocolitica, Yersinia, pseudotuberculosis, Erwinia carotovora, Pasteurella multocida, Haemophilus influenzae, Actinobacillus pleuroneumoniae, Chromobacterium viola-

*ceum, Pseudomonas aeruginosa, Pseudomonas fluorescens, Burkholderia cepacia, Coxiella burnetti, Vibrio parahaemolyticu, Ralstonia solanacenarum* and *Francisella tularensis*. Any QseC homologs listed in FIG. 2 are also contemplated by the present invention. It is contemplated that certain bacteria both contain QseC and detect AI-3/epinephrine/NE and certain bacteria either contain QseC or detect AI-3/epinephrine/NE.

In any method described herein, the bacterial infection may be caused by a multi-drug resistant bacteria. Non-limiting examples of such bacteria include *Salmonella* and *Staphylococci*, and others are well-known to those of skill in the art. Also envisioned are multi-drug resistant bacteria that develop in the future. Furthermore, in any method described herein, an infection may be caused by any organism discussed herein.

It is specifically contemplated that for every generic or specific compound disclosed herein that comprises a group comprising —C(O)NR— or —SO$_2$NR—, the reverse linkage of that group (e.g., —NRC(O)— or —NRSO$_2$—) also constitutes an embodiment of the present invention (wherein R is H or as otherwise shown herein). Moreover, for any aryl ring comprised in any generic or specific compound of the present invention that comprises an ortho, meta, or para substituent, it is specifically contemplated that the ortho, meta, or para substituent may be moved around the ring, and that more than one such substituent may be moved around a ring (e.g., an ortho group may be moved to the para position, and/or a para group may be moved to a meta position). In certain embodiments, for example, an —NHSO$_2$— moiety may be exchanged for —SO$_2$NH—, and then the —NHSO$_2$— moiety may be moved to an alternate position on an aryl ring.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition. For example, a subject (e.g., a mammal, such as a human) having a bacterial infection may be subjected to a treatment comprising administration of a compound of the present invention. Alternatively, a subject of the present invention may be a plant, such that the plant may be treated with a compound of the present invention to obtain a beneficial result (e.g., reduction of an infection).

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease. For example, a therapeutically effective amount of a compound of the present invention may be administered to a subject having a bacterial infection, such that the infection is mitigated or eliminated.

The term "subject" as used herein refers to an animal or plant, such as an infected animal or plant, or an animal or plant that is suspected of being infected or susceptible to infection. Animals include, for example, mammals, birds, fish, reptiles, amphibians, and any other vertebrates or invertebrates, such as those of economic, environmental, and/or other significant importance. Mammals include, but are not limited to, humans, livestock, and pets. Without limitation, "livestock" includes economically important animals such as cattle, sheep, goats, rabbits and horses. Birds include without limitation chickens, turkeys, ducks and geese. The term "plants", without limitation, may refer to, for example, plants that produce fruits, vegetables, grains, tubers, legumes, flowers, and leafs such as spinach or tobacco leaf, or any other economically or environmentally important plant.

The term "virulence" as used throughout this application refers to expression control of genes, proteins, or the exhibition of certain behaviors that allow infection of a host or the inhibition of treatment for infections. This includes, but is not limited to, production of toxins; production of proteins or other factors that allow the formation of lesions on subjects' cells or invasion of subjects' cells or tissues; formation of biofilms that resist treatment; formation of plaques in the oral cavity that lead to periodontal disease; and/or inhibition or displacement of commensal or probiotic organisms normally found in healthy subjects.

As used herein, "bacteriocidal" refers to killing of bacteria.

As used herein, "bacteriostatic" refers to inhibiting the growth or reproduction of bacteria.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

The patent or application file contains at least one drawing executed in color. Copies of this patent or patent application publication with color drawing(s) will be provided by the Office upon request and payment of the necessary fee.

FIG. 2. List of QseC homologs in other bacteria compared to EHEC QseC.

FIG. 4A Graph of the effects of CF326 on *S. Typhimurium* intra J774 macrophage replication. FIG. 4B Graph of the effects of CF326 on EHEC on gene expression measured by qRT-PCR as a change from wild-type expression.

FIG. 5A Graph of the effects of CF327 on *S. Typhimurium* intra J774 macrophage replication. FIG. 5B Graph of the effects of CF327 on EHEC on gene expression measured by qRT-PCR as a change from wild-type expression.

FIG. 7A Graph of the effects of CF329 on *S. Typhimurium* intra J774 macrophage replication. FIG. 7B Graph of the effects of CF329 on EHEC on gene expression measured by qRT-PCR as a change from wild-type expression.

FIG. 9A Graph of the effects of CF331 on EHEC on gene expression measured by qRT-PCR as a change from wild-type expression. FIG. 9B Microscopic image of fluorescein actin staining for HeLa cells treated with EHEC and CF331 at no compound, 500 nM CF331 and 5 nM CF331.

FIG. 10A Graph of the effects of CF332 on *S. Typhimurium* intra J774 macrophage replication. FIG. 10B Graph of the effects of CF332 on EHEC on gene expression measured by qRT-PCR as a change from wild-type expression.

FIG. 11A Graph of the effects of CF333 on *S. Typhimurium* intra J774 macrophage replication. FIG. 11B Graph of the effects of CF333 on EHEC on gene expression measured by qRT-PCR as a change from wild-type expression.

FIG. 12A Graph of the effects of CF334 on *S. Typhimurium* intra J774 macrophage replication. FIG. 12B Graph of the effects of CF334 on EHEC on gene expression measured by qRT-PCR as a change from wild-type expression.

FIG. 13A Graph of the effects of CF338 on EHEC on gene expression measured by qRT-PCR as a change from wild-type expression. FIG. 13B Graph of the effects of CF338 on *S. Typhimurium* intra J774 macrophage replication. FIG. 13C Microscopic image of fluorescein actin staining for HeLa cells treated with EHEC and CF338 at no compound, 500 nM CF338 and 5 nM CF338.

FIG. 14A Graph of the effects of CF339 on EHEC on gene expression measured by qRT-PCR as a change from wild-type expression. FIG. 14B Graph of the effects of CF339 on *S. Typhimurium* intra J774 macrophage replication.

FIG. 15A Graph of the effects of CF340 on EHEC on gene expression measured by qRT-PCR as a change from wild-type expression. FIG. 15B Graph of the effects of CF340 on *S. Typhimurium* intra J774 macrophage replication. FIG. 15C Microscopic image of fluorescein actin staining for HeLa cells treated with EHEC and CF340 at no compound, 500 nM CF340 and 5 nM CF340.

FIG. 16A Graph of the effects of CF341 on EHEC on gene expression measured by qRT-PCR as a change from wild-type expression. FIG. 16B Graph of the effects of CF341 on *S. Typhimurium* intra J774 macrophage replication. FIG. 16C Microscopic image of fluorescein actin staining for HeLa cells treated with EHEC and CF341 at no compound, 500 nM CF341 and 5 nM CF341.

FIG. 17A Graph of the effects of CF342 on EHEC on gene expression measured by qRT-PCR as a change from wild-type expression. FIG. 17B Graph of the effects of CF342 on *S. Typhimurium* intra J774 macrophage replication.

FIG. 18A Graph of the effects of CF343 on EHEC on gene expression measured by qRT-PCR as a change from wild-type expression. FIG. 18B Graph of the effects of CF343 on *S. Typhimurium* intra J774 macrophage replication.

FIG. 20A Graph of the effects of CF345 on EHEC on gene expression measured by qRT-PCR as a change from wild-type expression. FIG. 20B Microscopic image of fluorescein actin staining for HeLa cells treated with EHEC and CF345 at no compound, 500 nM CF345 and 5 nM CF345.

FIG. 21. Graph of the effects of CF349 on EHEC on gene expression measured by qRT-PCR as a change from wild-type expression.

FIG. 23. Graph of the effects of CF351 on EHEC on gene expression measured by qRT-PCR as a change from wild-type expression.

FIG. 24. Graph of the effects of CF352 on EHEC on gene expression measured by qRT-PCR as a change from wild-type expression.

DESCRIPTION OF ILLUSTRATIVE EMBODIMENTS

Figure 1:
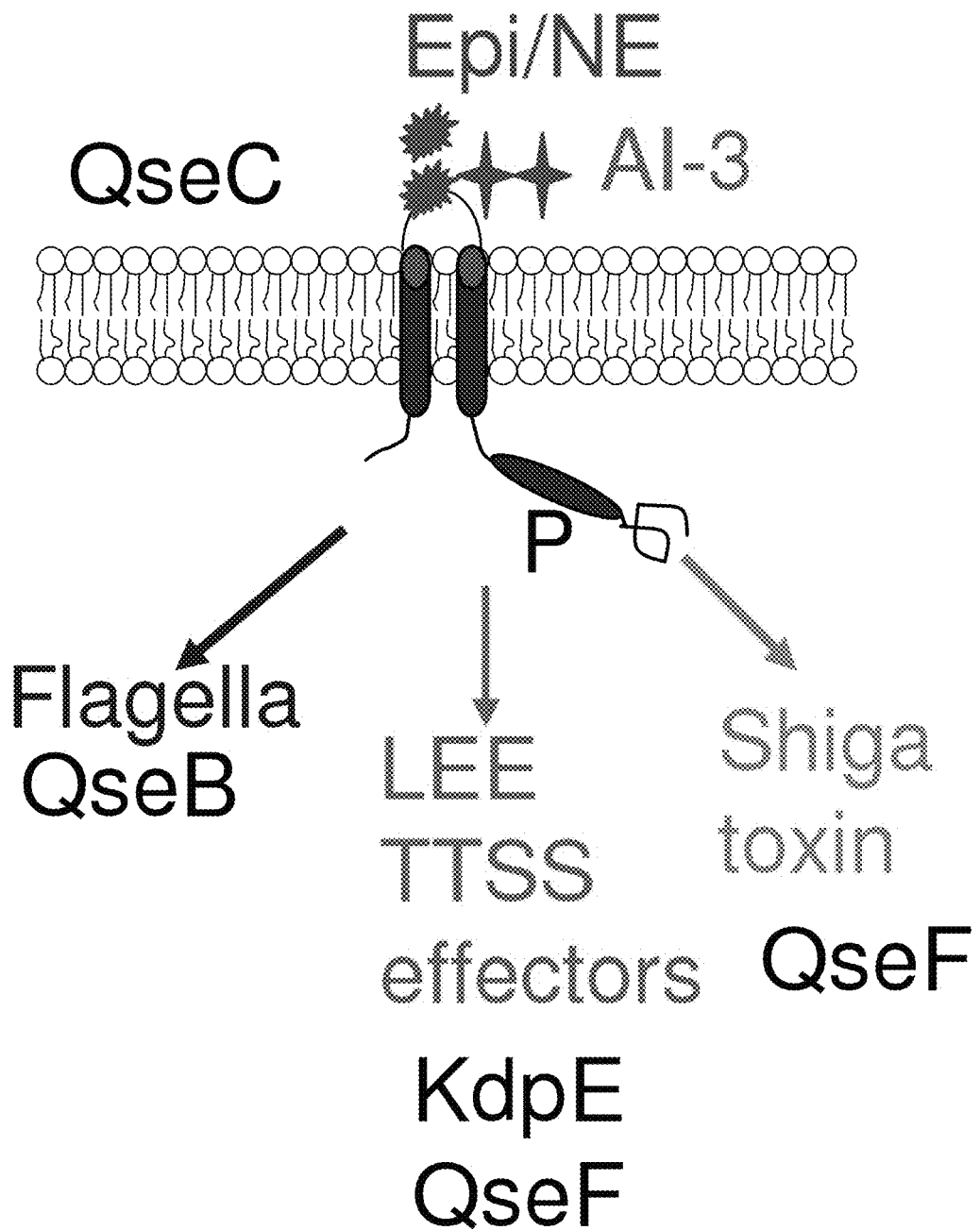
FIG. 1. Schematic autophosphorylation of QseC in response to signals and phosphotransfer to QseB, KdpE and QseF to regulate all virulence genes in EHEC including flagella, the locus of enterocyte effacement (LEE) and Shiga toxin.
Figure 3:
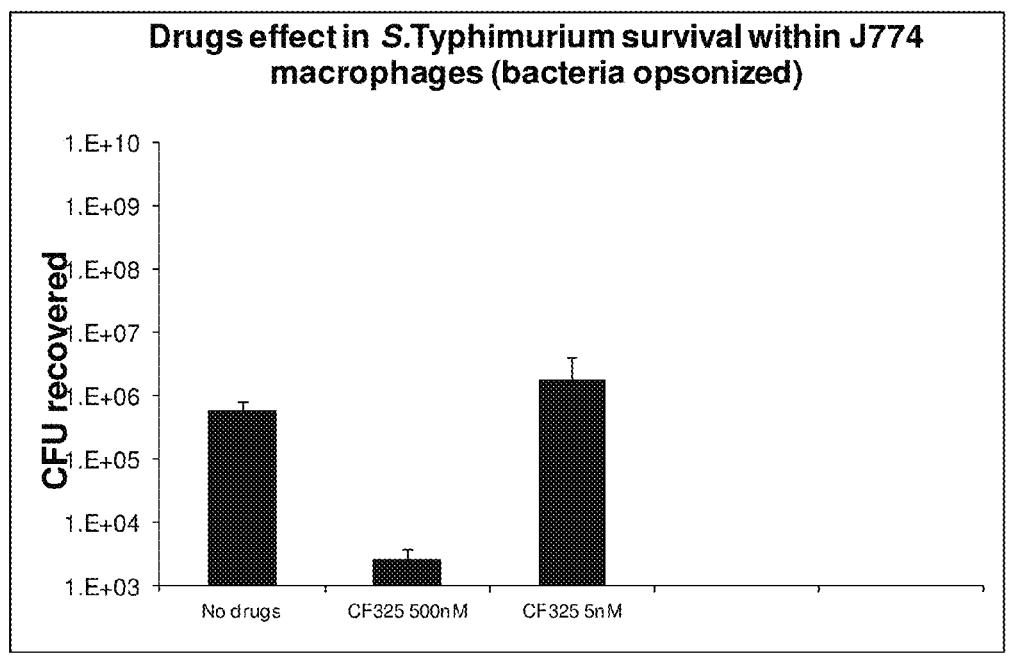
FIG. 3. Graph of the effects of CF325 on *S. Typhimurium* intra J774 macrophage replication.
Figure 4A:
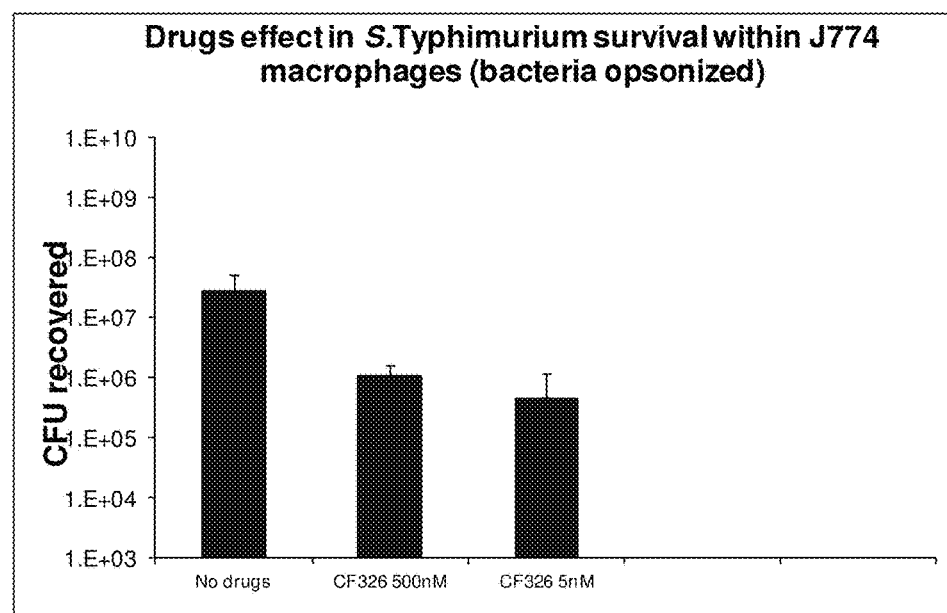
FIGS. 4A & 4B.
Figure 4B:
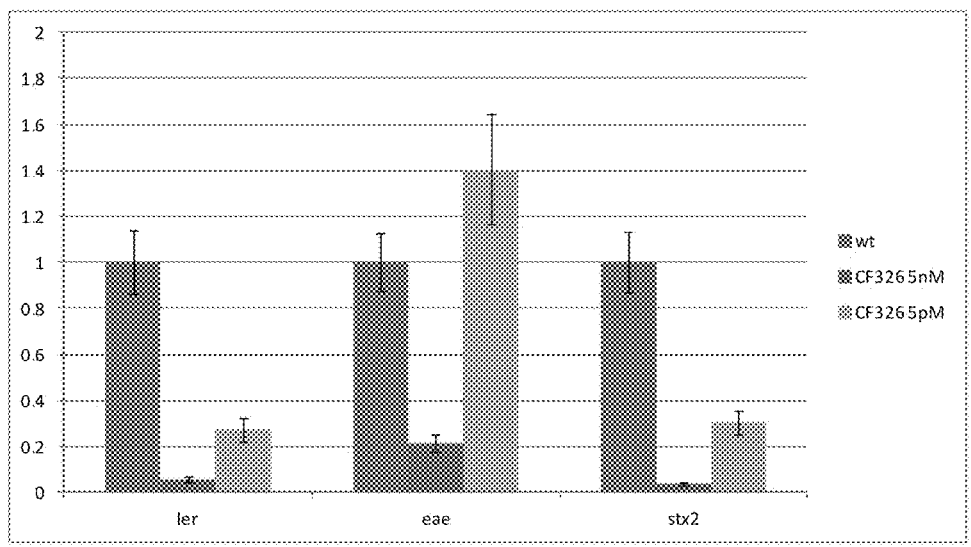
Figure 5A:
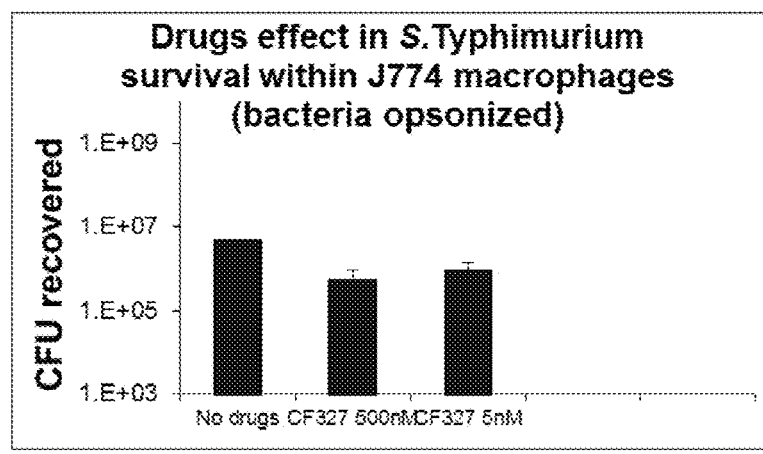
FIGS. 5A & 5B.
Figure 5B:
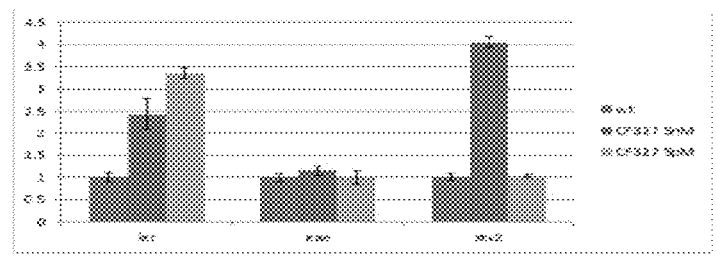
Figure 6:
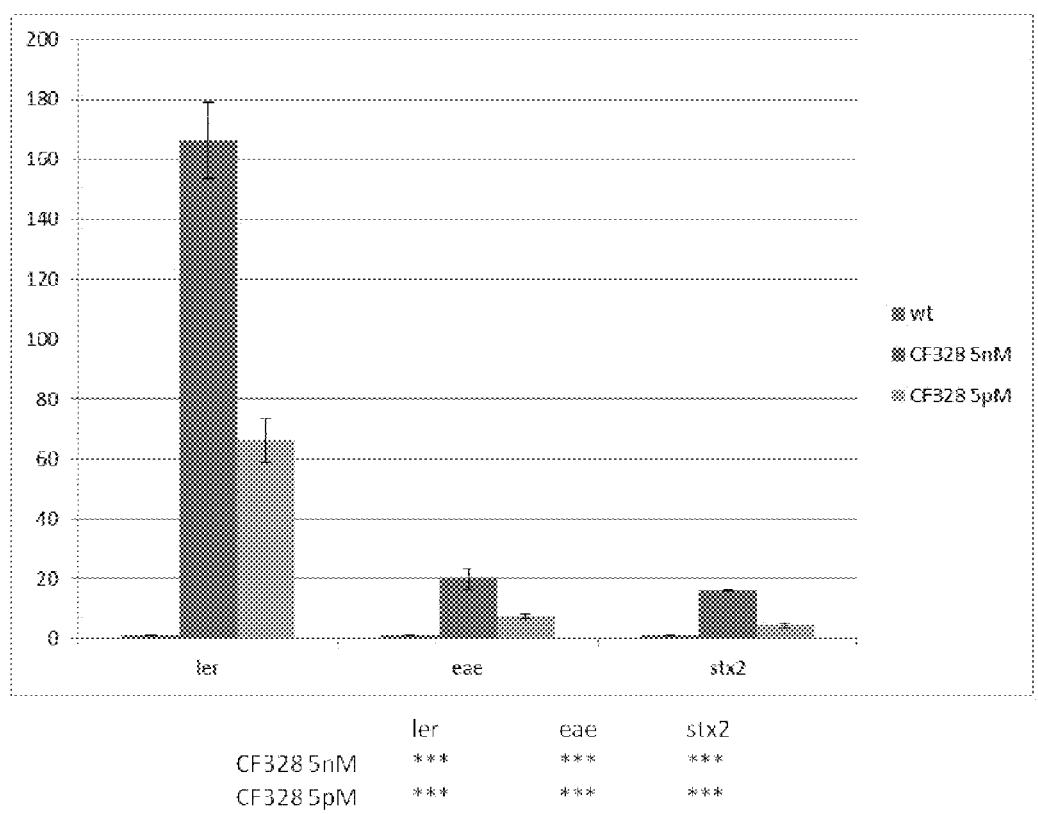
FIG. 6. Graph of the effects of CF328 on EHEC on gene expression measured by qRT-PCR as a change from wild-type expression.
Figure 7A:
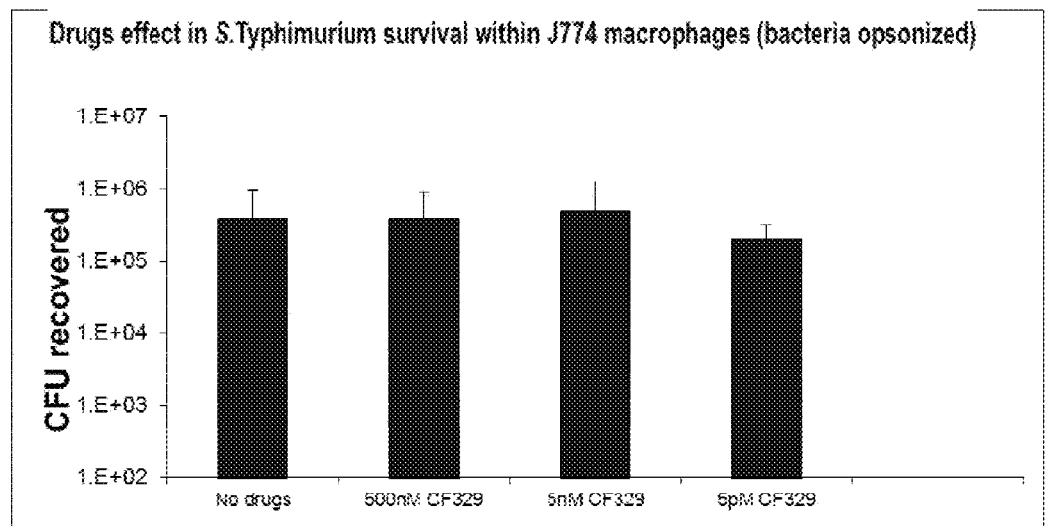
FIGS. 7A & 7B.
Figure 7B:
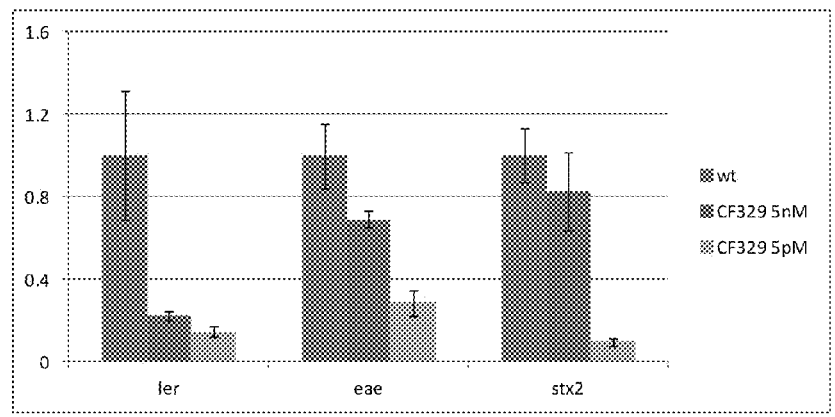
Figure 8:
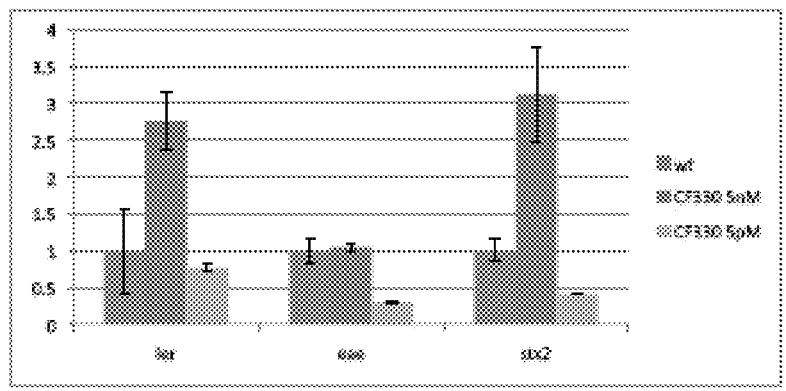
FIG. 8 Graph of the effects of CF330 on EHEC on gene expression measured by qRT-PCR as a change from wild-type expression.
Figure 9A:
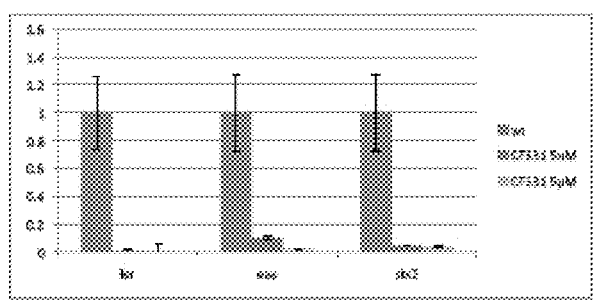
FIGS. 9A & 9B.
Figure 9B:
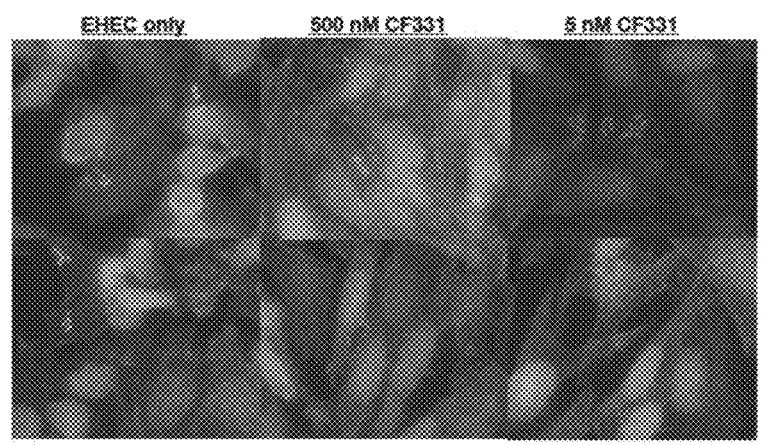
Figure 10A:
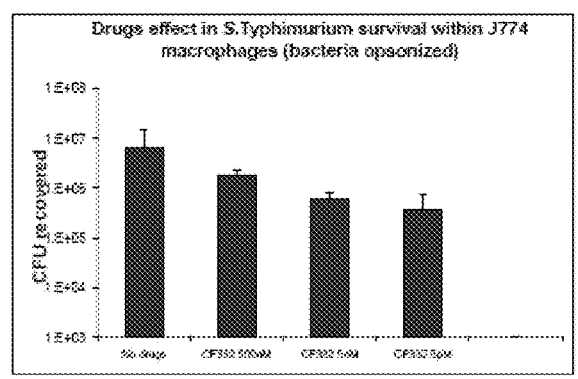
FIGS. 10A & 10B.
Figure 10B:
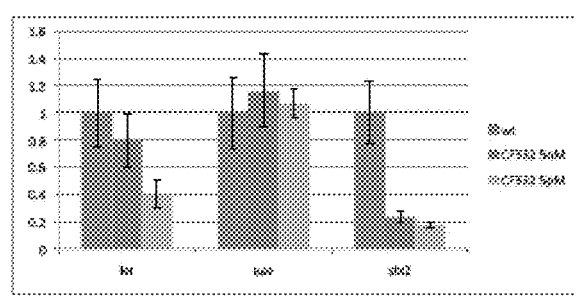
Figure 11A:
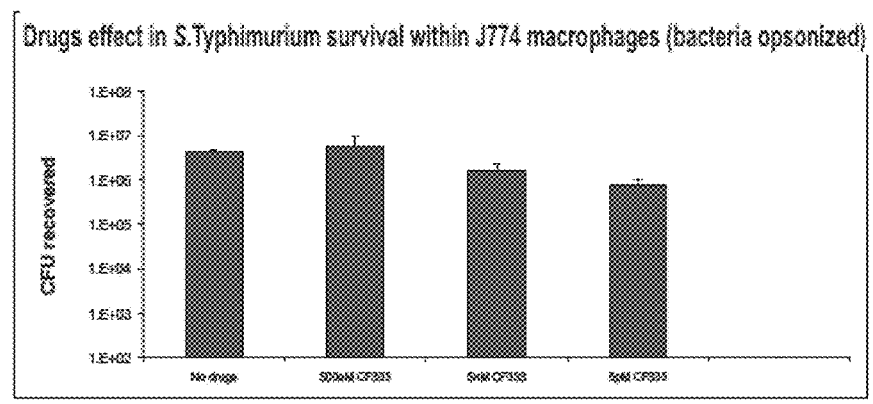
FIGS. 11A & 11B.
Figure 11B:
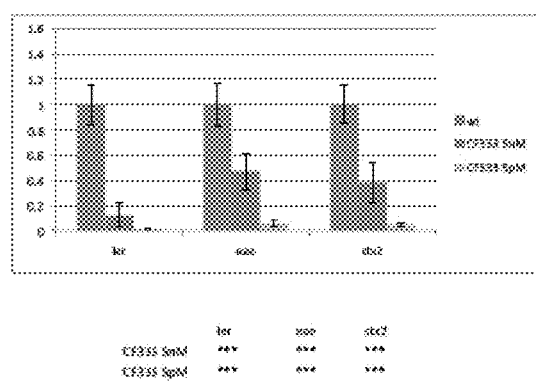
Figure 12A:
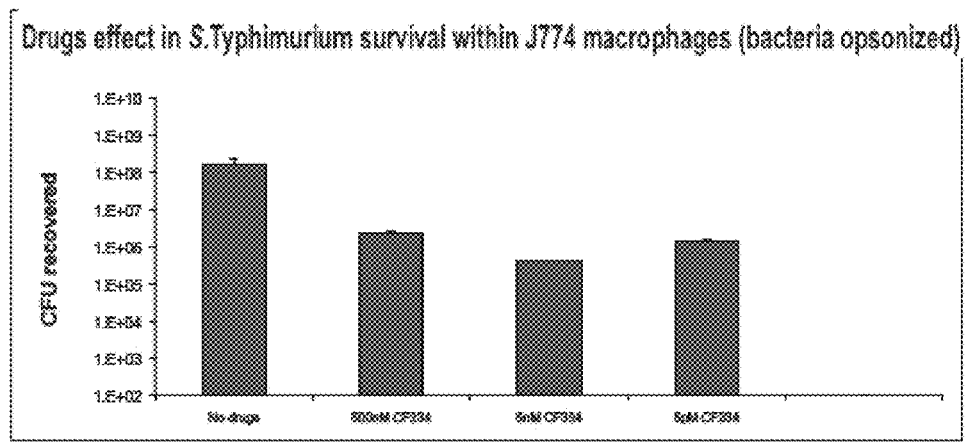
FIGS. 12A & 12B.
Figure 12B:
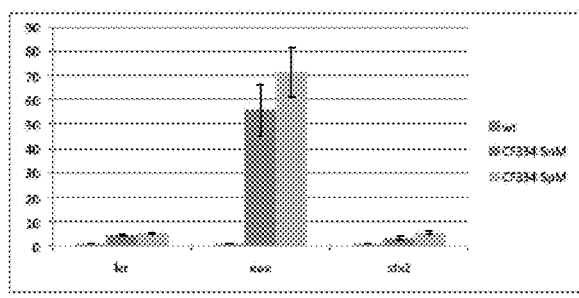
Figure 13A:
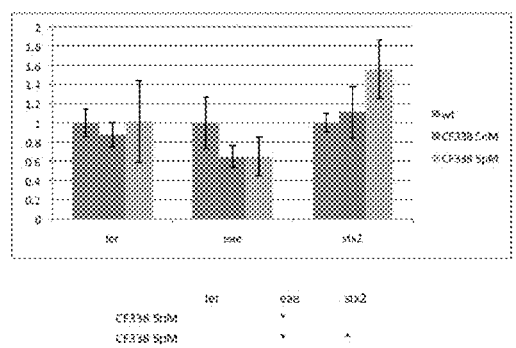
FIGS. 13A-C.
Figure 13B:
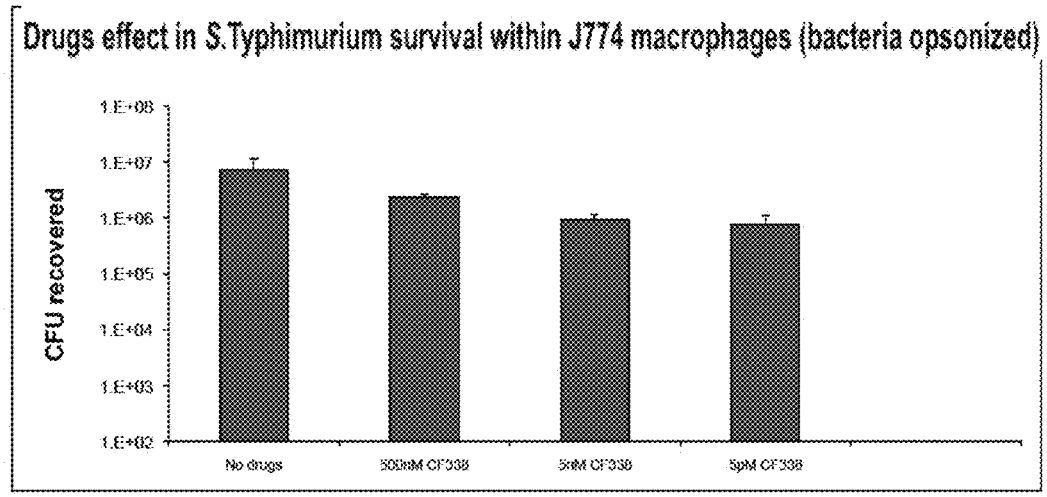
Figure 13C:
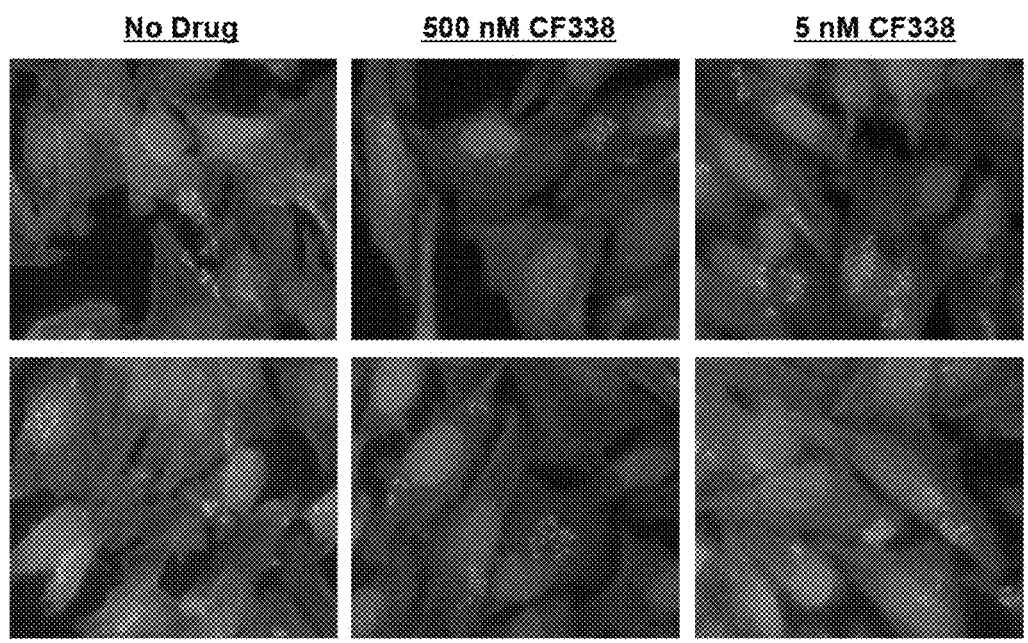
Figure 14A:
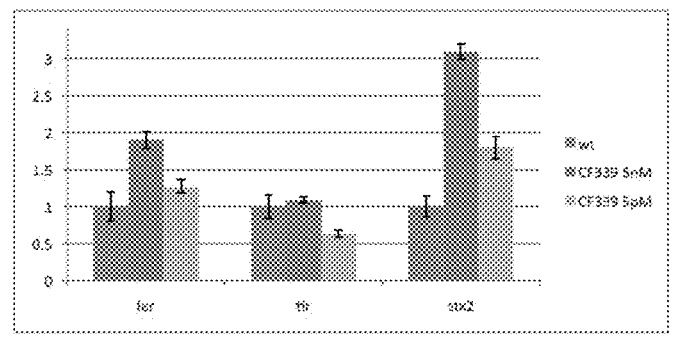
FIGS. 14A & 14B.
Figure 14B:
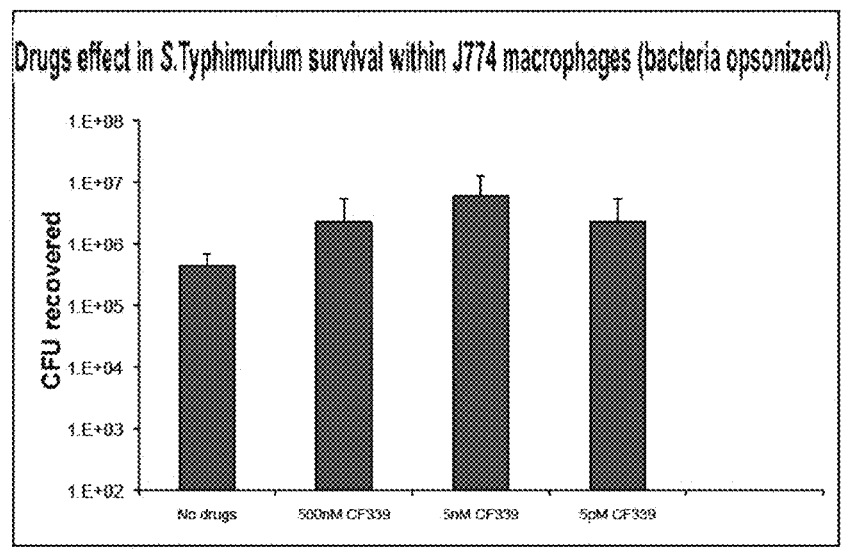
Figure 15A:
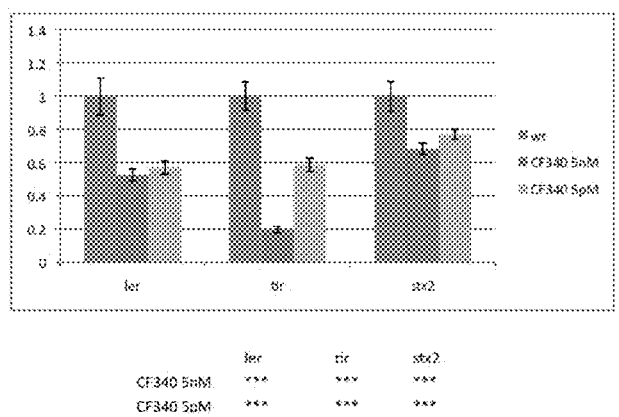
FIGS. 15A-C.
Figure 15B:
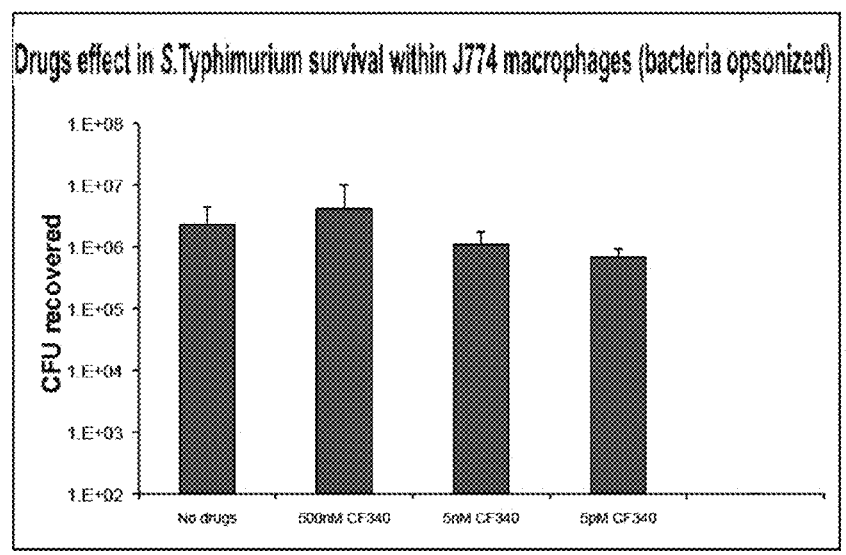
Figure 15C:
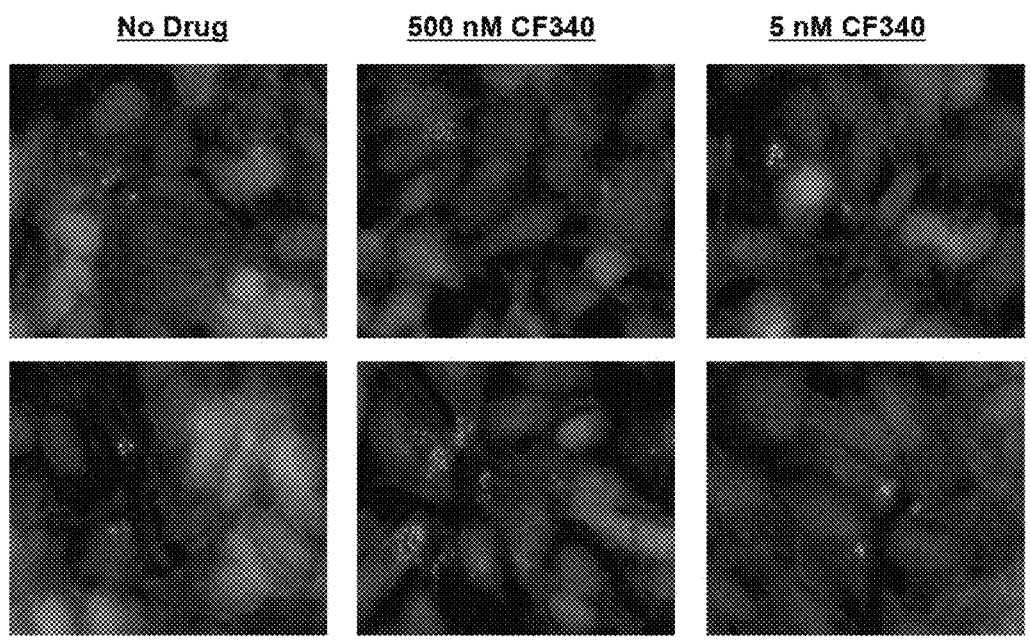
Figure 16A:
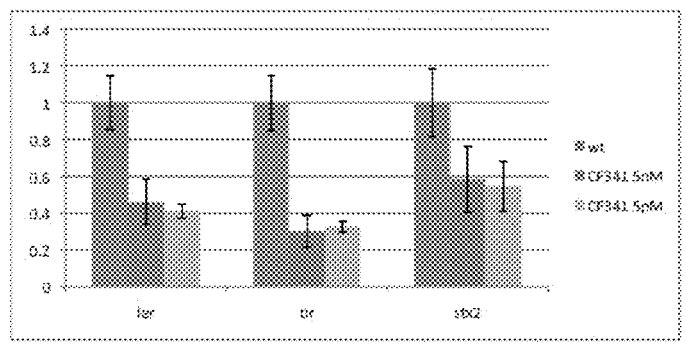
FIGS. 16A-C.
Figure 16B:
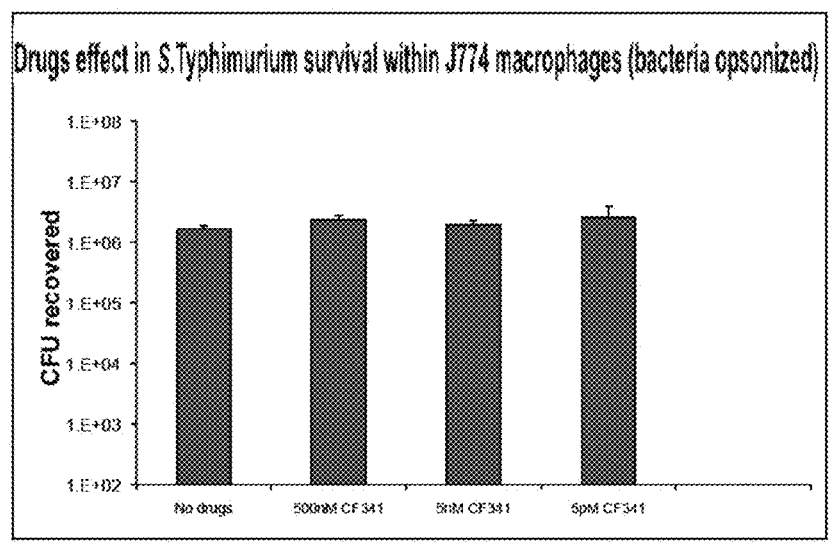
Figure 16C:
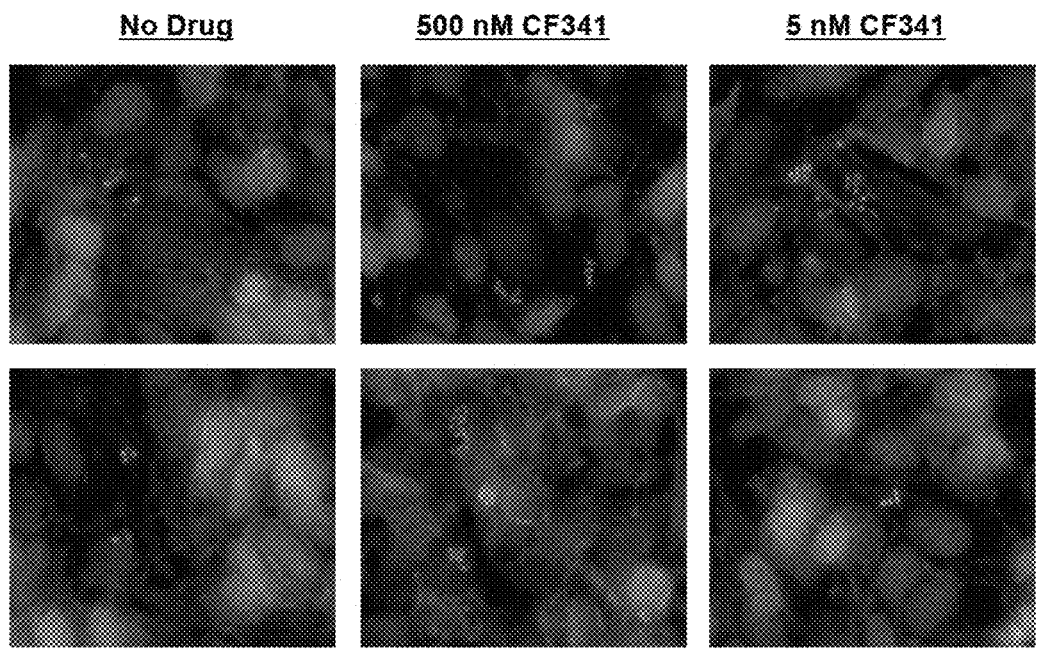
Figure 17A:
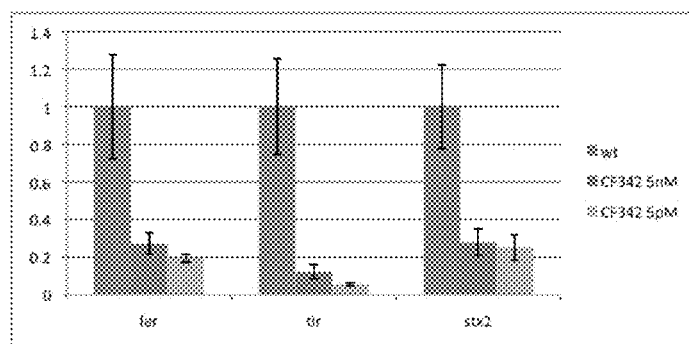
FIGS. 17A & 17B.
Figure 17B:
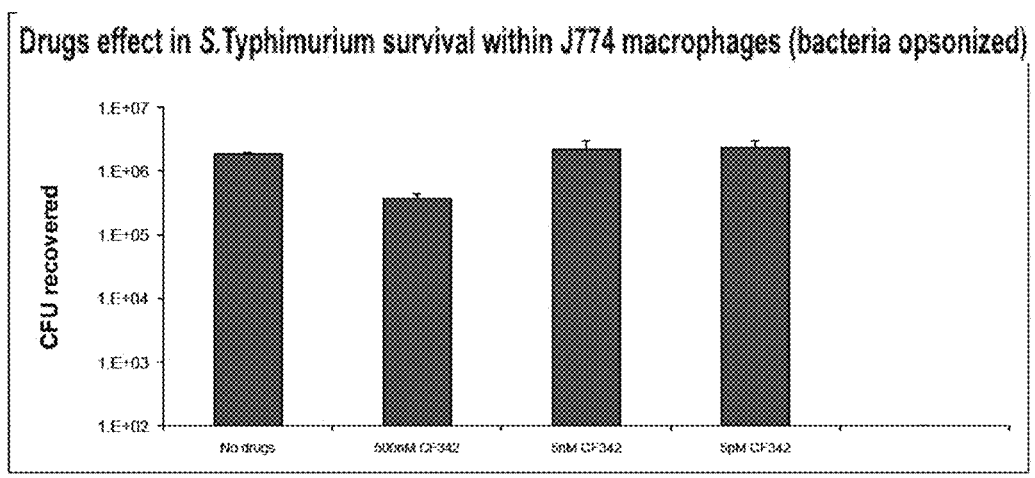
Figure 18A:
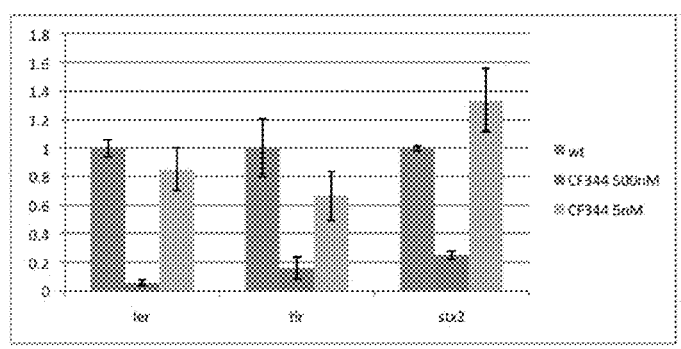
FIGS. 18A & 18B.
Figure 18B:
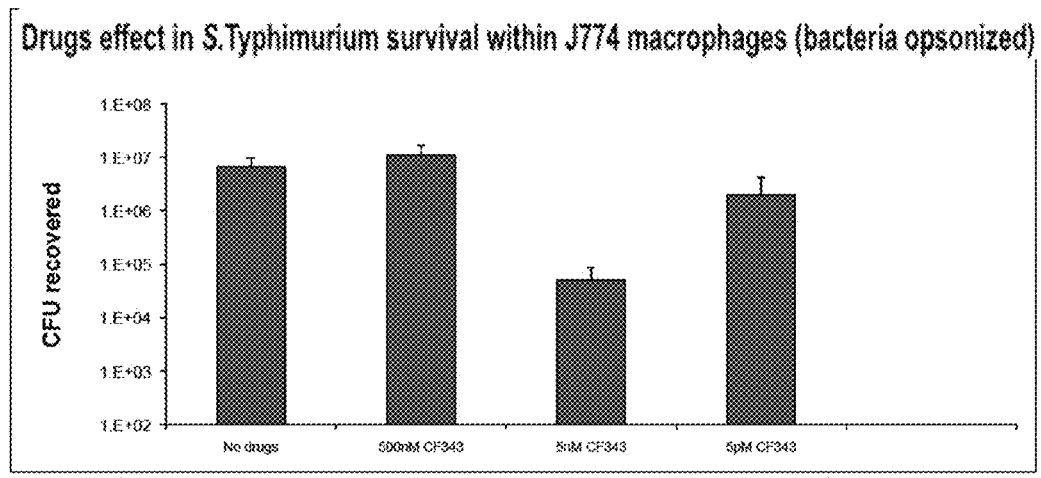
Figure 19:
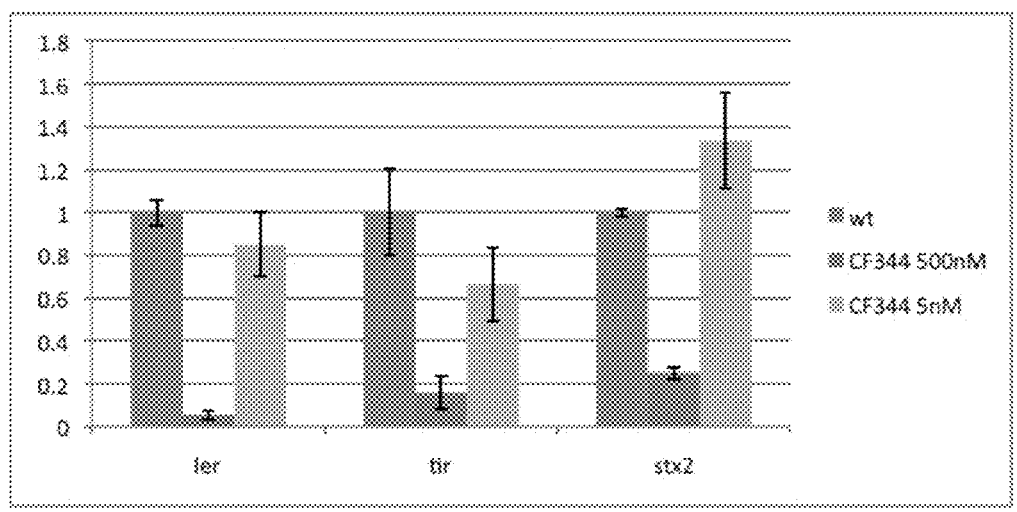
FIGS. 19. Graph of the effects of CF344 on EHEC on gene expression measured by qRT-PCR as a change from wild-type expression.
Figure 20A:
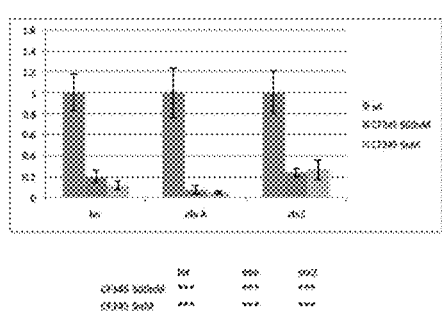
FIGS. 20A & 20B.
Figure 20B:
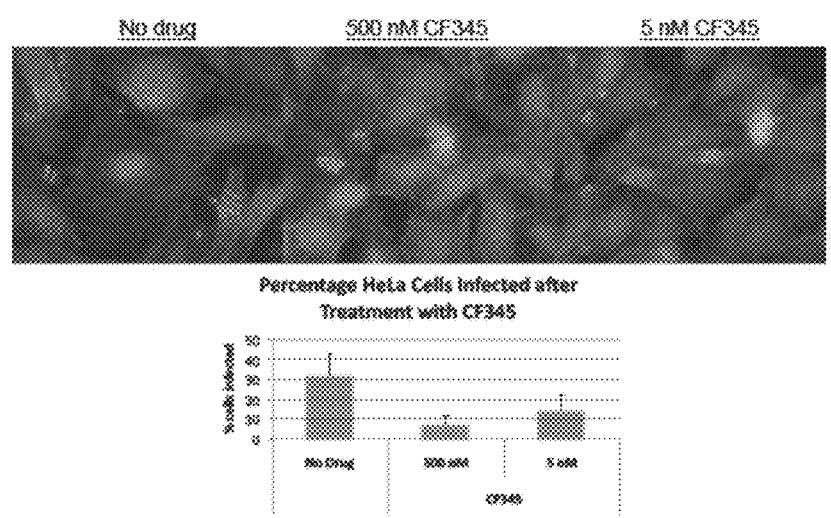
Figure 22:
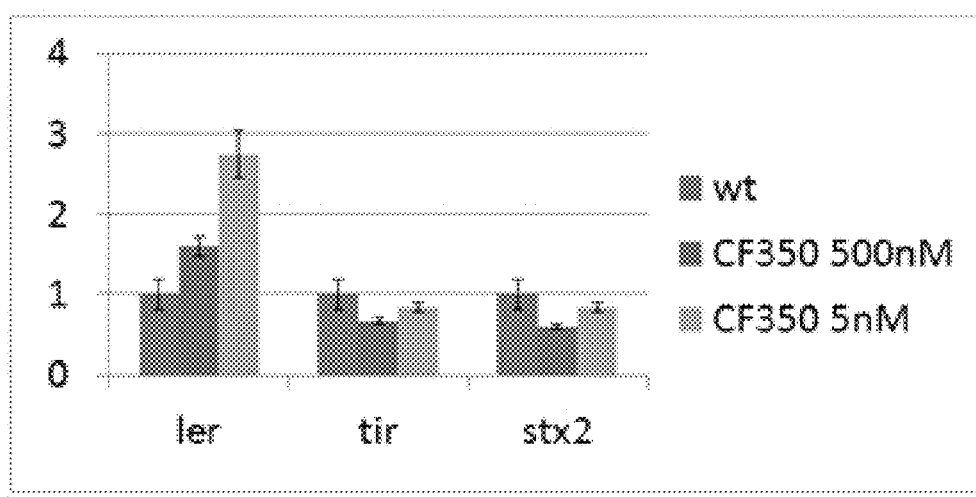
FIG. 22. Graph of the effects of CF350 on EHEC on gene expression measured by qRT-PCR as a change from wild-type expression.
Figure 25:
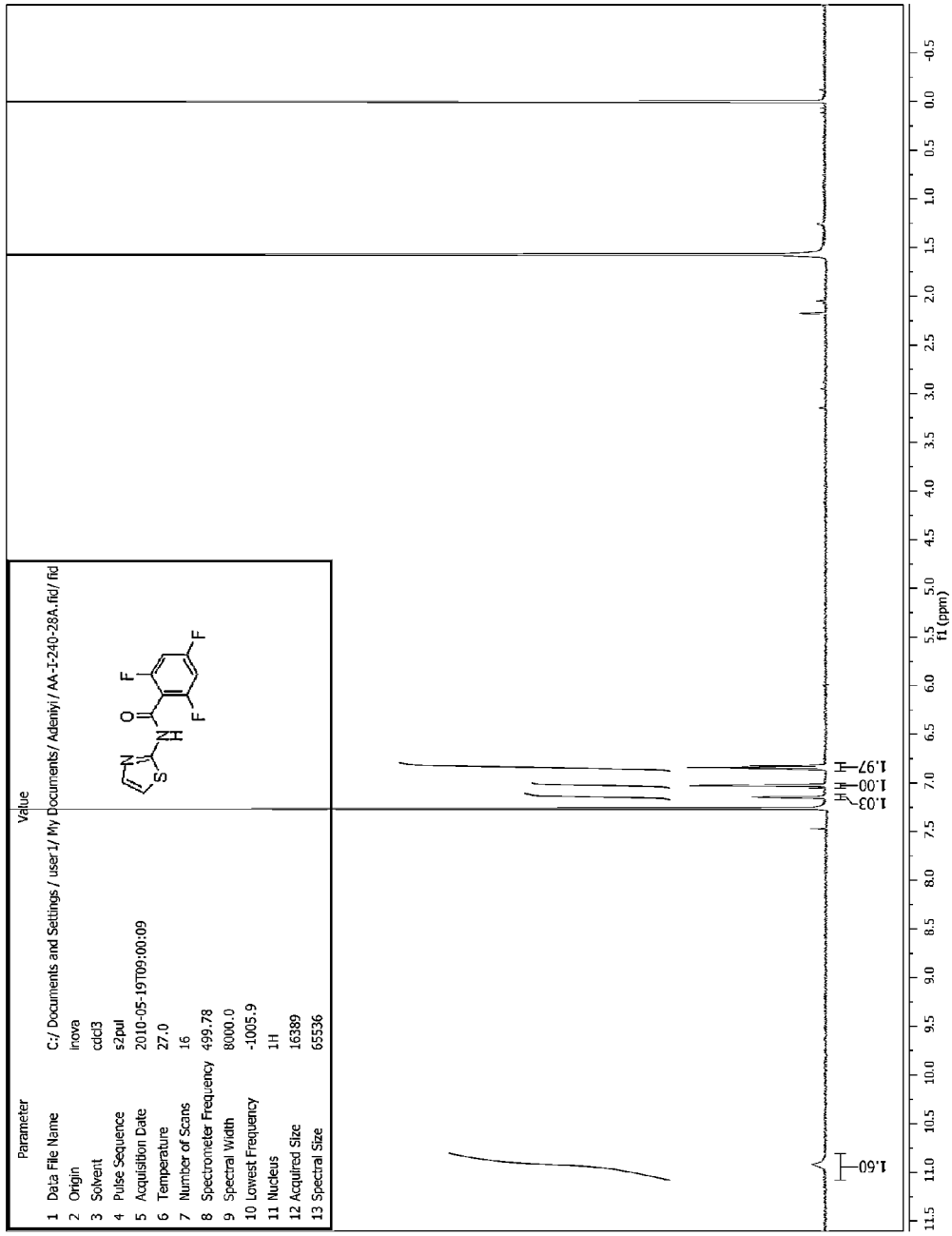
FIG. 25. $^1$H NMR spectrum of CF325.
Figure 26:
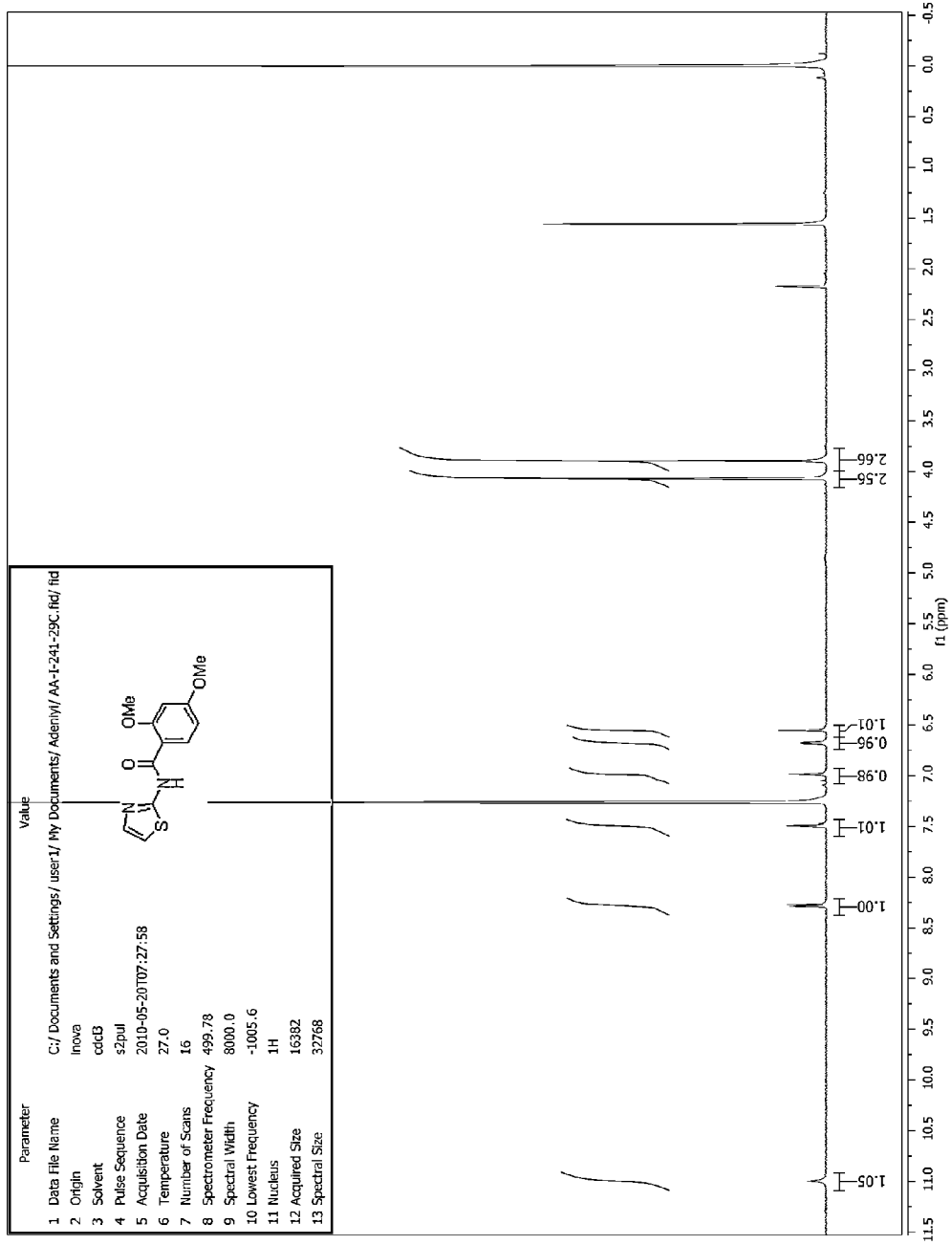
FIG. 26. $^1$H NMR spectrum of CF326.
Figure 27:
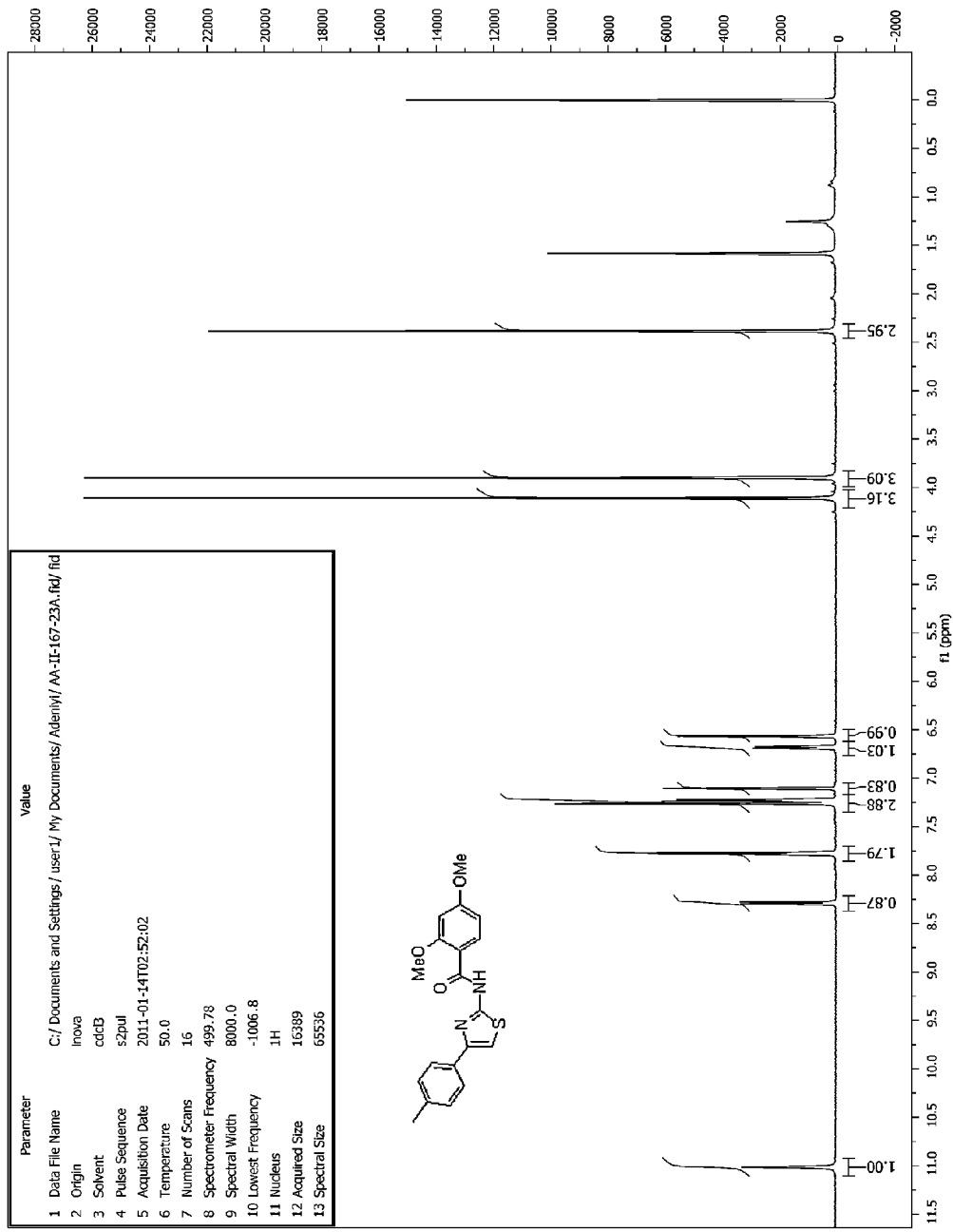
FIG. 27. $^1$H NMR spectrum of CF329.
Figure 28:
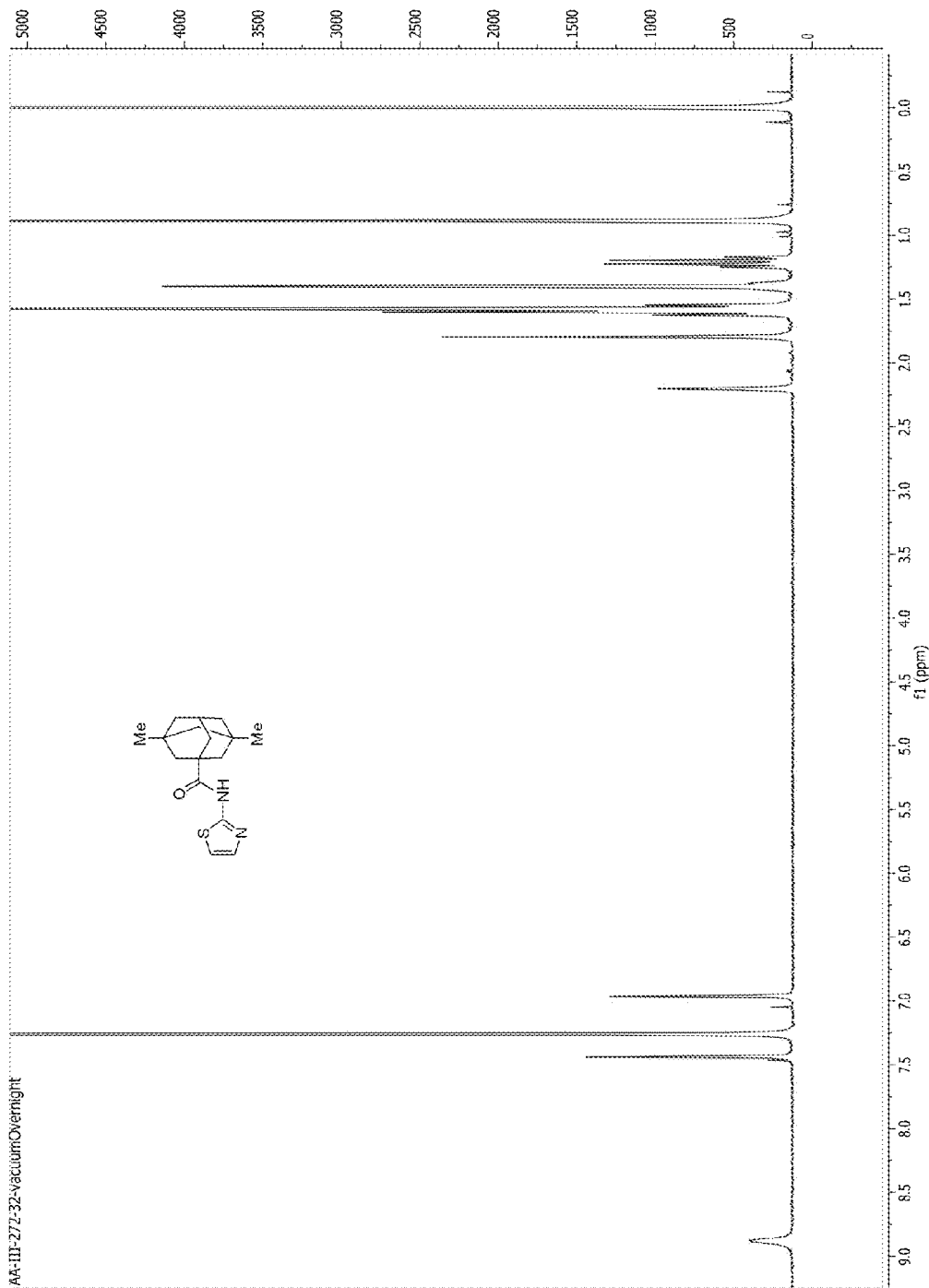
FIG. 28. $^1$H NMR spectrum of CF345.
Figure 29:
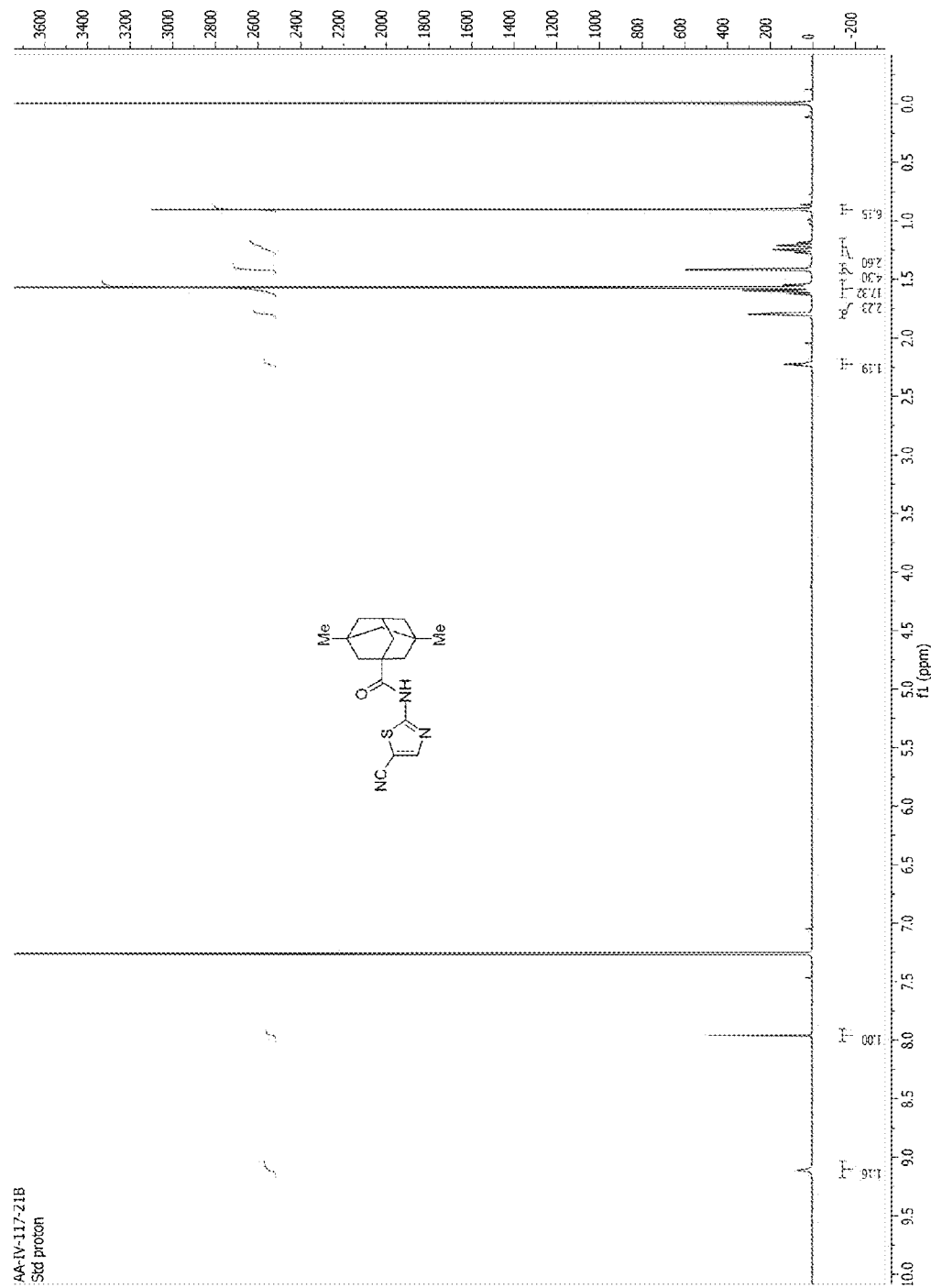
FIG. 29. $^1$H NMR spectrum of CF352.
Figure 30:
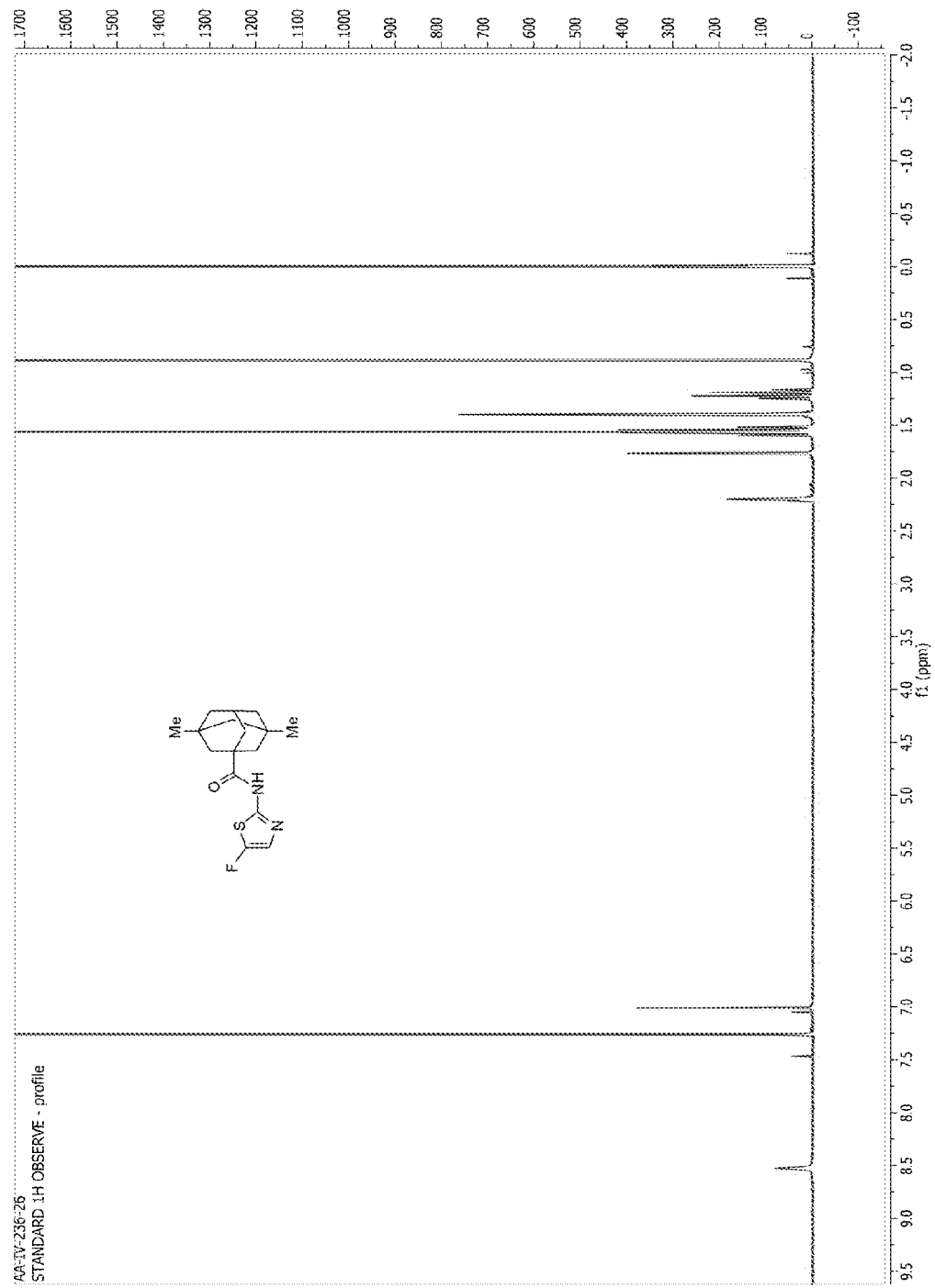
FIG. 30. $^1$H NMR spectrum of CF354.
Figure 31:
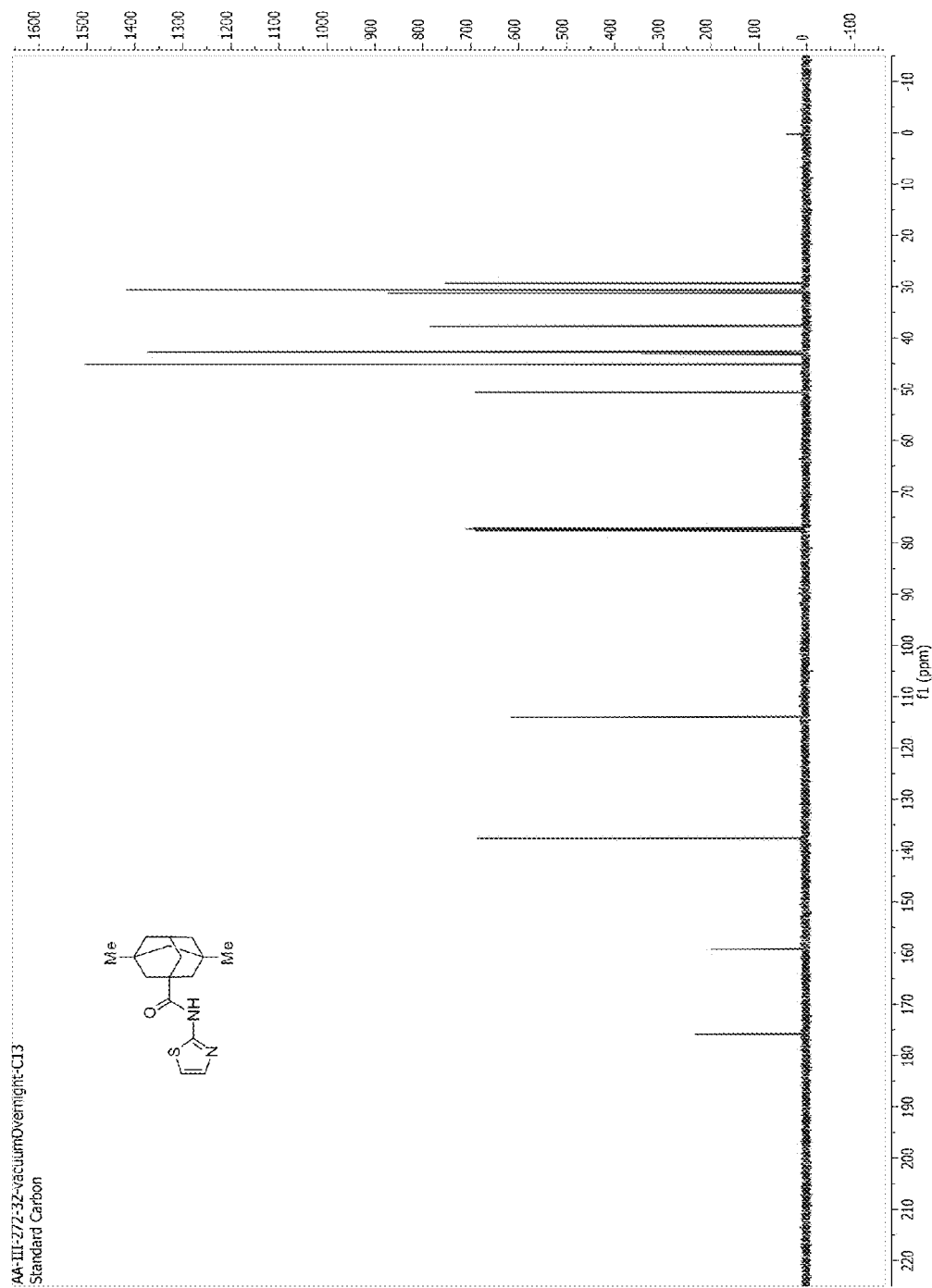
FIG. 31. $^{13}$C NMR spectrum of CF345.
Figure 32:
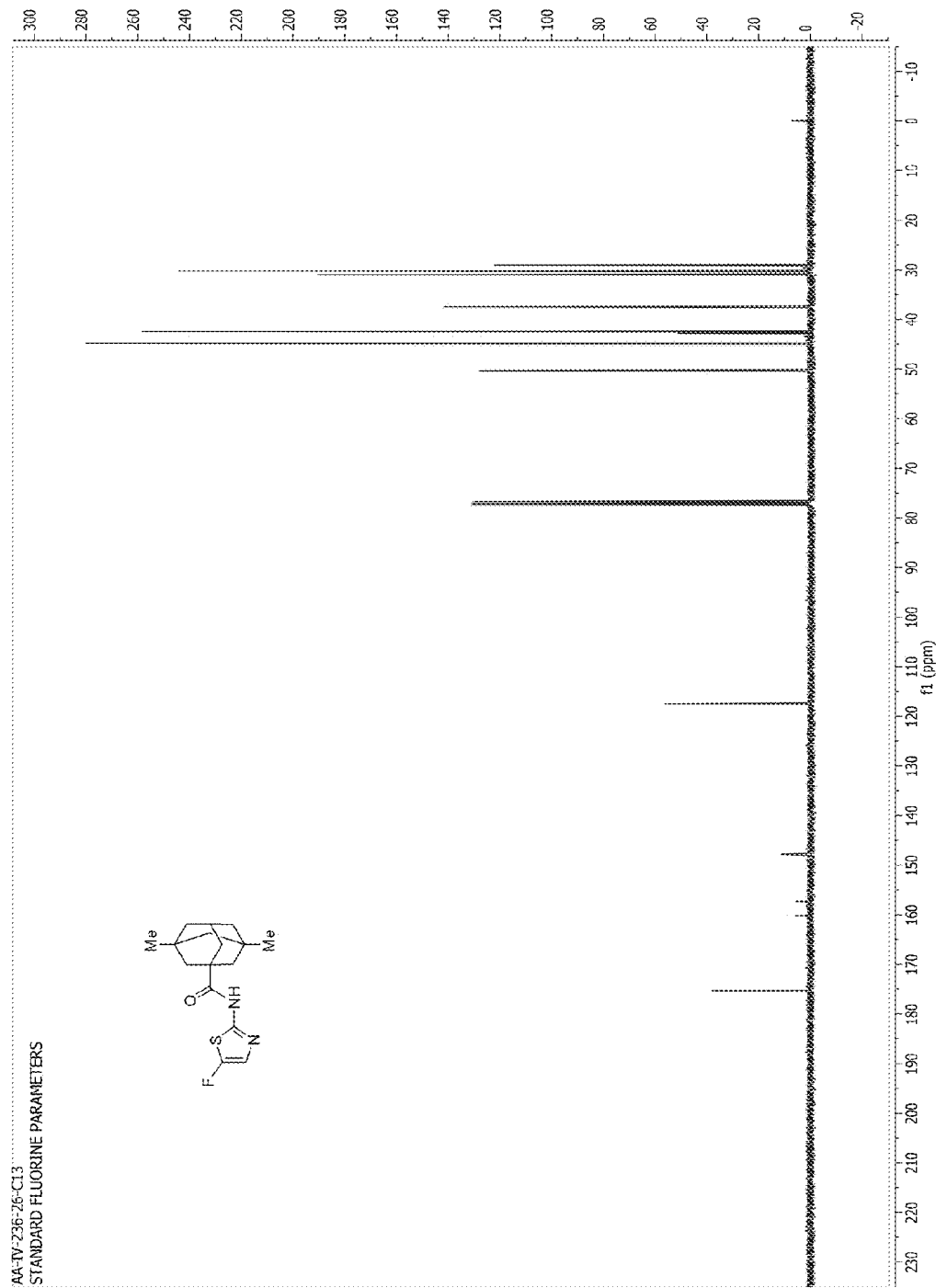
FIG. 32. $^{13}$C NMR spectrum of CF354.
Figure 33:
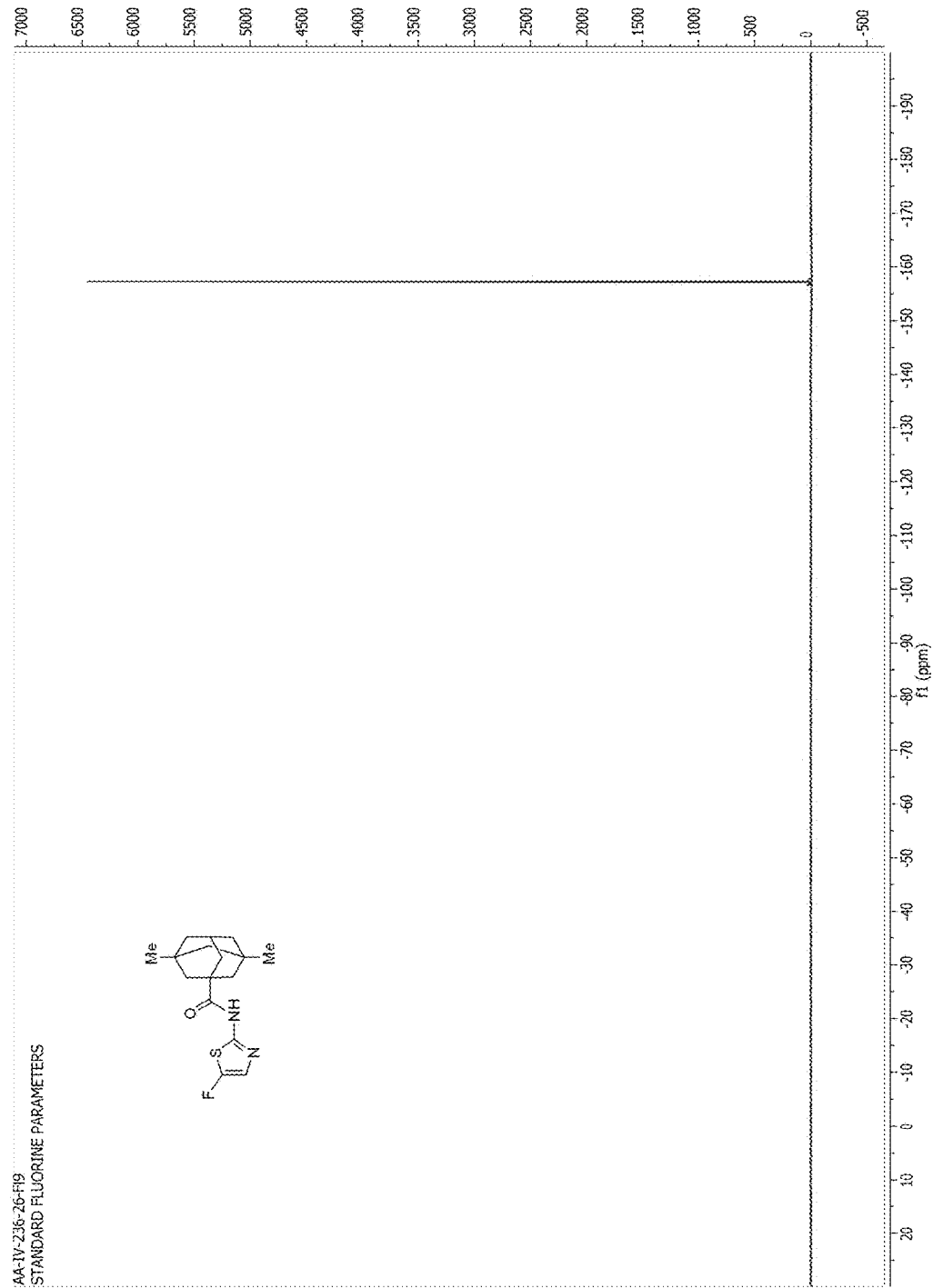
FIG. 33. $^{19}$F NMR spectrum of CF354.

The present invention expands upon the prior art by providing new and novel compounds that, unlike antibiotics, do not kill or hinder bacterial growth but still may be used to treat bacterial infection. These new compounds are not as susceptible to inducing bacterial resistance and thus expand the potentially available remedies for bacterial infection treatment.

A. Bacteria And Bacterial Infections

1. Enterohemorrhagic *E. coli* (EHEC) Serotype O157:H7

EHEC, a category B biothreat agent, is a food born pathogen responsible for major outbreaks of bloody diarrhea and hemolytic uremic syndrome (HUS), a type of kidney failure, throughout the world. Annually in the United States, EHEC is responsible for an estimated 73,000 illnesses, 1,800-3,600 hospitalizations and from 61-541 deaths with combined annual economic costs exceeding $400 million (world wide web at .cdc.gov) (Kapper and O'Brien, 1998). In Argentina, Chile and Uruguay, EHEC is responsible for 40% of the cases of bloody diarrhea. In the U.K., EHEC incidence has increased over the years to 2.7/100,000. In an outbreak in 1996 in Sakai, Japan, there were over 7,500 cases (CDC webpage).

EHEC has a very low infectious dose (as low as 50 colony forming units (cfu)), which is one of the major contributing factors to EHEC outbreaks. EHEC colonizes the large intestine where it causes attaching and effacing (AE) lesions on intestinal epithelial cells. The AE lesion is characterized by the destruction of the microvilli of the colon epithelium and the rearrangement of the cytoskeleton to form a pedestal-like structure, which cups the bacterium individually. The genes involved in the formation of the AE lesion are encoded within a chromosomal pathogenicity island named the locus of enterocyte effacement (LEE).

The mortality associated with EHEC infections stems from the production and release of a potent toxin, named Shiga toxin (Stx), by these bacteria. This potent inhibitor of protein synthesis can be absorbed systemically where it binds to receptors found in the kidneys and central nervous system (CNS), causing HUS, seizures, cerebral edema, and/or coma, Shiga toxin has the same potency and mechanism of action as the plant toxin ricin: it causes cell death in endothelial cells, primarily in the urinary tract that leads to HUS, whose most common outcome is death. The genes encoding Shiga toxin are located within the late genes of a λ-like bacteriophage, and are transcribed when the phage enters its lytic cycle. Disturbances in bacterial envelope, DNA replication, or protein synthesis (which are targets of conventional antibiotics) trigger an SOS response in the bacterial EHEC cells that signals the bacteriophage to enter the lytic cycle. The phage replicates, Shiga toxin is produced, and the phage lyses the bacteria, thereby releasing Shiga toxin in the host. Consequently, treatment of EHEC infections with conventional antimicrobials is highly controversial, and can do more harm than good. In fact, antibiotics promote the expression and release of Shiga toxins, thereby increasing the occurrence and severity of HUS and CNS involvement (Kimmitt et al., 1999; Kimmitt et al., 2000). Currently, there is no treatment for HUS other than plasmaphoresis of this toxin. Consequently, innovative, cost-effective EHEC treatments are urgently needed to address this significant unmet healthcare need.

2. *Salmonella*

*Salmonella enterica*, another category B biothreat agent, includes significant human pathogens responsible for food poisoning and enteric or typhoid fever (Boyle et al., 2007). Nontyphoidal *Salmonella* infections (i.e., 'food poisoning' or Salmonellosis) result in mild to moderate diarrhea, fever, nausea, and cramps which normally resolve without treatment in 4-7 days. Nevertheless, nontyphoidal infections have a large health impact with an estimated ~1.4 million infections, 16,000 hospitalizations, and 400-600 deaths annually in the U.S. In economic terms, the impact has been estimated at $2.4 billion for 2005 (Frenzen, P., 2006). *Salmonella* nomenclature and species identification are complicated. Most food poisonings are caused by *Salmonella enterica* serovar *typhimurium* (*S. typhimurium*) or *Salmonella enterica* serovar *Enteritidis* (*S. Enteritidis*). The latter is often associated with eggs and poultry. By contrast, typhoid fever is caused by *Salmonella enterica* serovar *typhi* (*S. typhi*) but is rare in the U.S. Over 2600 *Salmonella enterica* serovars have been identified (Todar, K., 2005). Studies from around the world show that *Salmonella* has become increasingly resistant to many antibiotics (Crump et al., 2003; Davis et al., 1999; Plant et al., 1982; Nakaya et al., 2003; Samrakandi et al., 2004; Weill et al., 2006). Clearly new treatments for *Salmonella* infections are needed now. Ideally, any new drugs would target new mechanisms and avoid resistance.

3. *Francisella tularensis*

*Francisella tularensis* is a category A biothreat agent that has to be handled within Biosafety Level 3 (BSL-3) plus containment. Tularemia is classically considered a zoonotic disease and the incidence of human infection is low. *F. tularensis* is a highly infectious pathogen, with as few as 10 organisms being capable of causing disease in humans (Golovliov et al., 1997). The disease can have a number of clinical presentations (Prior et al., 2001; Pullen and Stuart, 1945; Stuart and Pullen, 1945, Syrjala et al., 1986). Due to its high infectivity and lethality in humans, *F. tularensis* has been classified as a high-risk agent for bioterrorism. Furthermore, there is very little information on *F. tularensis* pathogenesis, and the only vaccine, *F. tularensis* live vaccine strain (LVS), is not readily available and poorly characterized (Sandstrom, 1994). Although natural infections with *F. tularensis* can be readily treated with antibiotic, this may not be the case with weaponized multi-antibiotic resistant strains—thus, alternative therapeutics are required (Checroun et al., 2006; Clemens et al., 2005; Clemens et al., 2004; Fortier et al., 1995; Lee et al., 2006; Tarnvik, 1999).

4. *Acinetobacter baumannii*

*Acinetobacter baumannii* is an important multi-antibiotic resistant pathogen that causes a variarty of nosocomial infections. It causes nosocomial pneumonia, including ventilator associated pneumonia (VAP), bacteremia, meningitis, and urinary tract infections (Bergogne-Berezin and Towner, 1996). More recently it has been a major cause of serious infections of trops returning from Afeganistan and Iraq (Davis, et al., 2005). The ability of *A. baumannii* to form a biofilm has been implicated in its ability to cause infection, as well as with its enhanced antibiotic resistance (Loehfelm, et al., 2008). *A. baumannii* harbors QseC, and data shows that it produces AI-3, and that biofilm formation by this pathogen can be inhibited by phentolamine, which acts through QseC.

5. Other VAP Pathogens

Besides *A. baumanni*, *K. pneumoniae* and *P. aeruginosa* are important VAP pathogens that are also multi-drug resistant, harbor QseC (Rasko et al., 2008), and have their virulence upregulated by epi/NE (Hegde et al., 2009). The US health care system spends between 4.5 and 11 billion dollars per year to treat VAP, which is caused primarily by these three Gram-negative pathogens.

6. UPEC

The US health care system spends 2.5 billion dollars a year to treat urinary tract infections (UTIs). The primary cause of UTIs is UPEC, and QseC activates expression of all UPEC virulence traits (expression of fimbriae and biofilm formation), and is essential for its virulence in murine infection models (Hadjifrangiskou et al., 2011; Kostakioti et al., 2012b; Kostakioti et al., 2009).

7. Plant Pathogens

Quorum sensing, described in more detail below, plays a role in the activity of certain plant pathogenic bacteria. Bacterial plant pathogens produce an array of enzymes which attack host cell components, and these enzymes play important roles in suppression of host defense response and establishment of infection. Compounds of the present invention may thus be used to treat infected plants or pre-treat plants to prevent such infections.

Bacterial pathogens such as *Erwinia carotovora* produce virulence factors, such as degradative enzymes, which assist the bacteria in entering plant cells and degrading plant tissues. The production of these factors is controlled by quorum sensing. See Pirhonen et al., 1993; von Bodman et al., 2003. Several groups of signal molecules are involved in different microbial quorum sensing systems. See Fuqua et al., 1996; Robson et al., 1997. Among them, the best characterized are the N-acyl homoserine lactones (AHLs), also known as autoinducers (AIs) (a term throughout this application). AHLs are members of a family of widely conserved signal molecules used in the quorum sensing systems of many Gram-negative bacteria. They also are involved in regulation of a diverse range of biological activities including expression of virulence genes of bacterial pathogens such as *Erwinia carotovora, Erwinia chrysanthemi* and *Erwinia stewartii*.

Certain gram-positive bacteria are also affected by quorum sensing. Non-limiting examples of quorum sensing pathogenic bacteria that may cause plant diseases treatable by compounds of the present invention include *Agrobacterium tumefaciens, Pantoea stewartii, Erwinia carotovora, Erwinia chrysanthemi, Erwinia stewartii, Ralstonia solanacearum, Pseudomonas syringae, Pseudomonas aeruginosa* and *Xanthomonas campestris*.

i. *Erwinia*

*Erwinia* is a genus of Enterobacteriaceae bacteria containing mostly plant pathogenic species. It is a gram-negative bacterium related to *E. coli, Shigella, Salmonella* and *Yersinia*. A well-known member of this genus is the species *Erwinia amylovora*, which causes fireblight on apple, pear, and other Rosaceous crops. *Erwinia carotovora* is another plant pathogen. This pathogen, which possesses a QseC sensor, boasts a wide host range (carrot, potato, tomato, leafy greens, squash and other cucurbits, onion, green peppers, etc.) and is able to cause disease in almost any plant tissue it invades. It is a very economically important pathogen in terms of postharvest losses, and a common cause of decay in stored fruits and vegetables. Decay caused by *Erwinia carotovora* is often referred to as bacterial soft rot (BSR). Most plants or plant parts can resist invasion by the bacteria, unless some type of wound is present. High humidity and temperatures around 30° C. favor development of decay on plants or plant parts. Mutants can be produced which are less virulent. Virulence factors include: pectinases, cellulases, (which degrade plant cell walls), and also proteases, lipases, xylanases and nucleases. Other pathogenic *Erwinia* species include *Erwinia chrysanthemi* (causes BSR of corn in the field and in storage) and *Erwinia stewartii* (causes Stewart's wilt in corn).

ii. *Ralstonia*

*Ralstonia* is a genus of proteobacteria, previously included in the genus *Pseudomonas*. One notorious species is *Ralstonia solanacearum*, the causal agent of bacterial wilt. *Ralstonia solanacearum* infects over 100 plant species, such as tomatoes, egg plants, green peppers, tobacco plants, Japanese radishes and strawberries (Kelman, 1953). Ginger, mulberry, banana are also susceptible as well as ornamental plants (e.g., geraniums) (Daughtrey, 2003). The species has been subclassified into at least five races and five biovars. Each race affects a different subset of plants.

*Ralstonia solanacearum* race 3 bv 2 is a strain that has become adapted to temperate climates (Haywood et al., 1998; Stead et al., 1996). Other biovars of *Ralstonia solanacearum* can infect potatoes; however, by 2 is by far the most destructive biovar in temperate areas. The organism has a narrow host range primarily infecting potato (Hayward, 2000). Brown rot has emerged recently as a serious disease of potato in Western Europe (Stead et al., 1996) and *Ralstonia solanacearum* by 2 is listed as a zero tolerance quarantine organism in the European Union (EU) (Official J. Eur. Communities, 1998). In those countries affected by brown rot, the costs of disease surveillance and eradication have become considerable. The pathogen has been reported in potato in Turkey; but it has not yet been observed in potato in the continental U.S. where no regulation in potato currently exists. However, the report of finding by 2 in geranium in Wisconsin (Williamson et al., 2001; Kim et al., 2002) could result in movement of the pathogen into potato. Other *Ralstonia* species contemplated by the present invention include *Ralstonia eutropha* and *Ralstonia metallidurans*.

8. Biofilms

The term "biofilm" as used herein refers to a material which naturally develops when microbes attach to a support that is made of a material including but not limited to stone, metal, plastic, glass and wood. "Biofilm" also refers to filamentous and non-filamentous bacteria that produce an extracellular polysaccharide and proteinaceous material that act as a natural glue to immobilize the cells. In nature, nonfilament-forming microorganisms stick to the biofilm surface, locating within an area of the biofilm that provides an optimal growth environment with respect to pH, dissolved oxygen, and nutrients. Since nutrients tend to concentrate on solid surfaces, including porous surfaces and wet, dry surfaces, a microorganism saves energy through cell adhesion to a solid surface rather than by growing unattached.

Single-celled organisms generally exhibit two distinct modes of behavior. The first is the familiar free floating, or planktonic, form in which single cells float or swim independently in some liquid medium. The second is an attached state in which cells are closely packed and firmly attached to each other and usually a solid surface. The change in behavior is triggered by many factors, including quorum sensing (described below), as well as other mechanisms that vary between species. When a cell switches modes, it undergoes a phenotypic shift in behavior in which large suites of genes are up- and down-regulated.

Biofilms have been found to be involved in a wide variety of microbial infections in the body, perhaps as high as 80% of all infections. The achievements of medical care in industrialized societies are markedly impaired due to chronic opportunistic infections that have become increasingly apparent in immunocompromised patients and the ageing population. Chronic infections remain a major challenge for the medical profession and are of great economic relevance because traditional antibiotic therapy is usually not sufficient to eradicate these infections. One major reason for persistence seems to be the capability of the bacteria to grow within biofilms that protects them from adverse environmental factors. *Pseudomonas aeruginosa*, for example, is not only an important opportunistic pathogen and causative agent of emerging nosocomial infections, but can also be considered a model organism for the study of diverse bacterial mechanisms that contribute to bacterial persistence. *Pseudomonas aeruginosa* is also responsible for biofilm formed in the lungs of cystic fibrosis patients.

Other infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. It has recently been shown that biofilms are present on the removed tissue of 80% of patients undergoing surgery for chronic sinusitis. Biofilms are also present on the teeth of most animals as dental plaque, where they may become responsible for tooth decay. Compounds of the present invention may be employed to treat any condition associated with biofilms formed by quorum sensing bacteria.

B. Bacterial Signaling

Microbes and mammals communicate with each other through an array of hormone and hormone-like chemical compounds. These "signals" however, are hijacked by bacterial pathogens, such as enterohemorrhagic *E. coli* (EHEC) O157:H7, to activate its virulence genes. EHEC senses three signals to activate its virulence genes: one is a bacterial aromatic autoinducer (AI-3) produced by the normal human gastrointestinal (GI) microbial flora; and the other two are the host hormones epinephrine/norepinephrine (NE) produced by the host (Sperandio et al., 2003). Recognition of these three signals is essential for virulence in two different animal models, as determined in the laboratory of one of the present inventors (Clarke et al., 2006).

AI-3 is a quorum sensing (QS) signal produced by several species of bacteria, including commensal *E. coli*, as well as several other intestinal bacterial species (EPEC E2348/69, EHEC O26:H11, EPEC O111:H9, *Klebsiella pneumoniae, Shigella* sp., *Salmonella* sp., *Lactobacillus reuteri*, and *Enterobacter cloacae*) (Walters et al., 2006; Tannock et al., 2005). The wide variety of bacteria able to produce AI-3 suggests that it may serve as a general inter-species QS signal. The bacterial QS AI-3 signal cross-signals with the host hormones epinephrine and norepinephrine (NE). Both epinephrine and NE are present in the GI tract. Both hormones modulate intestinal smooth muscle contraction, submucosal blood flow, and chloride and potassium secretion in the intestine. Epinephrine and NE are recognized by adrenergic receptors in mammalian cells.

The AI-3/epinephrine/NE inter-kingdom signaling cascade is present in several important bacterial pathogens of animals and plants (e.g., enterohemorrhagic *E. coli* (EHEC), uropathogenic *E. coli* (UPEC), *Shigella flexneri, Salmonella typhi* and *typhimurium, Erwinia carotovora, Pasteurella multocida, Haemophilus influenzae, Actinobacillus pleuropneumoniae, Chromobacter violaceum, Pseudomonas aeruginosa, Pseudomonas fluorescens, Burkholderia cepacia, Coxiella burnetti, Yersinia pseudotuberculosis, Yersinia pestis, Francisella tularensis* and *Ralstonia solacearum*) suggesting that this inter-kingdom cross-signaling is not restricted to *E. coli*. The lack of efficient treatments for various bacterial infections caused by these pathogens, due to the controversy posed by administration of conventional antibiotics in certain situations, combined with the growing challenge of antimicrobial resistance and the scarcity of novel antibiotics, highlight the importance of understanding this signaling cascade to design and generate new classes of antimicrobials.

C. The QseC Receptor

QseC is a membrane bound histidine sensor kinase (see FIG. 1). Typically, these sensor kinases constitute two-component systems, acting in concert with response regulators. In response to the environmental signal, the sensor autophosphorylates its own conserved histidine residue. Subsequently, the histidine-bound phosphoryl group of the sensor kinase is transferred onto a specific aspartate residue on the cognate response regulator for activation. The activated response regulator then directly regulates transcription of its target genes. In bacteria, two-component systems are the major system of signal transduction (Igo et al., 1989). Importantly mammals do not harbor histidine sensor kinases, making inhibitors of bacterial histidine kinases as attractive potential novel therapeutics due to their selective toxicity (Lyon and Muir, 2003; Roychoudhury et al., 1993).

QseC is a receptor for the AI-3/Epi/NE signals and is central for the pathogenesis of certain bacteria, such as EHEC, *Salmonella* and *Francisella tularensis*. QseC will directly bind these signals, and in response, augment its autophosphorylation (Clarke et al., 2006). Subsequently, QseC then transfers its phosphate to three response regulators (RRs): its cognate RR QseB, and the non-cognate QseF and KdpE RRs (Hughes, et al., 2009), which then regulate virulence gene expression.

QseC homologs are present in several bacterial pathogens including EHEC, EPEC, UPEC, K-12, *Klebsiella pneumoniae, Acinetobacter baumannii, Shigella flexneri, Salmonella enterica typhi* and *typhimurium, Yersinia pestis, Y. enterocolitica, Y. pseudotuberculosis, Erwinia carotovora, Pasteurella multocida, Haemophilus influenzae, Actinobacillus pleuroneumoniae, Chromobacter violaceum, Pseudomonas aeruginosa, Pseudomonas fluorescens, Burkholderia cepacia, Coxiella burnetti, Ralstonia solacenarum* and *Francisella tularensis*. qseC mutants of enterohemorrhagic *E. coli* (EHEC) (Clarke et al., 2006), *Salmonella typhimurim* (Bearson and Bearson, 2007), and Francisella tularensis (Weiss et al., 2007) are attenuated in animal models of infection. In fact, QseC has been involved in the virulence of every pathogen examined thus far, including EHEC, *Salmonella*, UPEC, non-typeable *Haemophilus influenza, Aeromonas hydrophila, Aggregatibacter actinomycetemcomitans, Edwardsiella tarda*, and *F. tularensis* (Hadjifrangiskou, et al., 2011; Khajanchi, et al., 2012; Kostakioti, et al., 2012a; Kostakioti, et al., 2012b; Kostakioti, et al., 2009; Mokrievich, et al., 2010; Moreira, et al., 2010; Novak, et al., 2010; Rasko, et al., 2008; Unal, et al., 2012; Wang, et al., 2011; Weiss, et al., 2007). Finally, QseC is involved in quorum sensing (QS) signaling, and this signaling is not directly involved in processes essential for bacterial growth. Thus, in theory, inhibitors of QS signaling would not induce selective pressures promoting evolution of bacterial resistance.

Examples of QseC polypeptides include, but are not limited to polypeptides having the amino acid sequence provided in the following database accession numbers: YP_169166, YP_514393, YP_899230, YP_001121274, YP_764109.1, YP_001891028, YP_001677727, YP_123578, YP_095321, YP_126604, YP_286016, NP_820223, YP_001115442, ZP_02062557, YP_981771, YP_001862321, YP_001140960, YP_02843268, NP_439849, YP_001341184, YP_249422, YP_001898056, ZP_00943152, YP_001291883, ZP_01787351, ZP_02007463, ZP_01791137, ZP_02478656, YP_001857419, YP_002258797, ZP_00203211, YP_432917, YP_857714, YP_932480, NP_518670, ZP_01793303, YP_157647, YP_786825, YP_002232952, YP_002256398, ZP_01518082, YP_114371, ZP_01308375, YP_001862413, ZP_02885351, NP_884854, NP_881175, YP_001898159, YP_160589, YP_088436, YP_283657, ZP_03268795, YP_001790728, ZP_03267145, YP_001816214, NP_880853, YP_102133, ZP_00439965, ZP_02446165, YP_002107737, ZP_02884581, NP_885061, NP_889719, YP_582619, NP_840430, YP_725059, YP_558955, ZP_03268804, ZP_00349512, YP_001856676, YP_001100931, YP_001895813, YP_001795885, YP_560317, YP_294751, CAL62240, YP_001100363, YP_284407, YP_984175, YP_001896912, YP_265358, ZP_01915254, YP_001354611, YP_285095, YP_001895822, ZP_01999348, YP_284799, ZP_01224171, YP_367461, YP_001630663, ZP_02842897, YP_001171444, ZP_02886774, NP_253465, YP_545417, YP_001985138, YP_001860133, ZP_02843728, ZP_02906088, YP_690440, YP_542429, NP_417498, YP_001881794, ZP_03069017, YP_001723674, ZP_03034105, ZP_03003495, YP_001745294, ZP_03063918, YP_409231, YP_001464488, YP_001791653, ZP_02885393, YP_001767156, YP_001862321, ZP_02886774, YP_001816214, and ZP_01308375; each of which is incorporated herein by reference as of the filing date of this application. In certain aspects the polypeptide targets of the invention will comprise a HisKA and/or a HARPase_c domain.

Embodiments of the invention include QseC kinase homolog compositions that may include a polypeptide or protein that is or is at least 40%, 50%, 60% 70%, 75%, 80%, 85%, 90%, 95%, 96%, 97%, 98%, or 99% identical or similar, including all values and ranges there between, to QseC kinase as long as key regions, such as its histidine kinase and transmembrane regions, are conserved. Sequence identity and/or similarity can be determined using standard techniques known in the art, such as a Jukes Cantor genetic distance model with 1000 bootstraps (see Yang and Zhang, 2008; Cantor and Jukes, 1966). Percent identity and percent similarity may be calculated by using alignment tools known to and readily ascertainable to those of skill in the art.

D. Multidrug-resistant Bacteria

At least since the early 1980s, studies from around the world show that *Salmonella* has become increasingly resistant to many antibiotics (Davis et al., 1999). Whereas a tiny fraction of isolates were resistant in the early 80's, by the mid-90's nearly 20% were resistant (Glynn et al., 1998). This is attributed in large part to the widespread use of antibiotics as growth agents in livestock, which are the primary reservoir for non-typhoidal *Salmonella*. In the late 90's, the DT104 strain of *S. typhimurium* was shown to be resistant to five agents including ampicillin, chloramphenicol, streptomycin, sulfonamides, and tetracycline. Whereas nalidixic acid was the treatment of choice up to the early 90's, it is seldom used due to the prevalence of resistance strains (Crump et al., 2003). More recently, several ciproflaxin and ceftriaxone resistant strains have emerged (Nakaya et al., 2003; Samrakandi et al., 2004; Weill et al., 2006) as well. Other bacteria have also become resistant to various antibiotics, such as *Staphylococcus, uropathogenic E. coli, Pseudomonas aeruginosa, Klebsiela pneumonia, Acinetobacter baumannii, Enterococcus*, and *Streptococcus*.

The growing worldwide challenge of antimicrobial resistance and the paucity of novel antibiotics underscore the urgent need for innovative therapeutics. The increasing understanding of bacterial pathogenesis and inter-cellular communication, when combined with contemporary drug discovery tools and technologies, provides a powerful platform for translating such basic science into therapeutic applications to combat bacterial infections. Interference with bacterial cell-to-cell signaling via the quorum-sensing (QS) pathway constitutes an especially compelling and novel strategy since it also obviates the development of bacterial resistance. QS allows bacteria to respond to hormone-like molecules called autoinducers and is responsible for controlling a plethora of virulence genes in several bacterial pathogens. Because QS is not directly involved in essential processes such as growth of the bacteria, inhibition of QS should not yield a selective pressure for development of resistance. QS antagonists confuse or obfuscate signaling between bacteria and, unlike antibiotics, do not kill or hinder bacterial growth. Hence, QS antagonists should be viewed as blockers of pathogenicity rather than as antimicrobials.

The innovative approach discovered by the present inventors builds on recently obtained insights into the mechanisms of pathogenicity of enterohemorrhagic *E. coli* O157:H7 (EHEC), *Salmonella* (class B biothreat agents) and *Francisella* tularensis (class A biothreat agent). As determined by the present inventors, these diverse pathogens all sense any one or more three signals to activate transcription of their virulence genes (Clarke et al., 2006). These include a bacterial autoinducer (autoinducer-3, AI-3) produced by these pathogens and the normal gastrointestinal flora (in the case of the enteric pathogens) as well as epinephrine/norepinephrine (epi/NE) hormones produced by the host. Importantly, all of these signaling molecules can trigger the QseC membrane bound sensor kinase present in these three pathogens (and in at least 15 other important human and plant pathogens) thereby relaying the presence of these chemical signals to a complex regulatory cascade leading to transcription of key virulence genes. These transcriptional events enable these three pathogens to infect the host. Because of the central role of the AI-3/epi/NE receptor and its signaling system in bacterial pathogenesis and the presence of this system in a broad array of important animal and plant pathogens, compounds of the present invention that act as inhibitors of this receptor system provide an attractive avenue for drug development.

E. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanate" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof; "mercapto" means —SH; and "thio" means =S; "sulfonyl" means —$S(O)_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "=-=-" represents a single bond or a double bond. Thus, for example, the structure 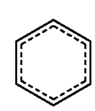 includes the structures , 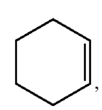 , 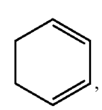 , 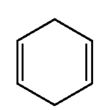  and

.

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "▭▭▭▭" means a single bond where the group attached to the thick end of the wedge is "into the page". The symbol "〰" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

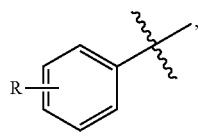

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

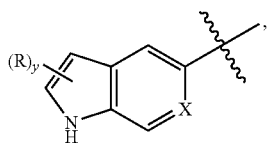

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)$ $CH_3$, —$CH_2NH_2$, —$CH_2NH$-(lower alkyl), such as —$CH_2NHCH_3$ and —$CH_2N(CH_3)_2$, —$CH_2CH_2Cl$, —$CH_2CH_2OH$, $CH_2CH_2OC(O)CH_3$, —$CH_2CH_2NHCO_2C$ $(CH_3)_3$, —$CH_2Si(CH_3)_3$, imidazolidinyl, pyrazolidinyl, morpholinyl, piperazinyl, and thiomorpholinyl. In certain embodiments, lower alkyl refers to —$CH_2NH_2$ or —$CH_2NH$-(lower alkyl), such as —$CH_2NHCH_3$ and —$CH_2N(CH_3)_2$.

In general, the term "lower," as applied to alkyl-containing substituents, refers to the number of carbon atoms being 1-6, e.g., 1, 2, 3, 4, 5, or 6, or any range derivable therein. This term may apply to any alkyl-containing substituent described herein (e.g., alkyl, alkylthio, alkanediyl, aralkyl, alkylamino, dialkylamino, trialkylammonium, etc.)

The term "alkanediyl" refers to both substituted and unsubstituted alkanediyl. When used without the "substituted" modifier, alkanediyl refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2$ $CH_2$—, —$CH_2CH_2CH_2$—, and

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "aryl" includes heteroatom-unsubstituted aryl, heteroatom-substituted aryl, heteroatom-unsubstituted C$_n$-aryl, heteroatom-substituted C$_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted C$_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C$_6$-C$_{10}$-aryl has 6 to 10 carbon atoms. Non-limiting examples of heteroatom-unsubstituted aryl groups include phenyl (Ph), methylphenyl, (dimethyl)phenyl, —C$_6$H$_4$—CH$_2$CH$_3$, —C$_6$H$_4$—CH$_2$CH$_2$CH$_3$, —C$_6$H$_4$—CH(CH$_3$)$_2$, —C$_6$H$_4$—CH(CH$_2$)$_2$, —C$_6$H$_3$(CH$_3$)CH$_2$CH$_3$, —C$_6$H$_4$—CH=CH$_2$, —C$_6$H$_4$—CH=CHCH$_3$, —C$_6$H$_4$C≡CH, —C$_6$H$_4$C≡CCH$_3$, naphthyl, and the radical derived from biphenyl. The term "heteroatom-substituted C$_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C$_1$-C$_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$—CH$_2$OH, —C$_6$H$_4$—CH$_2$OC(O)CH$_3$, —C$_6$H$_4$—CH$_2$NH$_2$, —C$_6$H$_4$CF$_3$, —C$_6$H$_4$CN, —C$_6$H$_4$—CHO, —C$_6$H$_4$—CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, quinolyl, indolyl, and imidazoyl. A "di-substituted aryl group" refers to an aryl group that is substituted by two substituents: the substituents may be heteroatom-unsubstituted or heteroatom-substituted. Additional aryl groups include oxazolyl, isoxazolyl, thiazolyl, isothiazolyl, pyrazolyl, oxadiazolyl, thiadiazolyl, triazolyl, benzofuranyl, benzothienyl, indolizinyl, isoindolyl, isoindolinyl, indolinyl, benzoxazolyl, benzisoxazolyl, benzthiazolyl, benzisothiazolyl, benzimidazolyl, indazolyl, carbazolyl, dibenzofuranyl, dibenzothienyl, fluorenyl, pyridazinyl, triazinyl, tetrazinyl, pentazinyl, isoquinolinyl, quinolizinumyl, quinazolinyl, cinnolinyl, quinoxalinyl, phthalazinyl, napthyridinyl, pteridinyl, purinyl, adeninyl, guaninyl, acridinyl, phenazinyl, anthyridinyl, phenanthrolinyl, phenanthridinyl, phenothienyl, phenoxazinyl, anthracenyl, naphthyridinyl, azepinyl, oxepinyl, thiepinyl, diazepinyl, dioxepinyl, dithiepinyl, triazepinyl, oxazepinyl, thiazepinyl, thiadiazepinyl, tetrazepinyl, thiatriazepinyl, azocinyl, oxocinyl, thiocinyl, diazocinyl, oxazocinyl, and triazocinyl.

Aryl groups (including aryl groups comprised in aralkyl groups) that are optionally mono-, di-, tri-, tetra- or penta-substituted are discussed throughout this disclosure and each specific compound or generic compound of the present invention that comprises an aryl group is specifically contemplated as being optionally mono-, di-, tri-, tetra- or pentasubstituted. Substituents may comprise any aryl substituent recited or shown herein. Non-limiting examples of substituents include halo, —OH, —CO$_2$H, —C(O)NH$_2$, —CN, trihalomethyl, trihalomethoxy, —NH$_2$, —NO$_2$, alkyl (e.g., lower unsubstituted or substituted alkyl), alkoxy (e.g., lower unsubstituted or substituted alkoxy), alkylamino (alkyl-N—), dialkylamino ((alkyl)$_2$N—) and trialkylammonium ((alkyl)$_3$-N(+)), wherein the alkyl groups may be the same or different). In addition, substituted alkyl and substituted alkoxy groups may optionally comprise one, two, three, or more of these substituents. Other substituents are described herein.

The term "aralkyl" refers to substituted and unsubstituted aralkyl. When used without the "substituted" modifier, aralkyl refers to the monovalent group -alkanediyl-aryl, in which the terms alkanediyl and aryl are each used in a manner consistent with the definitions provided herein. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted C$_n$-alkoxy, and heteroatom-substituted C$_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted C$_n$-alkoxy" refers to a group, having the structure —OR, in which R is a heteroatom-unsubstituted C$_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted C$_n$-alkoxy" refers to a group, having the structure —OR, in which R is a heteroatom-substituted C$_n$-alkyl, as that term is defined above. For example, —OCH$_2$CF$_3$ is a heteroatom-substituted alkoxy group.

The term "acyl" includes both substituted and unsubstituted acyl. When used without the "substituted" modifier, acyl refers to a monovalent group, having a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)C$_6$H$_4$—CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group, having a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)

NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl (e.g., pyridinyl) carbonyl" groups.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. The chiral centers of the macromolecules of the present invention can have the S- or the R-configuration, as defined by the IUPAC 1974 Recommendations. As used herein, the phrase "substantially free from other stereoisomers" means that the composition contains ≤15%, more preferably ≤10%, even more preferably ≤5%, or most preferably ≤1% of another stereoisomer(s).

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification ("the parent compound"). Such effects may be enhanced (e.g., slightly more effective, twice as effective, etc.) or diminished (e.g., slightly less effective, 2-fold less effective, etc.) relative to the parent compound, but may still be considered a derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide and azo groups; sulfate, sulfonate, sulfono, sulfhydryl, sulfenyl, sulfonyl, sulfoxido, sulfonamido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

As discussed herein, various chemical groups may be substituted or unsubstituted. For any such substituted group, such as substituted alkyl or substituted aryl, or any group that comprises an alkyl or aryl group (e.g., an alkoxy, alkylamino, dialkylamino, alkylthio, or aralkyl group) the substituent may be any such substituent as known to those of skill in the art. Non-limiting examples of substituents include halo, alkyl, aryl, aralkyl, acyl, alkoxy, alkylthio, alkylamino, dialkylamino, a polymer tail, a polymer backbone, or a linker-polymer backbone.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

Compounds of the present invention may be obtained from commercial sources (e.g., Chembridge Corp., San Diego, Calif.) or synthesized using conventional organic chemistry methods (see, e.g., Example 2). Solvent choices for the methods of making compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography, TLC, or HPLC using a bonded stationary phase.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

The term "functional group" generally refers to how persons of skill in the art classify chemically reactive groups. Examples of functional groups include hydroxyl, amine, sulfhydryl, amide, carboxyls, carbonyls, etc.

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, which is incorporated herein by reference. Compounds of the present invention are specifically contemplated wherein one or more functional groups are protected by a protecting group.

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The above definitions supersede any conflicting definition in any of the reference that is incorporated by reference herein. The fact that certain terms are defined, however, should not be considered as indicative that any term that is undefined is indefinite.

Rather, all terms used are believed to describe the invention in terms such that one of ordinary skill can appreciate the scope and practice the present invention.

F. Pharmaceutical Preparations

Certain of the methods set forth herein pertain to methods involving the administration of a pharmaceutically and/or therapeutically effective amount of a compound of the present invention for purposes of treating bacterial infections.

In certain embodiments, a compound of the present invention may be administered to inhibit bacterial virulence by any method that allows contact of the active ingredient with a bacteria. A compound of the present invention, au be administered by any conventional methods available for use in conjunction with pharmaceuticals, either as an individual therapeutically active ingredient or in a combination of therapeutically active ingredients. A compound of the present invention may be administered alone, but will generally be administered with a pharmaceutically acceptable carrier selected on the basis of the chosen route of administration and standard pharmaceutical practice.

In certain embodiments, a compound of the present invention may be given to a subject who has not responded, or who has negatively responded, to the administration of conventional antibiotics. In certain embodiments, a compound of the present invention is administered to a subject who harbors a multi-drug resistant bacteria or who is suspected of being exposed to a multi-drug resistant bacteria. A compound of the present invention may, in certain embodiments, be administered to a subject who may be threatened with exposure to a multi-drug resistant bacteria. In certain embodiments, a compound of the present invention is administered to a subject who harbors a bacteria containing a QseC sensor or who is suspected of being exposed to a bacteria containing a QseC sensor. A compound of the present invention may, in certain embodiments, be administered to a subject who may be threatened with exposure to a bacteria containing a QseC sensor.

A compound of the present invention may be extensively purified and/or dialyzed to remove undesired small molecular weight molecules and/or lyophilized for more ready formulation into a desired vehicle, where appropriate. Such methods are well-known in the art. The active compounds will then generally be formulated for administration by any known route, such as oral or parenteral administration. Methods of administration are discussed in greater detail below.

Aqueous compositions of the present invention will typically have an effective amount of a compound of the present invention to inhibit bacterial virulence.

Moreover, it will be generally understood that a compound of the present invention can be provided in prodrug form, also discussed above, meaning that an environment to which a compound of the present invention is exposed alters the prodrug into an active, or more active, form. It is contemplated that the term "precursor" covers compounds that are considered "prodrugs."

1. Pharmaceutical Formulations and Routes for Administration to Subjects

Any compound discussed herein is contemplated as comprised in a pharmaceutical composition. Pharmaceutical compositions of the present invention comprise an effective amount of one or more candidate substances (e.g., a compound of the present invention) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA's Center of Drug Evaluation and Research.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, buccally, transdermally, intrapericardially, intraumbilically, intraocularally, orally, locally, via inhalation (e.g., aerosol inhalation), via injection, via infusion, via continuous infusion, via localized perfusion bathing target cells directly, via a catheter, via eye or ear drops, via a lavage, in cremes, in lipid compositions (e.g., liposomes), or by other method or any combination of the foregoing as would be known to one of ordinary skill in the art (see, for example, Remington's Pharmaceutical Sciences, 1990).

A composition comprising a compound of the present invention may be formulated for topical administration, for example, in a cream as mentioned, or in an ointment, salve, spray, gel, lotion, or emulsion. The composition may be formulated for transmucosal, transepithelial, transendothelial, or transdermal administration. One example of transdermal formulation is a patch. The composition may further comprise a chemical penetration enhancer, a membrane permeability agent, a membrane transport agent, a preservative, a surfactant, or a stabilizer, as these terms are known to those of skill in the art.

In one topical embodiment, the present invention can utilize a patch. A transdermal or "skin" patch is a medicated adhesive patch that is placed on the skin to deliver a time released dose of medication through the skin and into the bloodstream. A wide variety of pharmaceuticals can be delivered by transdermal patches. The first commercially available prescription patch was approved by the U.S. Food and Drug Administration in December 1979, which administered scopolamine for motion sickness.

The main components to a transdermal patch are (a) a liner to protect the patch during storage (removed prior to use); (b) the active agent; (c) an adhesive that serves to adhere the components of the patch together along with adhering the patch to the skin; (d) a membrane to control the release of the drug from the reservoir and multi-layer patches; and (e) a backing that protects the patch from the outer environment.

There are four main types of transdermal patches. Single-layer Drug-in-Adhesive patches have an adhesive layer that also contains the agent. In this type of patch the adhesive layer not only serves to adhere the various layers together, along with the entire system to the skin, but is also responsible for the releasing of the drug. The adhesive layer is surrounded by a temporary liner and a backing. Multi-layer Drug-in-Adhesive patches are similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing. Reservoir patches are unlike the Single-layer and Multi-layer Drug-in-Adhesive systems in that the reservoir transdermal system has a separate drug layer. The drug layer is a liquid compartment containing a drug solution or suspension separated by the adhesive layer. This patch is also backed by the backing layer. In this type of system the rate of release is zero order. Matrix patches have a drug layer of a semisolid matrix containing a drug solution or suspension. The adhesive layer in this patch surrounds the drug layer partially overlaying it.

In another form of treatment, a topical application of a compound of the present invention is targeted at a natural body cavity such as the mouth, pharynx, esophagus, larynx, trachea, pleural cavity, peritoneal cavity, or hollow organ cavities including the bladder, colon or other visceral organs. A variety of methods may be employed to affect the topical application into these visceral organs or cavity surfaces. For example, the pharynx may be affected by simply oral swishing and gargling with solutions comprising a compound of the present invention.

In particular embodiments, the composition is administered to a subject using a drug delivery device. Any drug delivery device is contemplated for use in delivering a pharmaceutically effective amount of a compound of the present invention.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In certain embodiments, pharmaceutical compositions may comprise, for example, at least about 0.1% of a compound of the present invention. In other embodiments, a compound of the present invention may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

In certain embodiments, the dosage administered is less than an amount that would be administered of a bacteriostatic or bacteriocidal agents, if such an agent were administered instead. For example, in many types of experiments, bacteriostatic or bacteriocidal agents are administered at a mM range, whereas compounds of the present invention may, in certain embodiments, be administered at a nM range or lower (e.g., about 100 nM or less) such that they achieve methods of the present invention as described herein (e.g., methods of treating or preventing bacterial infection) without killing bacteria. Accordingly, methods of the present invention contemplate administering a compound of the present invention in an amount that is effective to prevent virulence, or pathogenesis, but that is not a bacteriocidal or bacteriostatic amount.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, glycolic, lactic, tartaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, TRIS, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye or ear drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

Dosage formulations of the present pharmaceutical compositions can be prepared by combining them with a pharmaceutically acceptable carrier, such as a slow release agent, to make either immediate or slow release formulations as is well known in the art. Such compositions could be used, for example, in the treatment of periodontal disease and other oral care indications. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters. Immediate and slow release formulations are well known in the art and have been described, for example, in U.S. Pat. No. 4,764,377 (the disclosure of which is incorporated herein by reference), which describes a method for treating periodontal disease by means of a delivery device placed within the periodontal pocket so that release of a therapeutic agent occurs in the immediate vicinity of the disease process. Other means of treating periodontal disease are described in U.S. Pat. No. 5,324,756, the entire contents of which are incorporated herein by reference.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Certain coating materials are those which dissolve at about or at least about a pH of 5 or above, such as at about pH 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 or above, such as pH of about 6.5 or above. Such coatings therefore only begin to dissolve when they have left the stomach and entered the small intestine. Accordingly, these coatings may be considered enteric coatings. A thick layer of coating is provided which will dissolve in minutes to hours, thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy, 1989. For coatings of cellulose esters, a thickness of 200-250 μm would be suitable.

Non-limiting exemplary coating materials are methyl methacrylates or copolymers of methacrylic acid and methyl methacrylate. Such materials are available as EUDRAGIT™ polymers (Rohm Pharma, Darmstadt, Germany). Eudragits are copolymers of methacrylic acid and methyl methacrylate. Compositions may be based on EUDRAGIT™ L100 and Eudragit S100. EUDRAGIT™ L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Certain coating compositions are based on EUDRAGIT™ L100 and EUDRAGIT™ S100 in the range 100 parts L100:0 parts S100 to 20 parts L100:80 parts S100. A non-limiting exemplary range is 70 parts L100:30 parts S100 to 80 parts L100:20 parts S100. For formulations where the ratio of EUDRAGIT™ L100:S100 is high, a coat thickness of the order 150-200 μm is preferable. This is equivalent to 70-110 mg of coating for a size 0 capsule. For coatings where the ratio EUDRAGIT™ L100:S100 is low, a coat thickness of the order 80-120 μm is preferable, equivalent to 30 to 60 mg coating for a size 0 capsule.

It is specifically contemplated that compounds of the present invention may be incorporated into the polymers that act as carriers that are nonabsorbable. Compounds of the present invention may be, for example, covalently bonded to such polymers. Such polymers may be, for example, the polymers mentioned above and/or the polymer tails and polymer backbones discussed herein.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In order to increase the effectiveness of a compound of the present invention, a compound of the present invention may be combined with traditional drugs. For example, an antibacterial agent, an anti-diarrhea agent, and/or an adrenergic antagonist may be administered in combination with a compound with the present invention. It is contemplated that this type of combination therapy may be used in vitro or in vivo.

For example, a compound of the present invention may be provided in a combined amount with an effective amount of a second agent (or more) to inhibit bacterial virulence, such as by inhibiting quorum signaling. This process may involve administering the agents at the same time or within a period of time wherein separate administration of the substances produces a desired therapeutic benefit. This may be achieved by contacting the cell, tissue, biofilm, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue, biofilm, or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound of the present invention is "A" and a second agent, such as an antibacterial agent, an anti-diarrhea agent, and/or an adrenergic antagonist (such as phentolamine, propranolol, or yombine) is "B":

| | | | | | | |
|---|---|---|---|---|---|---|
| A/B/A | B/A/B | B/B/A | A/A/B | A/B/B | B/A/A | A/B/B/B |
| B/A/B/B | B/B/B/A | B/B/A/B | A/A/B/B | A/B/A/B | A/B/B/A | |
| B/B/A/A | B/A/B/A | B/A/A/B | A/A/A/B | B/A/A/A | A/B/A/A | |
| A/A/B/A | | | | | | |

G. Plant Applications

A compound of the present invention may be administered to a plant via any method known to those of skill in the art. For example, in a method of using a composition of the invention to treat a bacterial plant infection, the composition may be diluted in a suitable volume of water to provide an application solution which is then applied to foliage of a plant or plants at an application rate sufficient to give a desired effect (e.g., reduction of bacterial infection). Compounds of the present invention that are water-soluble are particularly suited for spraying, for example. Compounds that are not water-soluble or have limited water solubility may be applied as an emulsion or microemulsion, for example.

Components such as solvents and organic acids may be added to emulsions of the invention to enhance emulsion stability. These additives generally function to increase solubility or dispersability of the surfactants in the aqueous carrier phase thus enabling the formulation of robust emulsions exhibiting enhanced thermal and pH stability, reduced viscosity, and high active agent loading. Solvents may be added to the compositions to increase the solubility or dispersibility of the surfactants in the aqueous carrier phase and thereby attain appropriate stability of the emulsion. Water soluble solvents may be added to increase the solubility of surfactants with a hydrophilic moiety in the aqueous carrier phase. Non-limiting examples of water soluble solvents include acetates, $C_1$-$C_6$-alkanols, $C_1$-$C_6$-diols, $C_1$-$C_6$-alkyl ethers of alkylene glycols and polyalkylene glycols, and mixtures thereof. The alkanol can be selected from methanol, ethanol, n-propanol, isopropanol, the various positional isomers of butanol, pentanol, and hexanol, and mixtures thereof. It may also be possible to utilize in addition to, or in place of, said alkanols, the diols such as methylene, ethylene, propylene and butylene glycols, and mixtures thereof, and including polyalkylene glycols. Mixtures of hydrophobic and hydrophilic solvents may also be used. Organic acids may be added to the compositions to enhance the stability of the emulsion, such as acetic, dichloroacetic, citric, malic, oxalic, salicylic, or tartaric acid. Other additives including inorganic acids and oxidizing agents may be added to the compositions of the invention to enhance emulsion stability. Non-limiting examples include boric acid, perchloric acid, phosphoric acid, sulfuric acid, hydrogen peroxide, lithium perchlorate, sodium phosphate, sodium chlorate and sodium iodide.

A plant treatment composition is preferably dilute enough to be readily sprayed using standard agricultural spray equipment. The selection of application rates that are effective for a composition of the invention is within the skill of an ordinary artisan. Those of skill in the art will likewise recognize that individual plant conditions, weather and growing conditions, as well as the specific active ingredients and their weight ratio in the composition, will influence the degree of effectiveness of treating plant bacterial infections as achieved in practicing this invention.

1. Foliar Application

The term "foliar application" refers to the application of substances to the foliage, or above-ground portions, of plants, and especially application to the leaves of the plants. It is understood in the art that incidental amounts of substances used in foliar applications may filter to or contact the soil, but not in quantities which will permit penetration of the soil and significant contacting of the plant's roots compared to the amount contacting the leaves and other above-ground structures.

Foliar application has been performed on farms, in greenhouses, on flowers, and in other agricultural settings for decades, and is performed in any of a variety of ways known in the art. For example, farmers routinely apply pesticides and other agents to their crops by means of tractor mounted sprayers, by crop dusting, through pressurized sprinklers, and through systems such as elevated hoses used to spray grapevines.

Typically, a compound of the present invention is dissolved or diluted in water, as appropriate, before use. Since farmers have been accustomed for years to mixing pesticides, fertilizers, and other agricultural chemicals for use in their fields, the mixing and application of a compound of the present invention is well within a farmer's skill.

The amount of the mixture to be applied to the fields will depend on several variables. In foliar application, the goal is to moisten the foliage. How much water is necessary to accomplish this will depend largely on the amount of foliage to be covered and the precision of the method of application in directing the mixture to the foliage without also wetting the surrounding area. The amount of foliage will depend, for example, on the amount of age of the plants (young plants typically have smaller leaves than mature plants), the type of plant (different types of plants differ in the amount and density of their foliage) and the health of the plants. Farmers have, of course, applied various chemicals to their crops for years, and are well familiar with judging the amount of liquid needed for foliar application on crops of different ages and types. Once the amount of liquid to be used is determined, the amount of a composition of the present invention to be added to achieve any desired concentration in parts per million is readily determined. The determination of whether the rate of application is sufficient to moisten the foliage is also easily made and the amount readily adjusted until a satisfactory rate is achieved.

It should be noted that some systems, such as sprinkler systems, spray the whole plant while they water the soil. In the art, and as used herein, such methods are considered soil applications since their purpose is to soak the ground and not merely to wet the leaves or other portions above the ground 2. Soil Application The term "soil application" refers to the application of a substance to the soil around a plant, where the intent is either to affect the soil directly or to place the roots of the plant in contact with the substance. Generally, substances applied through a soil application will not contact the foliage, but it is possible that incidental amounts of substances used in soil applications may contact the foliage in quantities which will not significant compared to the amount contacting the roots and other below-ground structures. *Ralstonia solanacearum* infections may, for example, be treated via soil applications since the route of infection is typically through the roots (Daughtery, 2003).

In soil application, the soil is preferably first saturated to wet the particles of the soil so that the composition of the present invention can move freely in the soil and reach the roots of the plants. Therefore, preferably the soil is saturated to 70-80% field capacity with ordinary water prior to agent application. The particular concentration to be chosen varies primarily according to the flow rate of water permitted by the method of application. Methods having a higher flow rate generally require a lower concentration of a compound of the present invention, perhaps because more water containing the mixture reaches the roots of the plants. Conversely, lower flow rates will generally require higher concentrations of a compound of the present invention. Alternatively, the time of the application of the mixture can be altered. Thus, use of a low flow rate and low concentration of mixture can be balanced by increasing the time in which the water containing the mixture is applied. Thus, halving the flow rate or concentration of mixture can be compensated for by doubling the application time of the water-mixture solution. While flow rate is a particularly important variable, the crop to which the mixture is being applied may also help determine the concentration of mixture to be applied. Typically, perennials take higher concentrations than do annuals.

It should be noted that the farmer is usually well aware of the flow rate per acre of the irrigation or other soil application system in place on his or her property, as well as the acreage to be covered. The farmer can calculate the amount of water which will be used in watering the land for any particular amount of time (for example, 300 gallons per minute times 50 acres times 30 minutes is 450,000 gallons of water). The farmer can then calculate how much of a composition of the present invention is needed to result in an application of the desired concentration of the mixture.

A composition of the present invention is applied for a period of time, such as minutes to hours to days. In some cases, the practitioner may want to apply the mixture at a lower concentration, but for a longer period, such as overnight or over several days. Such applications are within the purview of the invention, so long as they result in a decrease in bacterial infection or symptoms thereof. The time of the application will also vary according to the particular method employed.

The practitioner will appreciate that different systems of application have different flow rates. For example, overhead sprinklers generally have relatively higher flow rates than do drip systems. Microsprinkler systems such as Fan Jet typically have flow rates between that of drip systems and that of sprinklers, and accordingly have application times somewhat higher than that of sprinklers.

Compositions of the present invention may be applied to soil by being run through a hose, pipe, drip, sprinkler, irrigation channel, or other mechanism. In practice, the devices used are not necessarily precision equipment. Accordingly, when the water flow is turned off, water will typically continue to drip or run from the hose or through the irrigation channel or other applicator for some time. It is therefore understood that the times of application will generally be an approximation and will be measured from the start of the flow of the mixture to when the flow of the mixture is turned off, whether or not some of the mixture continues to drip or run from the applicator.

Following application of a composition of the present invention, the mixture will typically be in the top few inches of soil. For many plants, the root system is deeper in the soil. It is therefore desirable to help move the mixture 6 to 12 inches into the soil to reach the root structures involved in active uptake. To achieve this, it may be desirable to use a "water push" to create a concentration gradient after application of the agent. This is achieved by following the agent application with an application of water. The water application can be as short as a few minutes or as long as several hours. Such "water pushes" to create concentration gradients are commonly used by farmers in applying agricultural chemicals and are accordingly well known in the art.

3. Application to Harvested Plants

A composition of the present invention may be employed to extend the shelf life of harvested plant matter by reducing or preventing bacterial infection of the plant matter after it has been harvested. For example, a solution or emulsion comprising a compound of the present invention may be employed for this purpose.

Applying a composition of the present invention onto the harvested plant matter may be performed using any method known to those of skill in the art, such as using a dipping or spraying procedure performed at room temperature, during which the harvested plant matter is subjected or exposed to the applied composition for a time period of seconds to minutes and possibly hours. Alternatively, the composition may be brushed on the harvested plant matter using a suitable brush for such an application.

H. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screening for Inhibitors of Bacterial Virulence

A library of 150,000 small organic molecules from UT Southwestern Medical Center, Dallas, Tex., was screened at 5 µM in a high throughput assay to identify inhibitors of QseC-dependent virulence gene activation in EHEC. The first round of positive "hits," represented a diverse range of molecular architecture, was subjected to additional rounds of screening followed by preliminary evaluations for toxicity against bacterial cells in vitro. This yielded a pool of 75 potential inhibitors with $IC_{50}$ values at or below $10^{-5}$ M.

In EHEC, the genes involved in the formation of the AE lesion are encoded within a chromosomal pathogenicity island named the Locus of Enterocyte Effacement (LEE). The LEE region contains five major operons: LEE1, LEE2, LEE3, LEE4 and LEE5, which encode a type III secretion system (TTSS), an adhesin (intimin), and this adhesin's receptor (Tir), which is translocated to the epithelial cell through the bacterial TTSS. The LEE genes are directly activated by the LEE-encoded regulator (Ler), which is the first gene in the LEE1 operon (Kaper et al., 2004). Transcriptional activation of LEE1 can be achieved using spent supernatant (bacteria producing AI-3 are grown to late exponential phase to an $OD_{600}$ 1.0, bacterial cells are pelleted by centrifugation, the supernatant is filtered through a 0.22 μM filter to ensure it is free from bacterial cells; this is now the spent supernatant) from bacterial strains that produce AI-3 in Sperandio et al., 2003 and Walters et al., 2006, which are incorporated herein by reference.

To develop an assay for inhibitors of LEE1 transcriptional activation by AI-3, conditions were identified in which the TEVS232 bacterial strain containing the chromosomal LEE1::lacZ reporter in Sperandio et al., 1999, which is incorporated herein by reference. would respond to the addition of conditioned medium from EHEC 8624 cultures (containing AI-3). After trying a number of different growth conditions, including varying the aeration of overnight cultures, a successful protocol was developed in which fresh TEVS232 were grown in Luria broth to a concentration having 1.1-1.3 O.D. units and were diluted into Dulbecco's Modified Essential Medium (DMEM) and cultured overnight in a shaking incubator at 37° C. In the morning, cultures having an optical density of 0.2 to 0.3 are diluted into DMEM (negative control) or into DMEM containing 10% EHEC preconditioned medium. These bacteria were dispensed in 40 μl volume into the wells of 384 well plates, with the negative control bacterial added to wells of column 24. Wells in columns 2 and 23 received bacteria in conditioned medium and DMSO, wells in columns 3-22 received bacteria in conditioned medium and compounds from the UT Southwestern 150,000 compound file. Compounds were added at a final concentration of 5 μM and 1% DMSO, using a Biomek FX liquid handler.

The plates of bacteria were incubated 5 hours at 37° C. in a 5% $CO_2$ atmosphere. At the end of the incubation, cells were incubated with lysozyme at a final concentration of 0.3 mg/ml for 15 min at 32° C. Beta-Glo™ reagent (Promega) was added, which couples the β-galactosidase produced by the LEE1::LacZ fusion gene to a luciferase reaction, producing an assay that can be read by luminescence after a 4 min incubation at room temperature. The luminescence value of each well is plotted as a function of the number of the well in each column. The hit rate for this initial screen was 7,000, with an error rate of 20%, which upon re-screening yielded a hit rate of 5,600 compounds, which includes compounds that inhibits AI-3 activation of LEE1 transcription, general inhibitors of bacterial transcription, and compounds that are simply toxic. To eliminate the toxic compounds, as well as compounds that were general inhibitors of transcription from the collection of compounds of interest, a secondary screen was performed utilizing a β-lactamase bla::lacZ chromosomal reporter in the same genetic background as the LEE1::lacZ (strain MCAmp found in Sperandio et al., 1999, which is incorporated herein by reference). This secondary screen validated 75 compounds as specific AI-3 inhibitors; of which the lead compounds for these studies were envisioned.

Example 2

Preparation of Certain Compounds of the Present Invention

General Procedure A. To an oven dried flask containing amine (1 mmol), acid chloride (1 equiv), and N,N-dimethylaminopyridine (DMAP, 1.2 equiv) was added $CH_2Cl_2$ (10 mL). The reaction was continued overnight, then quenched with the addition of water (5 mL) and extracted 3 times with $CH_2Cl_2$. The combined extracts were dried over $Na_2SO_4$, filtered and concentrated under vacuum. The residue was purified on preparative TLC to give the desired amide.

General Procedure B. To an oven dried flask containing amine (1.2 equiv), carboxylic acid (1 mmol), EDCI (1.2 equiv), HOBt (1.2 equiv) and N,N-diisopropylethylamine (DIPEA, 1.2 equiv) was added DMF (10 mL). The reaction was continued overnight. After completion by TLC, the reaction was quenched with water (5 mL) and extracted 3 times with EtOAc, dried over $Na_2SO_4$, filtered and concentrated under vacuum. The crude product was purified on prep-TLC to give the desired product.

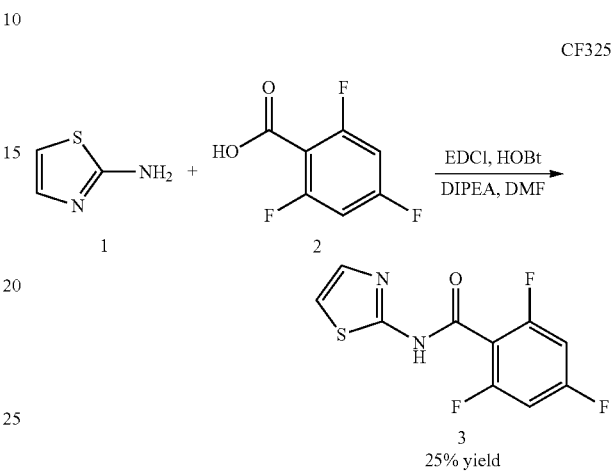

Synthesized according to general procedure B and isolated as white needles. $^1$H NMR (500 MHz, Chloroform-d) δ 11.83 (brs, 1H), 7.00 (d, J=3.2 Hz, 1H), 6.92 (d, J=3.4 Hz, 1H), 6.84 (td, J=8.1, 2.8 Hz, 2H).

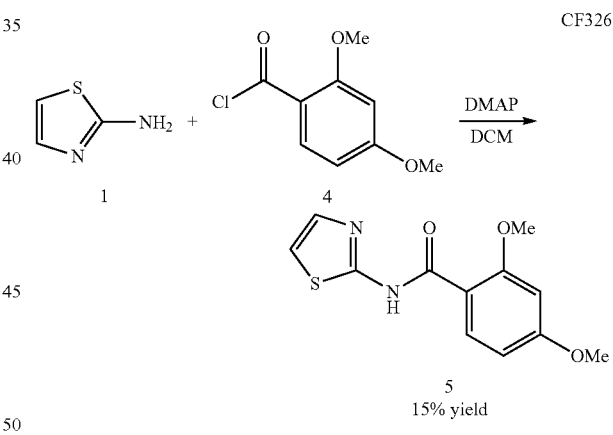

Synthesized according to general procedure A and isolated as white crystals. $^1$H NMR (500 MHz, Chloroform-d) δ 11.00 (brs), 1H), 8.28 (d, 1H, J=9.0 Hz), 7.50 (d, 1H, J=3.5 Hz), 6.99 (d, 1H, J=3.5 Hz), 6.68 (dd, 1H, J=2.5 Hz, J=8.5), 6.55 (t, 2H, J=2.0 Hz), 4.07 (s, 3H), 3.90 (s, 3H).

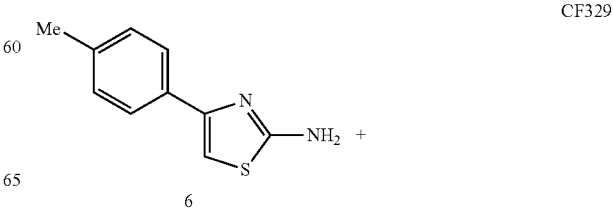

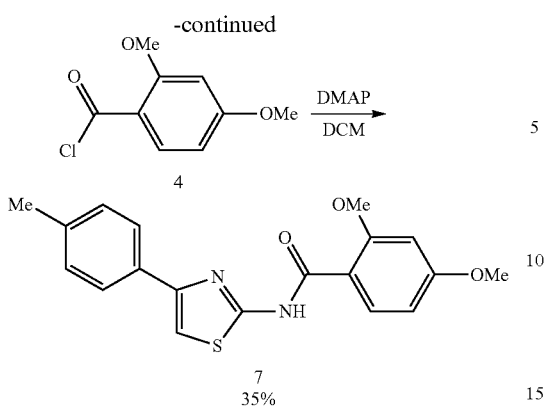

7
35%

Synthesized according to general procedure A and isolated as white solid. $^1$H NMR (500 MHz, Chloroform-d) δ 11.01 (s, 1H), 8.29 (d, J=9.0 Hz, 1H), 7.78 (d, J=7.5 Hz, 2H), 7.23 (d, J=7.5 Hz, 2H), 7.10 (s, 1H), 6.68 (dd, J=9.0 Hz, 1H), 6.57 (s, 1H), 4.11 (s, 3H), 3.90 (s, 3H), 2.39 (s, 3H).

CF331

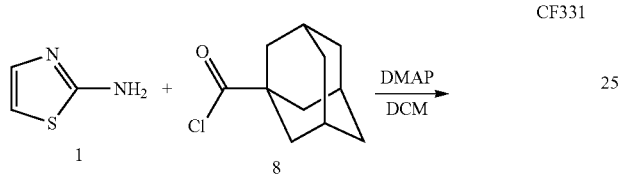

9
45%

Synthesized according to general procedure A and isolated as white solid, MP: 199.5-200.0° C. $^1$H NMR (400 MHz, Chloroform-d) δ 8.89 (s, 1H), 7.44 (d, J=3.6 Hz, 1H), 6.96 (d, J=3.5 Hz, 1H), 2.12 (s, 3H), 1.97 (d, J=2.9 Hz, 6H), 1.77 (app q, J=12.9 Hz, 6H).

CF345

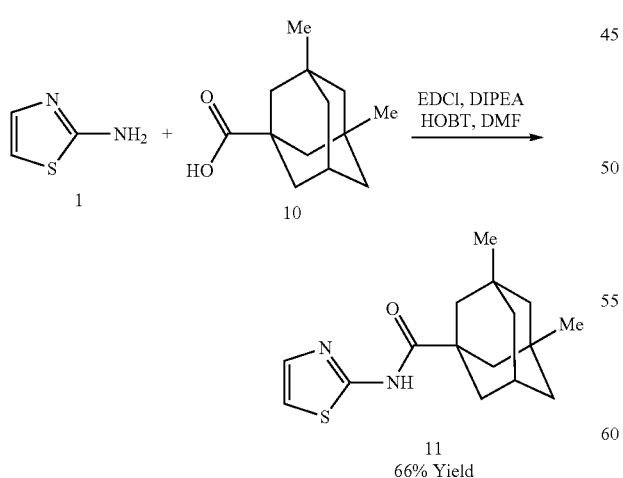

11
66% Yield

Synthesized according to general procedure B and isolated as white solid, m.p. 95.0-95.3° C. $^1$H NMR (500 MHz, Chloroform-d) δ 8.88 (s, 1H), 7.44 (d, J=3.6 Hz, 1H), 6.96 (d, J=3.5 Hz, 1H), 2.20 (p, J=3.2 Hz, 1H), 1.88-1.70 (m, 2H), 1.70-1.48 (m, 12H), 1.40 (t, J=2.5 Hz, 5H), 1.30-1.11 (m, 3H), 0.89 (s, 6H). $^{13}$C NMR (126 MHz, Chloroform-d) δ 175.81, 159.27, 137.64, 113.99, 77.56, 50.63, 45.14, 43.17, 42.75, 37.73, 31.28, 30.59, 29.33.

CF348

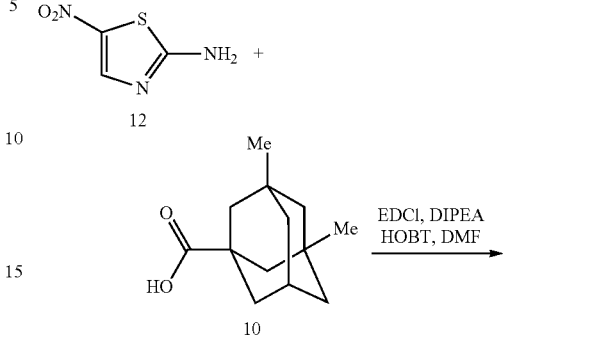

13
96%

Synthesized according to general procedure B and isolated as yellow solid. $^1$H NMR (500 MHz, Chloroform-d) δ 9.04 (s, 1H), 8.31 (s, 1H), 2.23 (p, J=3.2 Hz, 1H), 1.80 (d, J=3.1 Hz, 2H), 1.57 (s, 4H), 1.49-1.35 (m, 4H), 1.35-1.08 (m, 2H), 0.91 (s, 6H).

CF350

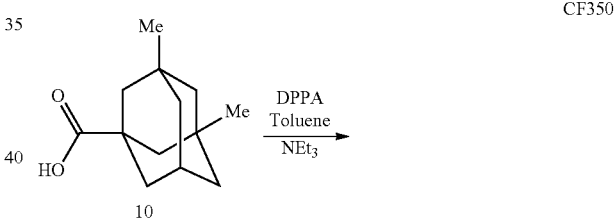

15

To a solution of 10 (300 mg, 1.44 mmol) and triethylamine (1.1 equiv, 220 μL) in toluene (10 mL) at rt was added diphenylphosphoryl azide (DPPA, 1.1 equiv, 342 μL). The reaction was continued at 40° C. for 1 h, and at 80° C. for 4 h. The reaction was cooled to rt, the amine (1.1 equiv, 156 mg) was added at once, and the reaction was continued at 80° C. for 19 h. The reaction was cooled to rt, concentrated in vacuo, and purified on Teledyne Isco Combiflash® RF chromatographic system (12 g SiO$_2$ column: eluted with 0-25% EtOAc/hexanes, 5 min; 25% EtOAc/hexanes, 7 min; 25-100% EtOAc/hexanes, 5 min; 100%, EtOAc, 2 min) to give 15 in 52% yield as a white foam. $^1$H NMR (500 MHz, Chloroform-d) δ 11.06 (br s, 1H), 7.30 (d, J=3.7 Hz, 1H), 6.78 (d, J=3.7 Hz, 1H), 5.30 (s, 1H), 2.18 (dt, J=6.2, 3.4 Hz, 1H), 1.93 (d, J=3.1 Hz, 2H), 1.76 (d, J=11.8 Hz, 2H), 1.68 (d, J=11.8 Hz, 2H), 1.41 (dt, J=12.2, 2.7 Hz, 2H), 1.32 (d, J=12.5 Hz, 2H), 1.18 (qt, J=12.5, 2.1 Hz, 2H), 0.88 (s, 6H).

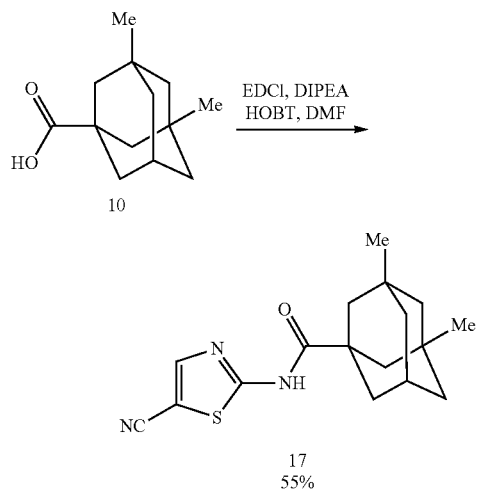

Synthesized according to general procedure B and isolated as white crystals. $^1$H NMR (500 MHz, Chloroform-d) δ 9.11 (brs, 1H), 7.96 (s, 1H), 2.23 (app p, J=3.2 Hz, 1H), 1.79 (d, J=2.5 Hz, 2H), 1.65-1.50 (m, 4H), 1.42 (d, J=2.5 Hz, 4H), 1.30-1.17 (m, 2H), 0.90 (s, 6H).

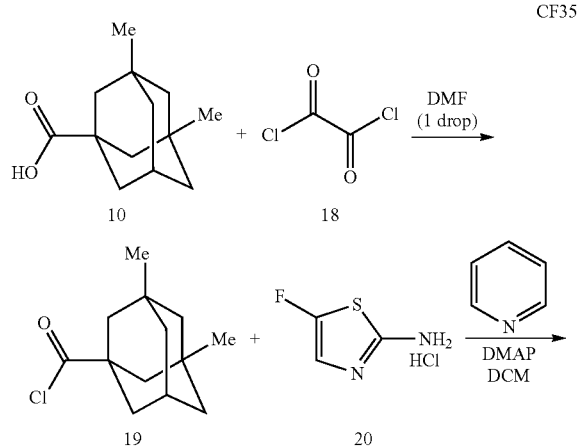

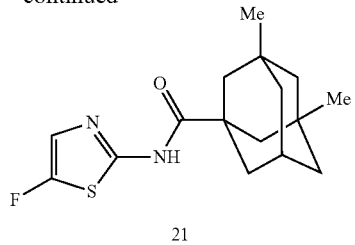

To a vial containing 10 (176 mg, 1.3 equiv) was added neat oxalyl chloride (226 μL) to form a clear solution (bubbling evident). Anhydrous DMF (5 μL) was added and the reaction was continued for 1 h. The reaction was purged with a stream of argon (to get rid of volatile material), concentrated, and dried on high vacuum. The vial was cooled to 0° C. and pyridine (1 mL) and DMAP (1 equiv, 79 mg) were added. After 3 min, 20 (100 mg, 1 equiv.) dissolved in CH$_2$Cl$_2$ (1 mL) was added, the reaction was warmed to r.t. over 10 min, and stirred at 60° C. for 2 hours. The reaction was poured into sat. NH$_4$Cl solution and extracted with EtOAc (2×25 mL). The combined organic extracts were dried over Na$_2$SO$_4$, filtered and concentrated. The crude product was purified via a Teledyne Isco Combiflash® RF chromatographic system (12 g SiO$_2$ column: eluted with hexanes, 2 min, 0-5% EtOAc/hexanes, 7 min; 5% EtOAc/hexanes, 5 min) to give 21 in 65% yield as a white solid, m.p. 125.3-125.6° C. $^1$H NMR (500 MHz, Chloroform-d) δ 8.53 (brs, 1H), 7.01 (d, J=2.5 Hz, 1H), 2.20 (app p, J=3.2 Hz, 1H), 1.77 (d, J=3.0 Hz, 2H), 1.62-1.49 (m, 4H), 1.47-1.37 (m, 4H), 1.28-1.14 (m, 2H) 0.88 (s, 6H). $^{13}$C NMR (100 MHz, Chloroform-d) δ 175.30, 160.22, 157.30, 147.81 (d, J=10.8 Hz), 117.42 (d, J=12.4 Hz), 50.34, 44.86 (2), 42.78, 42.45 (2), 37.45, 31.01 (2), 30.26 (2), 29.02. $^{19}$F NMR (376 MHz, Chloroform-d) δ −157.25 (s, 1F).

All $^1$H, $^{13}$C, and $^{19}$F NMR spectra for the compounds included above are included as FIGS. 25-33.

Example 3

Quantitative Real-time (RT)-PCR

Quantitative real-time (RT)-PCR was used in a variety of the following Examples, and the general protocol is as follows. Overnight cultures grown aerobically in LB for *Salmonella typhimurium*, DMEM for EHEC (WT and qseC mutant found in Sperandio et al., 2002, which is incorporated herein by reference) and Mueller Hinton for *F. tularensis* at 37° C. to either mid-exponential growth phase (OD$_{600}$ 0.5) or late-exponential growth phase (OD$_{600}$ 1.0). For the epinephrine studies, a stock epinephrine solution of 50 mM in water was made and diluted 10$^{-3}$ in overnight cultures that were diluted 1:100 in DMEM for a final concentration of 50 μM. RNA from three biological replicate cultures of each strain was extracted using the RiboPure™—Bacteria RNA isolation kit (Ambion) following manufacturer's guidelines. The primers used in the Real-Time assays were designed using Primer Express v1.5 (Applied Biosystems) (Table 2). Real-Time RT-PCR was performed in a one-step reaction using an ABI 7500 sequence detection system (Applied Biosystems).

| Forward Primer | Reverse Primer |
|---|---|
| *escherichia coli* | |
| ler CGACCAGGTCTGCCCTTCT (SEQ ID 1) | GCCGGAACTCATCGAAA (SEQ ID 2) |
| flicC TCCATCGACAAATTCCGTTCT (SEQ ID 3) | TGGTGACTGCGGAATCCA (SEQ ID 4) |
| stx2A ACCCCACCGGGCAGTT (SEQ ID 5) | GGTCAAAACGCGCCTGATA (SEQ ID 6) |
| flhD TTTCGTCTCGGCATAAATGAA (SEQ ID 7) | TCATTCAGCAAGCGTGTTGAC (SEQ ID 8) |
| eae GCTGGCCTTGGTTTGATCA (SEQ ID 9) | GCGGAGATGACTTCAGCACTT (SEQ ID 10) |
| rpoA GCGCTCATCTTCTTCCGAAT (SEQ ID 11) | CGCGGTCGTGGTTATGTG (SEQ ID 12) |

For each 20 µl reaction, 10 µl 2×SYBR master mix, 0.1 µl Multi-scribe reverse transcriptase (Applied Biosystems), and 0.1 µl RNase inhibitor (Applied Biosystems) were added. Amplification efficiency of each of the primer pairs was verified using standard curves of known RNA concentrations. Melting curve analysis was used to ensure template specificity by heating products to 95° C. for 15 s, followed by cooling to 60° C., and heating to 95° C. while monitoring fluorescence. Once amplification efficiency and template specificity were determined for each primer pair, relative quantification analysis was used to analyze the unknown samples using the following conditions for cDNA generation and amplification: 1 cycle at 48° C. for 30 min, 1 cycle at 95° C. for 10 min, 40 cycles at 95° C. for 15 s and 60° C. for 1 min. The rpoA (RNA polymerase subunit A) gene from each species was used as the endogenous control.

Data collection was performed using the ABI Sequence Detection 1.3 software (Applied Biosystems). Data were normalized to levels of rpoA and analyzed using the comparative critical threshold ($C_T$) method previously described in Anonymous, 1997, which is incorporated herein by reference. The expression level of the target genes at the different growth phases was compared using the relative quantification method in Anonymous, 1997, which is incorporated herein by reference. Real-time data is presented as fold change compared to WT levels at early-exponential growth phase. Error bars represent the standard deviation of the $\Delta\Delta C_T$ value in Anonymous, 1997, which is incorporated herein by reference. Statistical significance was determined by Students t test. A P value of <0.05 was considered significant.

Example 4

Virulence Expression Studies Using Fluorescein Actin Staining (FAS) Test

Fluorescein Actin Staining (FAS) Test. FAS assays were performed as previously described by Knutton et al. (1989). In brief, overnight bacterial cultures grown aerobically in LB at 37° C. were diluted 1:100 and used to infect confluent monolayers of HeLa cells grown on glass coverslips at 37° C. and 5% $CO_2$. Cells were grown for 6 hours at 37° C. and 5% $CO_2$. The coverslips were then washed, permeabilized with 0.2% Triton X-100, treated with FITC-phalloidin to visualize actin accumulation, and propidium iodide was added to stain bacteria. Samples were visualized by immunofluorescence using a Zeiss Axiovert microscope. The entire field of at least six coverslips from each strain was examined and images taken of AE lesions.

Example 5

*Salmonella Typhimurium* Experiments—In Vitro

Mutagenesis of qseC in *S. typhimurium*. Construction of an isogenic *S. typhimurium* SL1344 qseC mutant was carried out as previously described (Datsenko and Wanner, 2000). Briefly, SL11344 cells containing pKD46 were prepared for electroporation. A qseC PCR product was generated using primers depicted in Table 2 and pKD3 as a template and gel purified. Electroporation of the PCR product into these cells was performed, cells were incubated at 37° C. for 2 hours, and plated on media containing 30 µg $ml^{-1}$ chloramphenicol overnight at 37° C. Resulting colonies were patched for chloramphenicol resistance and ampicillin sensitivity, and PCR verified for the absence of the gene. The chloramphenicol cassette was then resolved from the mutant in order to create a nonpolar, isogenic qseC mutant. Plasmid pCP20, encoding a resolvase, was electroporated into the mutant strain, and resulting colonies were patched for chloramphenicol sensitivity.

Example 6

Results of Biological Screening

Compounds CF325, CF326, CF327, CF329, CF330, CF331, CF332, CF333, CF334, CF338, CF339, CF340, CF341, CF342, CF343, CF344, CF345, CF349, CF350, CF351, and CF352 were screened by measuring the inhibition of *S. Typhimurium* replication in the presence (500 and 5 nM) and absence of the compound with J774 macrophage or using a qRT PCR study comparing the levels of gene expression in the presence of 5 and 500 nM concentrations of the target compound. Compounds CF331, CF338, CF340, CF341 and CF345 were also screened using a fluorescein actin staining test to determine the number of HeLa cells infected by measuring the inhibition of AE lesion formation.

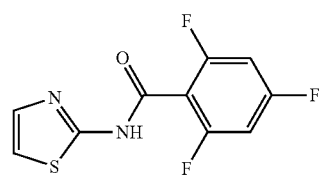

CF325

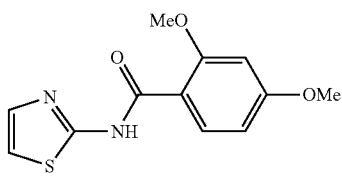

CF326

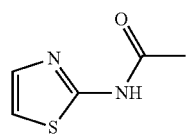

CF327

| | |
|---|---|
| CF329 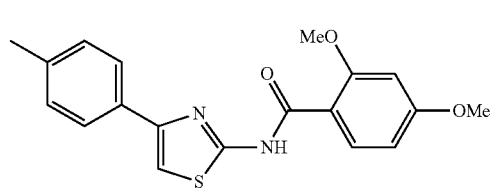 | CF341 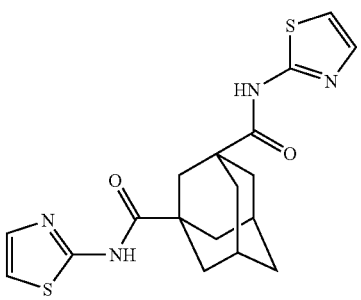 |
| CF330 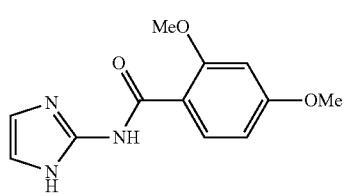 | CF342 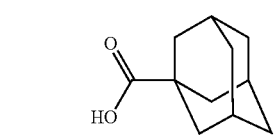 |
| CF331 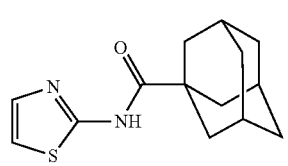 | CF343 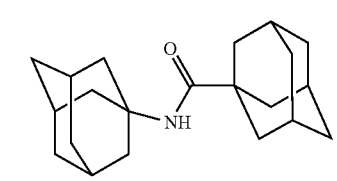 |
| CF332 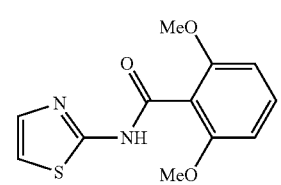 | CF344 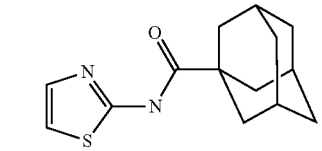 |
| CF333 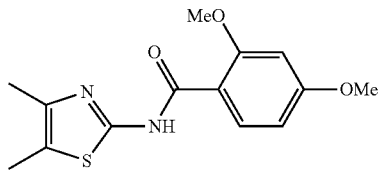 | CF345 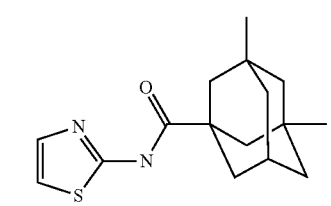 |
| CF334 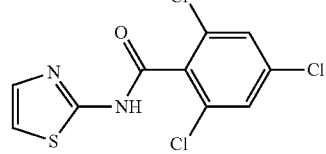 | CF349 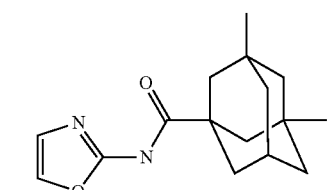 |
| CF338 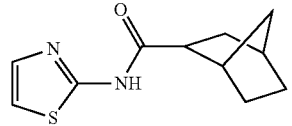 | CF350 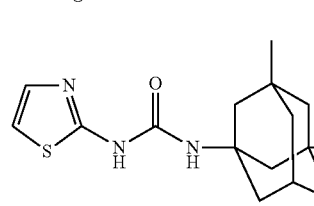 |
| CF339 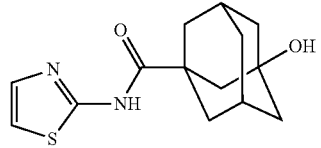 | CF351 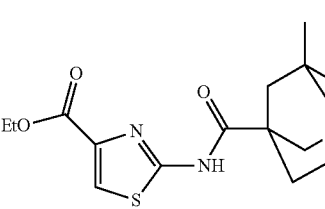 |
| CF340 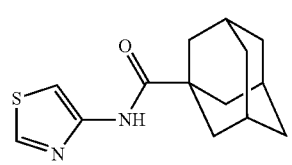 | |

-continued

CF352

[Structure: adamantane-carboxamide linked to thiazole bearing NC group; labeled CF328 is LED209]

CF354

[Structure: dimethyladamantane-carboxamide linked to fluoro-thiazole]

As can be seen in FIGS. 3, 4A, 5A, 7A, 10A, 11, 12, 13B, 14B, 15B, 16B, 17B, and 18B the compounds showed some modification of the infectious ability of the S. Typhimurium virus when the drug was present. Of these compounds, CF325, CF326, and CF334 showed potency in preventing S. Typhimurium virulence, while CF327, CF329, CF332, and CF334 showed little modulation of the virulence of S. Typhimurium. While these structures might not have limited the virulence of the bacteria, the compounds provide important structural activity relationship information for the advancement of the drug class.

In FIGS. 4B, 5B, 6, 7B, 8, 9A, 10B, 11B, 12B, 13A, 14A, 15A, 16A, 17A, 18A, 19, 21, 22, 23, and 24, the results of screenings of each of the compounds using qRT-PCR to determine the gene expression level in EHEC are shown. Compounds CF326, CF329, CF331, CF333, CF345, CF352 and CF354 showed antagonist activity against the virulence of EHEC, including by using qRT-PCR techniques. Among these compounds, CF331 and CF345 showed the greatest modulation of bacterial virulence. On the other hand, compounds CF327, CF328, CF330, CF334, CF349, CF350, and CF351 acted as agonist of virulence. These compounds provide useful information about structure activity relationship in the compound classes as well as potential research tools to study virulence but would not work as anti-microbial compounds.

Finally, FIGS. 9B, 13C, 15C, 16C, and 21B show the results of FAS studies with compounds CF331, CF338, CF340, CF341 and CF345, respectively. As can be seen from the figures, those two compounds modulate the virulence of EHEC in HeLa cells. Those two compounds show a remarkable ability to antagonize EHEC and prevent its virulence in cells.

\*\*\*

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,764,377
U.S. Pat. No. 5,281,170
U.S. Pat. No. 5,324,746
U.S. Pat. No. 5,811,151
U.S. Pat. No. 6,024,918
U.S. Pat. No. 7,256,259
U.S. Pat. No. 8,252,841
Anonymous, In: Applied Biosystems Prism 7700 Sequence Detection System, User Bulletin #2. The Perkin-Elmer Corp., Norwalk, Conn., 1997.
Azzi et al., Mol. Pharmacol., 60:999-1007, 2001.
Bearson and Bearson, Microb. Pathog., Oct. 12, 2007.
Bergogne-Berezin and Towner, Clin. Microbiol. Rev., 9:148-165, 1996.
Boyle et al., J. Bacteriol., 189:1489-1495, 2007.
Bundgaard, Drugs of the Future, 16:443-458, 1991.
Bundgaard, In: Design of Prodrugs, 7-9, 21-24, Elsevier, Amsterdam, 1985.
Cantor and Jukes, Biochem Biophys Res Commun. 3:319-23, 1966.
Checroun et al., Proc. Natl. Acad. Sci. USA, 103:14578-14583, 2006.
Clarke and Sperandio, Microbiology, 57:1734-1749, 2005.
Clarke and Sperandio, Molec. Microbiology, 58:441-445, 2005.
Clarke et al., Proc. Natl. Acad. Sci. USA, 103:10420-10425, 2006.
Clemens et al., Infect. Immun., 72:3204-3217, 2004.
Clemens et al., Infect. Immun., 73:5892-5902, 2005.
Crump et al., Clin. Infect. Dis., 37:75-81, 2003.
Datsenko and Wanner, Proc. Natl. Acad. Sci. USA, 97:6640, 2000.
Daughtrey, M., Mar. 4, 2003 update of material presented by M. Daughtrey, Dept. of Plant Pathology, Cornell University in talk on "New and Re-emerging Diseases in 2003" at the Society of American Florists' 19$^{th}$ Annual Conference on Insect and Disease Management on Ornamentals on Feb. 23, 2003.
Davis et al., Emerg. Infect. Dis., 5:802-806, 1999.
Davis et al., Emerg. Infect. Dis., 11:1218-1224, 2005.
Fortier et al., Infect. Immun., 63:1478-1483, 1995.
Fuqua et al., Annu Rev Microbiol., 50:727-751, 1996.
Glynn et al., N. Engl. J. Med., 338:1333-1338, 1998.
Golovliov et al., Infect. Immun., 65:2183-2189, 1997.
Greene and Wuts, In: Protecting Groups in Organic Synthesis, 3$^{rd}$ ed., John Wiley & Sons, Inc., 1999.
Haywood et al., In: Bacterial Wilt Disease: Molecular and Ecological Aspects, Prior et al., Eds. Springer Verlag, Berlin, Germany, 1998.
Haywood, Ralstonia solanacearum. Encyclopedia of Microbiology, Vol. 4, Second Edition, Academic Press, NY, 2000.
Hadjifrangiskou, M., et al., Mol Microbiol, 80:1516-1529, 2011.

Hegde et al. *Appl Microbiol Biotechnol*, 84:763-776, 2009.
Hughes et al. *PLoS Pathog*, 5:e1000553, 2009.
Igo et al., *Genes Dev.*, 3:1725-1734, 1989.
Kaper et al., *Nat. Rev. Microbiol.*, 2:123, 2004.
Kaper and O'Brien, In: *Escherichia coli O157:H7 and other Shiga toxin-producing E. coli strains*, 1st Ed., ASM Press, Washington, D.C., 1998.
Kelman, North Carolina Agric. Exp. Stn. Tech. Bull. No. 99, 1953.
Khajanchi et al. *Microbiology.*, 158:259-271, 2012.
Kim et al., *Phytopathol.*, 92:S42, 2002.
Kimmitt et al., *Emerg. Infect. Dis.*, 6:458-465, 2000.
Kimmitt et al., *Lancet*, 353:1588-1589, 1999.
Knutton et al., *Infect. Immun.*, 57:1290-1298, 1989.
Kostakioti et al., *Infect Immun*, 80:2826-2834, 2012.
Kostakioti et al., *Infect Immun*, 2012.
Kostakioti et al., *Mol Microbiol*, 73:1020-1031 2009.
Lee et al., *Infect. Immun.*, 74:4002-4013, 2006.
Loehfelm, et al., *J. Bacteriol.*, 190:1036-1044, 2008.
Lyon and Muir, *Chem. Biol.*, 10:1007-1021, 2003.
*March's Advanced Organic Chemistry: Reactions, Mechanisms, and Structure*, 2007.
Mokrievich, A. N., et al., *Biochemistry* (Mosc), 75:443-451, 2010.
Moreira and Sperandio. *Infect Immun*, 80:4344-4353, 2012.
Moreira et al., *Infect Immun*, 78:914-926, 2010.
Nakaya et al., *Emerg. Infect. Dis.*, 9:255-257, 2003.
Novak et al., *Infect Immun* 78:2919-2926, 2010.
*Official J. Eur. Communities* L-235: 139, 1998.
Pirhonen et al., *EMBO J.* 12:2467-2476, 1993.
Plant et al., *Nature*, 297:510-511, 1982.
Prior et al., *J. Appl. Microbiol.*, 91:614-620, 2001.
Pullen and Stuart, *JAMA*, 129:495-500, 1945.
Rasko et al. *Science*, 321:1078-1080, 2008.
Rasmussen and Givskov, *Microbiol.*, 152:895-904, 2006.
Remington's Pharmaceutical Sciences, 18th Ed. Mack Printing Company, pp. 1289-1329, 1990.
Robson et al., *Trends Biotechnol.*, 15:458-464, 1997.
Roychoudhury et al., *Proc. Natl. Acad. Sci. USA*, 90:965-969, 1993.
Samrakandi et al., *FEMS Microbiol. Lett.*, 237:9-17, 2004.
Sandstrom, *J. Chem. Technol. Biotechnol.*, 59:315-320, 1994.
Sen et al., *Anal. Biochem.*, 307:280-286, 2002.
Sharp and Sperandio, *Infect. Immun.*, 75:2432-2440, 2007.
Sperandio et al., *Proc. Natl. Acad. Sci. USA*, 100:8951-8956, 2003.
Sperandio et al., *Mol. Microbiol.*, 43:809, 2002.
Sperandio et al., *Proc. Natl. Acad. Sci. USA*, 96:15196, 1999.
Sperandio et al., *Proc. Natl. Acad. Sci. USA*, 96:15196-15200, 2003.
Stead et al., In: *Brighton Crop Protection Conference—Pests and Diseases*, British Crop Protection Council, Farnham, Surrey, United Kingdom, Pages 1145-1152, 1996.
Stuart and Pullen, *Am. J. Med. Sci.*, 210:223-236, 1945.
Syrjala et al., *J. Laryngol. Otol.*, 100:1169-1176, 1986.
Tannock et al., *Appl. Environ. Microbiol.*, 71:8419-25, 2005.
Tarnvik, *Rev. Infect. Dis.*, 11:440-451, 1989.
Tian et al., *Journal of Labelled Compounds and Radiopharmaceuticals*. 2011, 54, 625-628.
Unal et al., *Int J Med Microbiol*, 302:261-269, 2012.
von Bodman et al., *Ann. Rev. Phytopath.*, 41:455-482, 2003.
Walter and Sperandio, *Infect. Immun.*, 74:5445-5455, 2006.
Walters et al., *J. Bacter.*, 188:5668-5681, 2006.
Wang et al., *Fish Shellfish Immunol*, 30:944-953, 2011.
Weill et al., *Emerg. Infect. Dis.*, 12:1611-1612, 2006.
Weiss et al., *Proc. Natl. Acad. Sci. USA*, 104:6037-6042, 2007.
Williamson et al., *Phytopathol.*, 91:S75, 2001.
Yang and Zhang *Nucleic Acids Res.* 5, 2008.
Zimmerman et al., *J. Biol. Chem.*, 273:19650-5, 1998.

---

What is claimed is:

1. A method of treating a bacterial infection in a subject, comprising administering to the subject an effective amount of the following molecular formula:

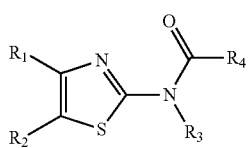

(I)

wherein:
- $R_1$ and $R_2$ are each independently hydrogen, cyano, halo, —C(O)OCH$_2$CH$_3$, $C_1$-$C_8$-alkyl, $C_1$-$C_8$-aryl, or a substituted version of those groups;
- $R_3$ is hydrogen or $C_1$-$C_6$-alkyl; or
- $R_4$ is unsubstituted or substituted heteroatom-unsubstituted $C_1$-$C_{10}$ aryl, $C_1$-$C_6$-alkyl, $C_6$-$C_{12}$-cycloalkyl, or a substituted version of those groups or a pharmaceutically acceptable salt, thereof.

2. The method according to claim 1, wherein $R_3$ is hydrogen.
3. The method according to claim 1, wherein $R_3$ is methyl.
4. The method according to claim 1, wherein $R_1$ is hydrogen.
5. The method according to claim 1, wherein $R_1$ is methyl.
6. The method according to claim 1, wherein $R_2$ is hydrogen.
7. The method according to claim 1, wherein $R_2$ is methyl.
8. The method according to claim 1, wherein $R_2$ are halo.
9. The method of claim 8, wherein $R_2$ is fluoro.
10. The method according to claim 1, wherein $R_1$ is substituted aryl and $R_2$ is hydrogen.
11. The method according to claim 1, wherein the aryl group on $R_1$ is substituted with a methyl group in the 4-position.
12. The method according to claim 1, wherein $R_1$ is cyano and $R_2$ is hydrogen.
13. The method according to claim 1, wherein $R_1$ is hydrogen and $R_2$ is cyano.
14. The method according to claim 1, wherein $R_1$ is —C(O)OCH$_2$CH$_3$ and $R_2$ is hydrogen.
15. The method according to claim 1, wherein $R_4$ is heteroatom-unsubstituted aryl or substituted heteroatom-unsubstituted aryl.
16. The method according to claim 1, wherein $R_4$ is substituted heteroatom-unsubstituted aryl.
17. The method according to claim 1, wherein $R_4$ is a substituted heteroatom-unsubstituted aryl group of the formula:

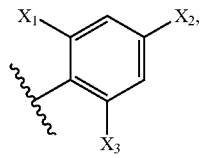

wherein:
$X_1$, $X_2$, and $X_3$ are each independently hydrogen, halo, or —OMe.

18. The method according to claim 1, wherein $R_4$ is a substituted heteroatom-unsubstituted aryl where $X_1$, $X_2$, and $X_3$ are halo.
19. The method according to claim 1, wherein $R_4$ is a substituted heteroatom-unsubstituted aryl where $X_1$, $X_2$, and $X_3$ are —F.

20. The method according to claim 1, wherein $R_4$ is a substituted heteroatom-unsubstituted aryl where $X_1$, $X_2$, and $X_3$ are —Cl.

21. The method according to claim 1, wherein $R_4$ is a substituted heteroatom-unsubstituted aryl where $X_1$ and $X_2$ are —OMe and $X_3$ is hydrogen.

22. The method according to claim 1, wherein $R_4$ is a substituted heteroatom-unsubstituted aryl where $X_1$ and $X_3$ are —OMe and $X_2$ is hydrogen.

23. The method according to claim 1, wherein $R_4$ is alkyl.

24. The method according to claim 1, wherein $R_4$ is methyl.

25. The method according to claim 1, wherein $R_4$ is an unsubstituted or substituted cycloalkyl group.

26. The method according to claim 1, wherein $R_4$ is an unsubstituted or substituted $C_{10}$-$C_{12}$-cycloalkyl.

27. The method according to claim 1, wherein $R_4$ is a group of the molecular formula:

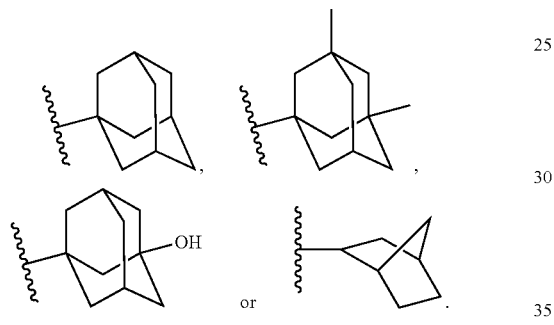

28. The method according to claim 1, wherein the molecular formula of the compound is:

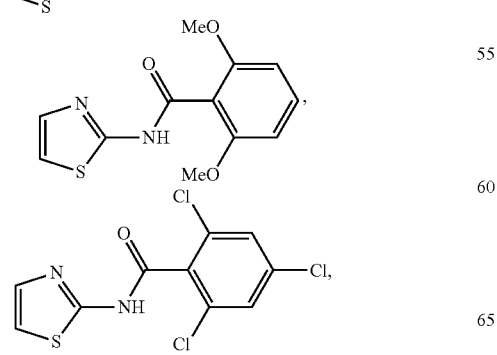

-continued

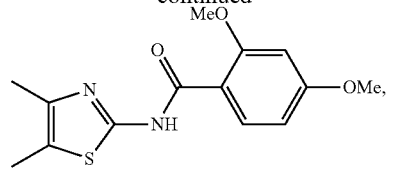

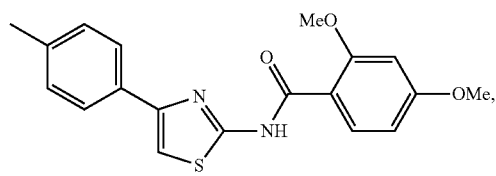

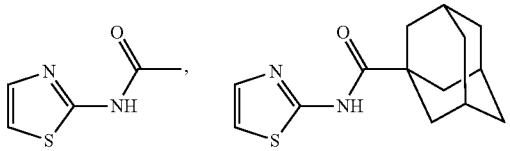

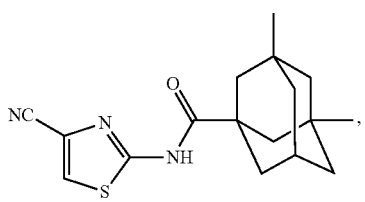

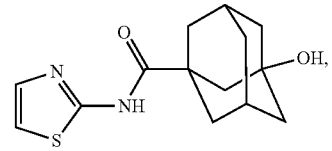

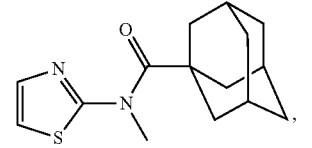

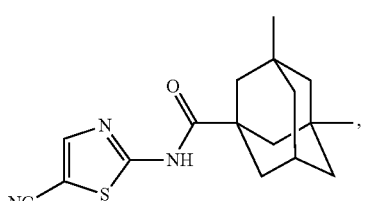

-continued

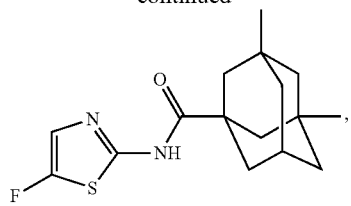

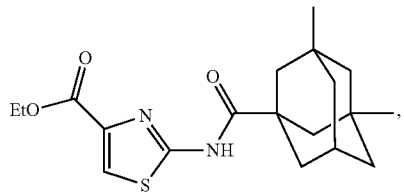

or a pharmaceutically acceptable salt, thereof.

29. A method of treating or preventing bacterial infection in a subject, comprising administering to the subject an effective amount of the following molecular formula:

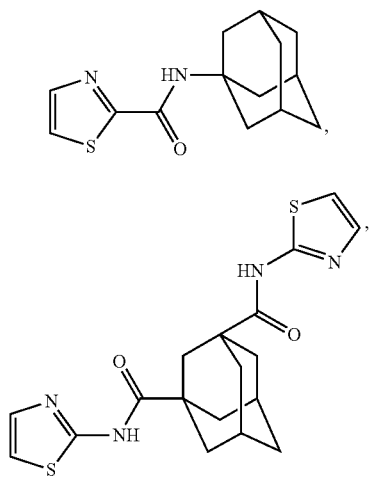

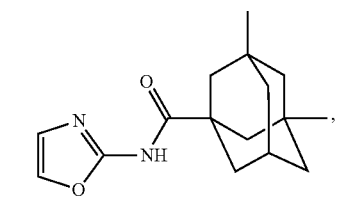

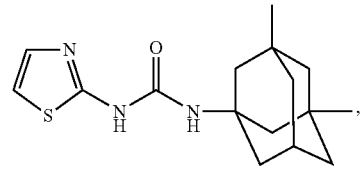

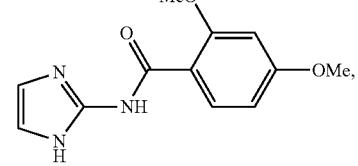

-continued

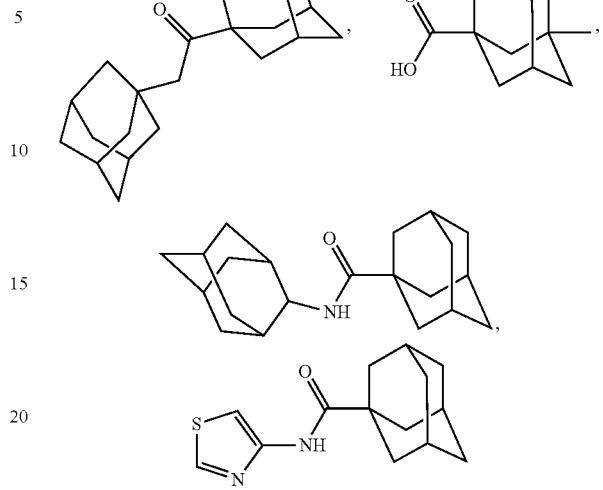

or a pharmaceutically acceptable salt, thereof.

30. The method according to claim 1, wherein the subject is an animal or a plant.

31. The method of claim 1, wherein the bacterial infection is caused by at least one of the organisms *Acinetobacter, Aeromonas hydrophila, Actinobacillus pleuropneumoniae, Bordetella parapertussis, Burkholderia cepacia, Burkolderia phymatum, Chromobacter violaceum, Citrobacter, Coxiella burnetti*, enterotoxigenic *E. coli*, enteropathogenic *E. coli.*, enteroaggregative *E. coli*, enteroinvasive *E. coli*, diffuse adhering *E. coli*, *E. coli* K1, uropathogenic *E. coli*, *E. coli*, *Edwardsiella tarda, Enterobacter, Erwinia carotovora, Francisella tularensis, Klebsiella pseumonia, Haemophilus influenzae, Legionella pneumophila, Pasteurella multocida, Pseudomonas aeruginosa, Pseudomonas fluorescens, Ralstonia euthropha, Ralstonia solanacearum, Shigella flexneri, Salmonella typhi, Salmonella typhimurium, Vibrio cholerae, Vibrio parahaemoliticus, Vibrio vulnificus, Yersinia enterocolitica, Yersinia mollareti, Yersinia pestis,* or *Yersinia pseudotuberculosis.*

32. A compound selected from the group consisting of:

CF325

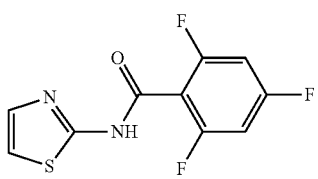

CF326

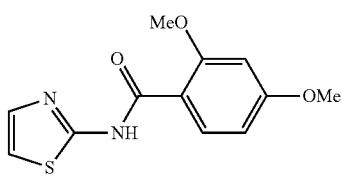

CF327

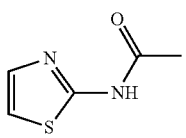

CF329 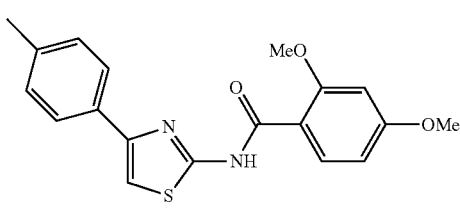
CF330 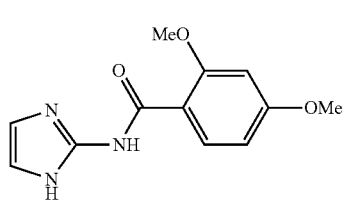
CF331 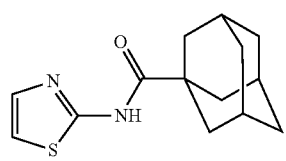
CF332 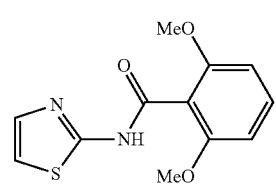
CF333 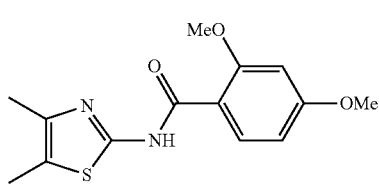
CF334 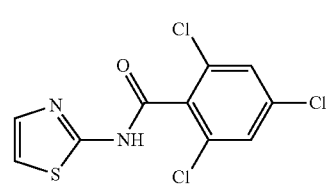
CF338 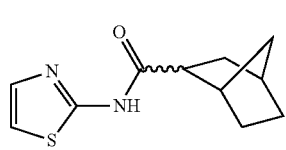
CF339 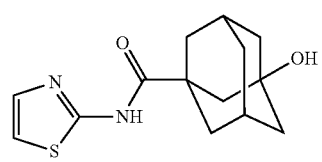
CF340 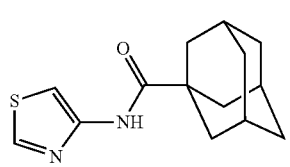
CF341 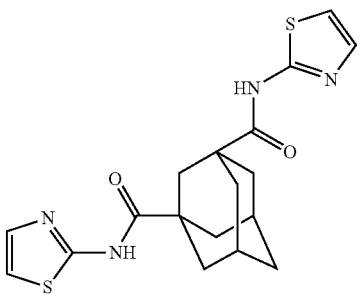
CF342 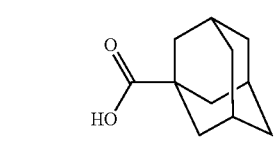
CF343 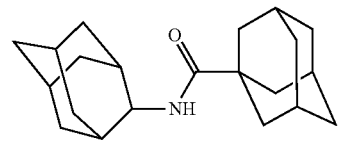
CF344 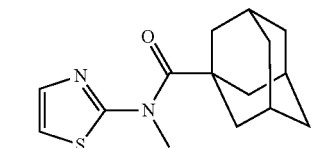
CF345 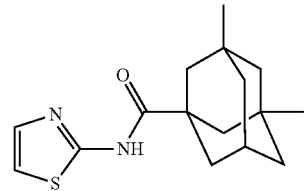
CF349 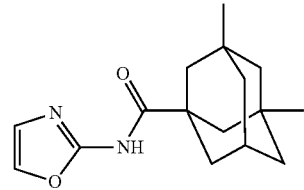
CF350 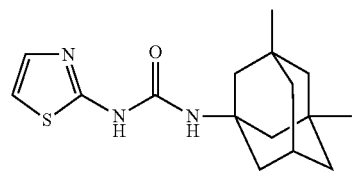
CF351 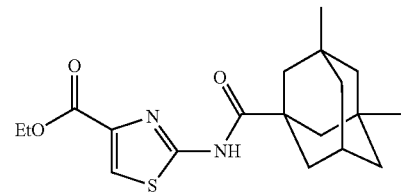

-continued
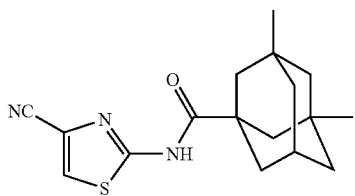
CF352
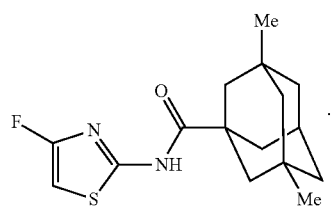
CF354
33. A compound of the formula:
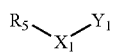
(II)
wherein:
X₁ is
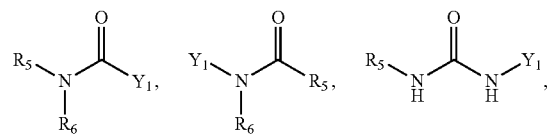
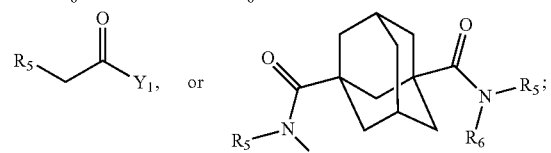
R₅ is
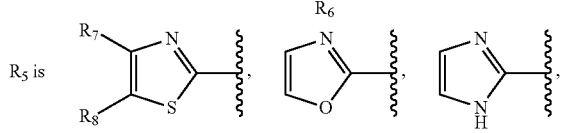
-continued
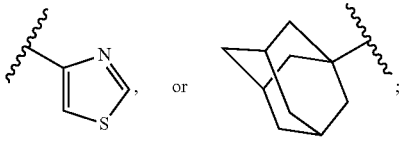
wherein:
R₆ is hydrogen or $C_1$-$C_3$-alkyl;
R₇ and R₈ are each independently hydrogen, cyano, halo, —C(O)OCH₂CH₃,
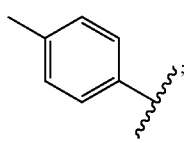 [SMILES: *c1ccc(C)cc1]
and
Y₁ is methyl,
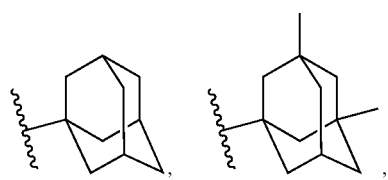
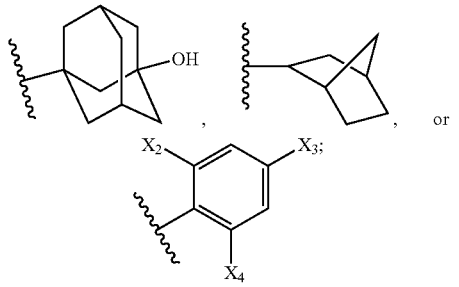
wherein:
X₂, X₃, and X₄ are each independently hydrogen, halo, or —OMe.
* * * * *

UNITED STATES PATENT AND TRADEMARK OFFICE
CERTIFICATE OF CORRECTION

PATENT NO. : 9,604,946 B2
APPLICATION NO. : 14/203202
DATED : March 28, 2017
INVENTOR(S) : Vanessa Sperandio et al.

It is certified that error appears in the above-identified patent and that said Letters Patent is hereby corrected as shown below:

In the Claims

In Claim 29, Column 62, Line 108, delete second chemical drawing in the column and replace with:

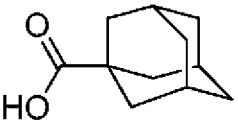

-- --.

In Claim 32, Column 65, Lines 10-18, delete chemical drawing labeled CF354, and replace with:

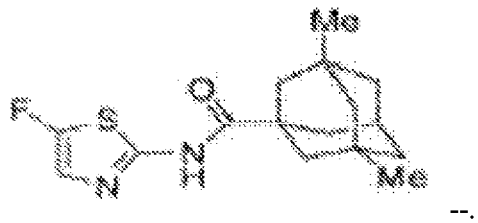

-- --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,604,946 B2
APPLICATION NO. : 14/203202
DATED : March 28, 2017
INVENTOR(S) : Vanessa Sperandio et al.

It is certified that error appears in the above-identified patent and that said Letters Patent is hereby corrected as shown below:

In the Claims

In Claim 29, Column 62, Lines 1-8, delete second chemical drawing in the column and replace with:

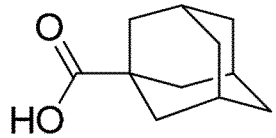

In Claim 32, Column 65, Lines 10-18, delete chemical drawing labeled CF354, and replace with:

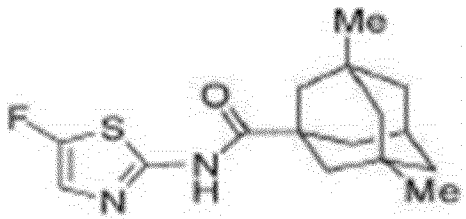

This certificate supersedes the Certificate of Correction issued August 22, 2017.

Signed and Sealed this
Twenty-first Day of August, 2018

Andrei Iancu
*Director of the United States Patent and Trademark Office*

UNITED STATES PATENT AND TRADEMARK OFFICE
CERTIFICATE OF CORRECTION

PATENT NO. : 9,604,946 B2
APPLICATION NO. : 14/203202
DATED : March 28, 2017
INVENTOR(S) : Vanessa Sperandio et al.

Page 1 of 1

It is certified that error appears in the above-identified patent and that said Letters Patent is hereby corrected as shown below:

In the Specification

In Column 1, Lines 8-11, delete paragraph and insert:
--This invention was made with government support under grant number U01 AI177853 awarded by The National Institutes of Health. The government has certain rights in the invention.-- therefor.

Signed and Sealed this
Seventh Day of July, 2020

Andrei Iancu
*Director of the United States Patent and Trademark Office*